(12) United States Patent
Sakaguchi et al.

(10) Patent No.: US 6,222,906 B1
(45) Date of Patent: Apr. 24, 2001

(54) X-RAY DIAGNOSTIC APPARATUS USING AN X-RAY FLAT PANEL DETECTOR AND METHOD FOR CONTROLLING THE X-RAY DIAGNOSTIC APPARATUS

(75) Inventors: Takuya Sakaguchi; Akira Tsukamoto; Masayuki Nishiki; Naoto Watanabe, all of Tochigi (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/238,914

(22) Filed: Jan. 28, 1999

(30) Foreign Application Priority Data

Jan. 29, 1998 (JP) .................................................. 10-017501
Feb. 17, 1998 (JP) .................................................. 10-034999
Mar. 11, 1998 (JP) .................................................. 10-060133

(51) Int. Cl.[7] ...................................................... A61B 6/00
(52) U.S. Cl. ............................................. 378/98.8; 378/95
(58) Field of Search ............................... 378/62, 95, 98.2, 378/98.7, 98.8, 98.12, 114, 115, 116, 204, 205

(56) References Cited

U.S. PATENT DOCUMENTS 5,530,935 * 6/1996 Dillen .................. 378/98.2
5,848,123 * 12/1998 Strommer ............. 378/98.8
5,883,937 * 3/1999 Schmitt ................ 378/189
6,067,343 * 5/2000 Brendler et al. ....... 378/98.7

OTHER PUBLICATIONS

Japan Abstracts, AN 96–047491, JP 8–47491, Feb. 20, 1996.
Japan Abstracts, AN 97–038071, JP 9–38071, Feb. 10, 1997.

* cited by examiner

Primary Examiner—David P. Porta
(74) Attorney, Agent, or Firm—Oblon, Spivak, McClelland, Maier & Neustadt, P.C.

(57) ABSTRACT

Pixel data in a region of a flat panel detector is obtained and displayed. For example, pixel data in a region irradiated with X-ray is obtained and displayed. The region to be irradiated with-the X-ray is estimated according to a degree of opening of an X-ray beam limiting device and a distance between the X-ray beam limiting device and the flat panel detector. Further, it can be determined from pixel data value of the flat panel detector also. A region of a patient can be also determined from the pixel data. Thus, an image corresponding to the entire flat panel detector, an image corresponding to an X-ray irradiation region and an image corresponding to a patient region can be displayed. A resolution for obtaining the pixel data is changed corresponding to the size of a region in the flat panel detector whose pixel data should be obtained and a processing resolution of an image processing means at post step. Particularly in an X-ray diagnostic apparatus of bi-plane structure, an observation region can be traced flexibly.

35 Claims, 37 Drawing Sheets

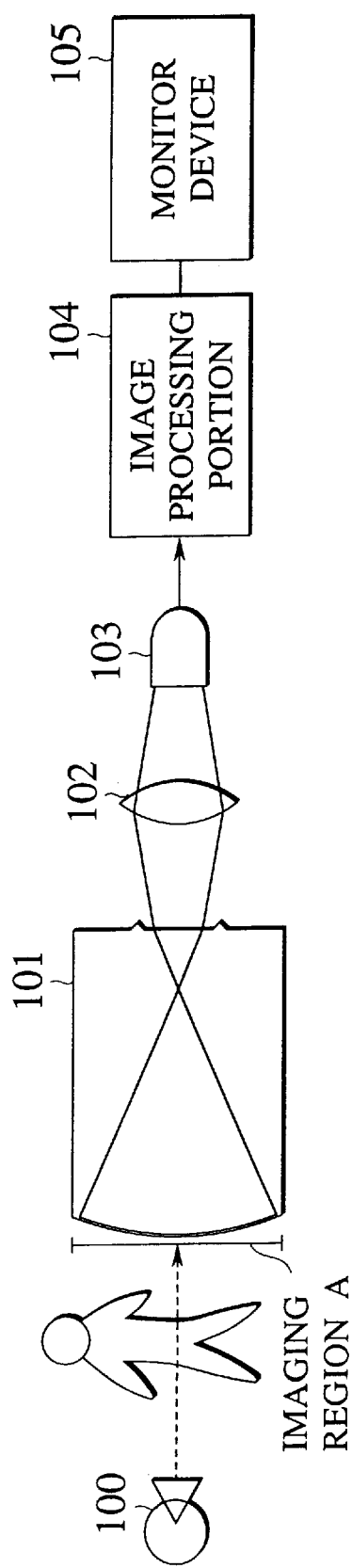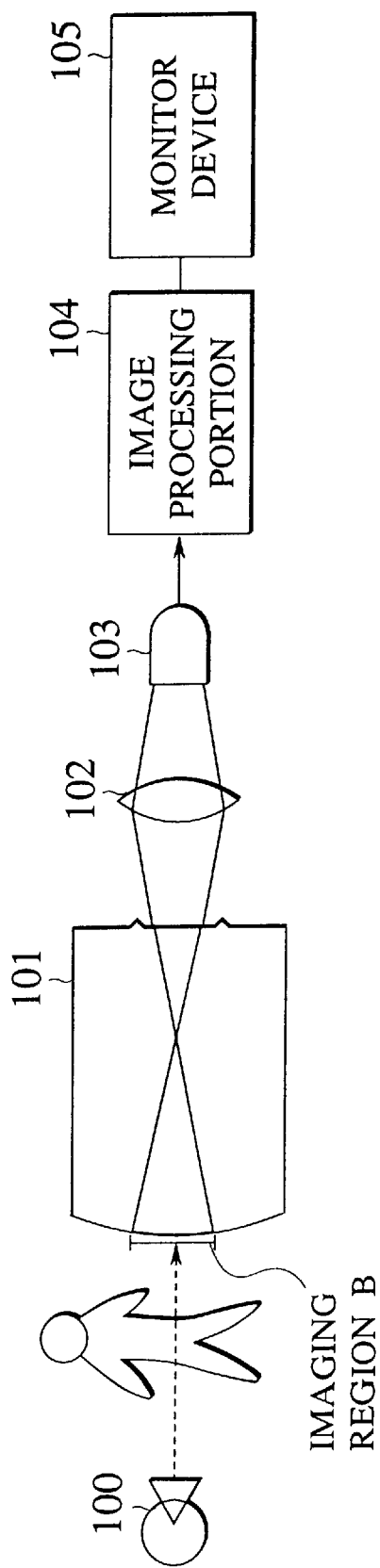

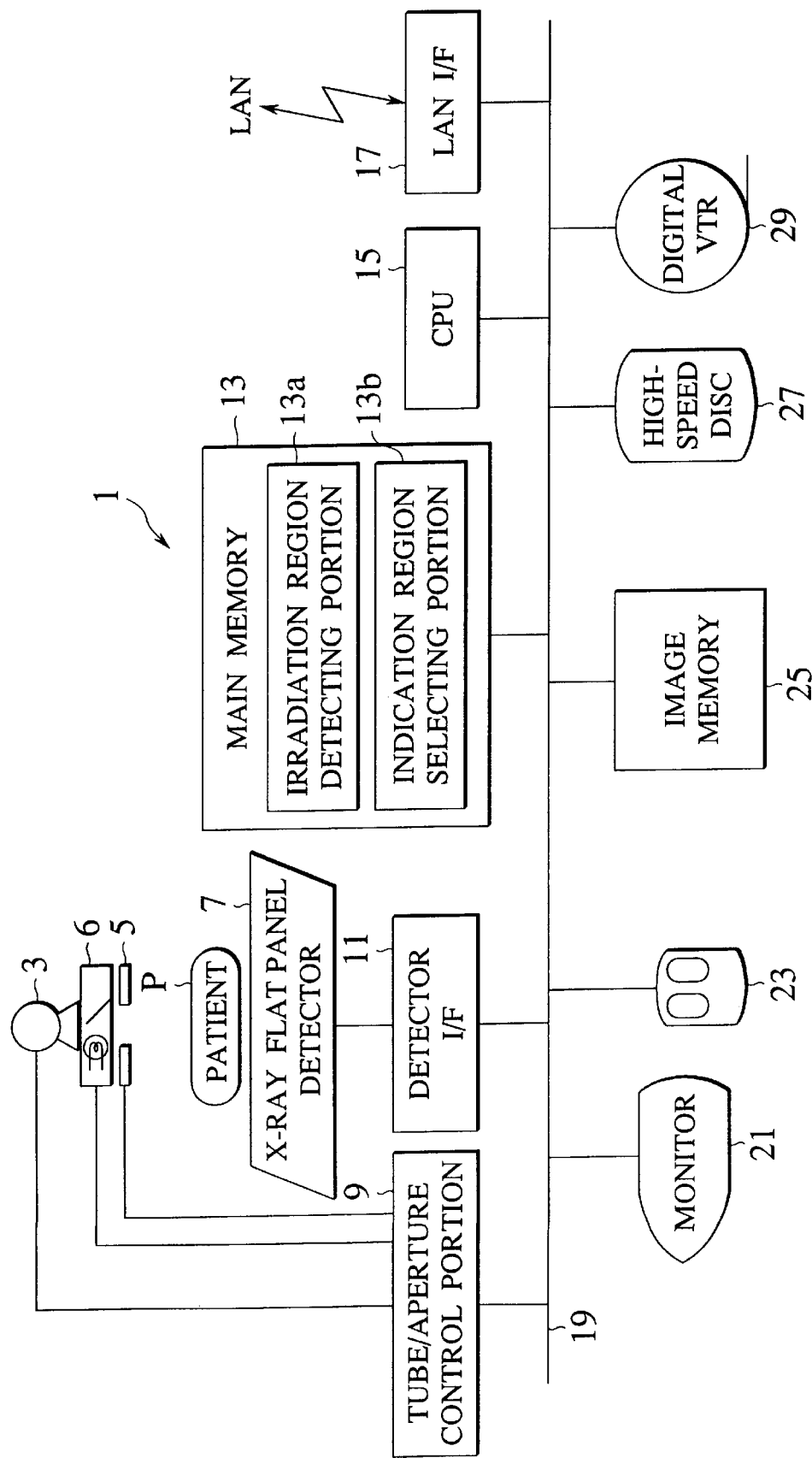

FIG.12A
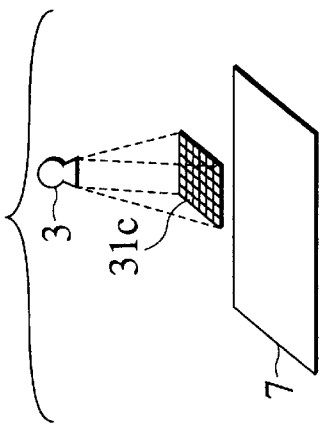
CASE WHERE ENTIRE IRRADIATION REGION IS DETECTED BY AN X-RAY FLAT PANEL DETECTOR
ALL-PIXEL DISPLAY MODE
IRRADIATION REGION DISPLAY MODE
PATIENT REGION DISPLAY MODE
FIG.12B
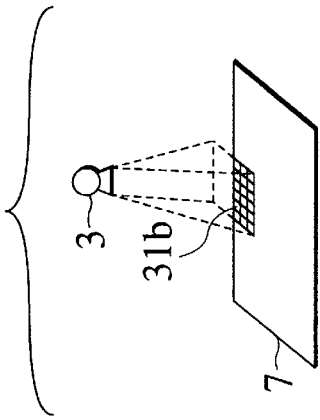
CASE WHERE ONLY PART OF THE IRRADIATION REGION IS DETECTED BY THE X-RAY FLAT PANEL DETECTOR
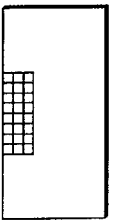
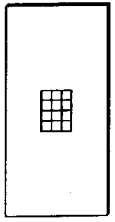
FIG.12C
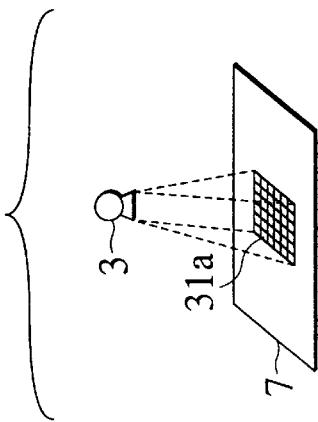
CASE WHERE NO IRRADIATION REGION IS DETECTED BY THE X-RAY FLAT PANEL DETECTOR
NO IMAGE
NO IMAGE
NO IMAGE IRRADIATION REGION 33a IRRADIATION REGION 33c

FIG.14A

ORIGINAL
IMAGE DATA

| $D_1$ | $D_2$ | $D_3$ | $D_4$ |
|---|---|---|---|
| $D_5$ | $D_6$ | $D_7$ | $D_8$ |
| $D_9$ | $D_{10}$ | $D_{11}$ | $D_{12}$ |
| $D_{13}$ | $D_{14}$ | $D_{15}$ | $D_{16}$ |

FIG.14B

DISPLAYED IMAGE
(EQUAL MAGNIFICATION)

| $D_1$ | $D_2$ | $D_3$ | $D_4$ |
|---|---|---|---|
| $D_5$ | $D_6$ | $D_7$ | $D_8$ |
| $D_9$ | $D_{10}$ | $D_{11}$ | $D_{12}$ |
| $D_{13}$ | $D_{14}$ | $D_{15}$ | $D_{16}$ |

FIG.14C

DISPLAYED IMAGE
(TWICE LONGITUDINALLY AND LATERALLY)

| $D_1$ | $D_1$ | $D_2$ | $D_2$ | $D_3$ | $D_3$ | $D_4$ | $D_4$ |
|---|---|---|---|---|---|---|---|
| $D_1$ | $D_1$ | $D_2$ | $D_2$ | $D_3$ | $D_3$ | $D_4$ | $D_4$ |
| $D_5$ | $D_5$ | $D_6$ | $D_6$ | $D_7$ | $D_7$ | $D_8$ | $D_8$ |
| $D_5$ | $D_5$ | $D_6$ | $D_6$ | $D_7$ | $D_7$ | $D_8$ | $D_8$ |
| $D_9$ | $D_9$ | $D_{10}$ | $D_{10}$ | $D_{11}$ | $D_{11}$ | $D_{12}$ | $D_{12}$ |
| $D_9$ | $D_9$ | $D_{10}$ | $D_{10}$ | $D_{11}$ | $D_{11}$ | $D_{12}$ | $D_{12}$ |
| $D_{13}$ | $D_{13}$ | $D_{14}$ | $D_{14}$ | $D_{15}$ | $D_{15}$ | $D_{16}$ | $D_{16}$ |
| $D_{13}$ | $D_{13}$ | $D_{14}$ | $D_{14}$ | $D_{15}$ | $D_{15}$ | $D_{16}$ | $D_{16}$ |

FIG.14D

DISPLAYED IMAGE
(1/2 TIMES LONGITUDINALLY AND LATERALLY)

| $\dfrac{D_1+D_2+D_5+D_6}{4}$ | $\dfrac{D_3+D_4+D_7+D_8}{4}$ |
|---|---|
| $\dfrac{D_9+D_{10}+D_{13}+D_{14}}{4}$ | $\dfrac{D_{11}+D_{12}+D_{15}+D_{16}}{4}$ |

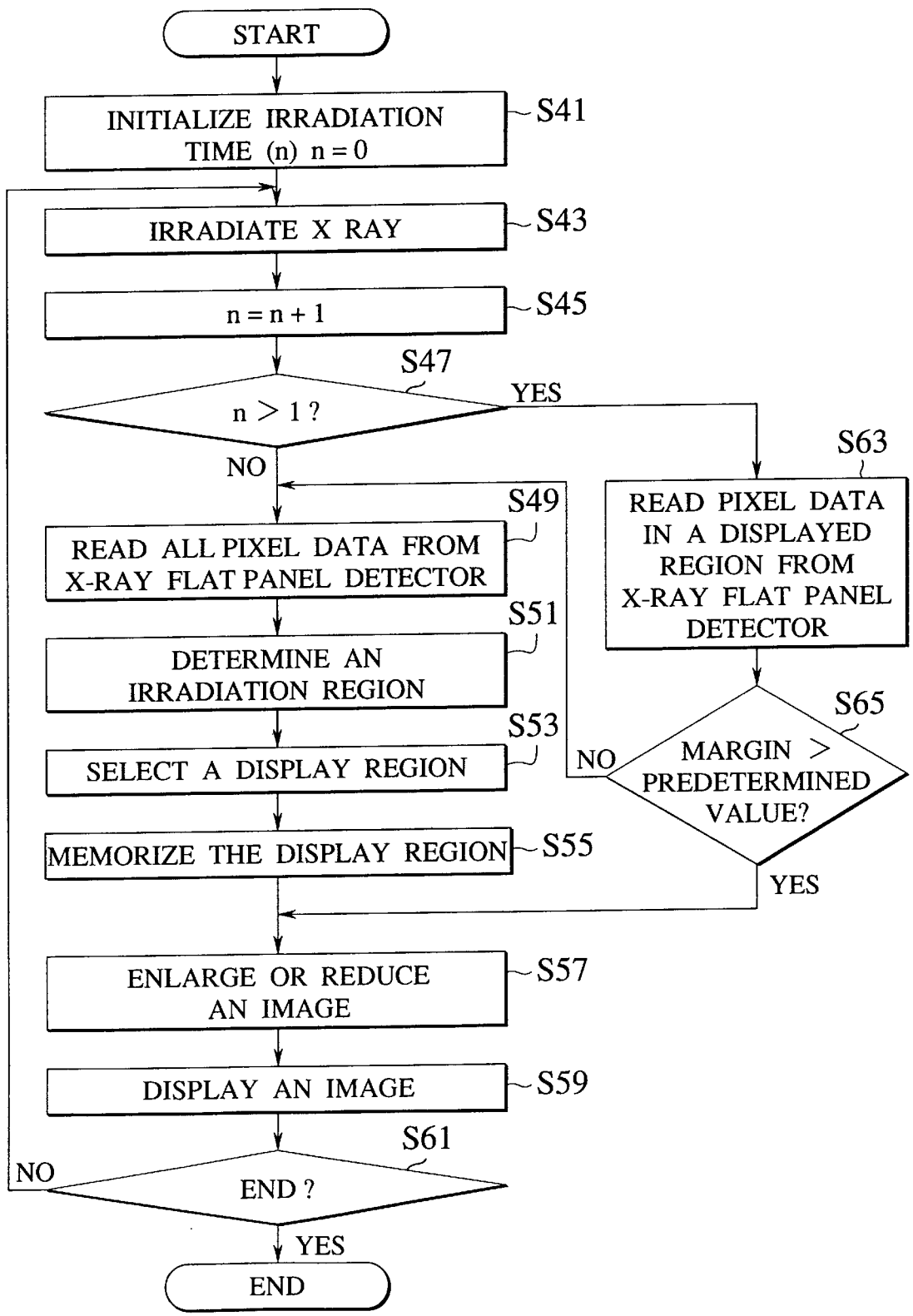

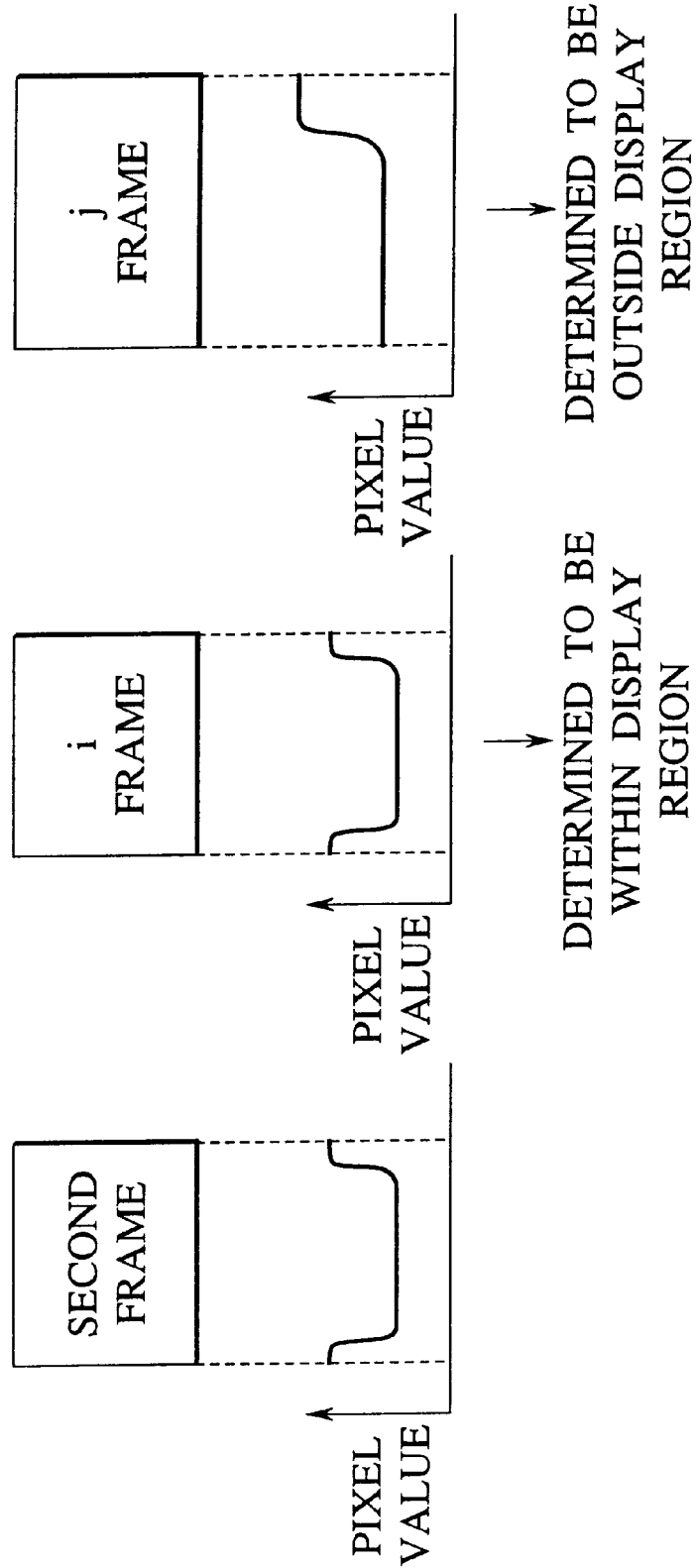

FIG.24
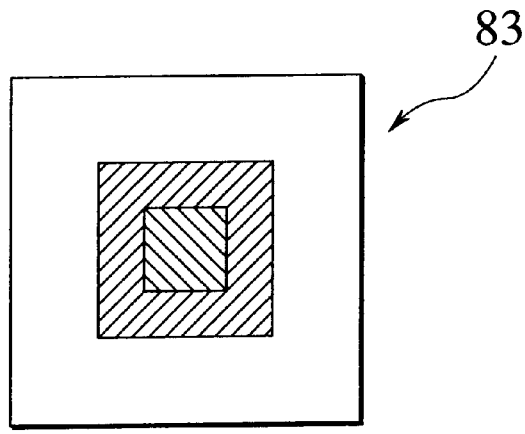
83
THE FIRST MODE IS SELECTED
IF THE BEAM IS LIMITED TO THE REGION 
THE SECOND MODE IS SELECTED
IF THE BEAM IS LIMITED TO THE REGION 
THE THIRD MODE IS SELECTED
IF THE BEAM IS LIMITED TO THE REGION 

X-RAY DIAGNOSTIC APPARATUS USING AN X-RAY FLAT PANEL DETECTOR AND METHOD FOR CONTROLLING THE X-RAY DIAGNOSTIC APPARATUS

BACKGROUND OF THE INVENTION

1. Field of the Invention

This invention relates to an X-ray diagnostic apparatus sing an X-ray flat panel detector and a method for controlling the same X-ray diagnostic apparatus.

2. Description of the Prior Art

In a field of X-ray image diagnosis, instead of radiography with conventional X-ray film, an image intensifier (I.I)-TV system has been widely used. The I.I-TV system has such advantages that X-ray image diagnosis can be performed immediately without a wait time for development unlike the silver salt film, real-time fluoroscopy as well as radiography can be carried out, and management, storage, transporting and copying of an image are facilitated by converting an image to digital data by video capture.

FIGS. 1A, 1B show a conventional X-ray diagnostic apparatus utilizing such an I.I-TV system.

In this X-ray diagnostic apparatus, X-ray is projected from an X-ray source 100 to a patient and an an X-ray image passing through the patient is intensified by I.I 101 and converted to an optical image. This optical image is taken by a TV camera 103 via an optical system 102 and subjected to a predetermined image processing by an image processing portion 104 and then supplied to a monitor device 105. As a result, the X-ray image can be observed via the monitor device 105.

In this X-ray diagnostic apparatus, magnification for the X-ray image is variable inside the I.I 101. If an entire X-ray image irradiated to an input surface of the I.I 101 is required to be observed, this entire X-ray image is focused on an output surface of the I.I 101 as an optical image by controlling an electronic lens provided inside the I.I 101. If part of the X-ray image irradiated to the input surface of the I.I 101 is required to be observed, this part of the X-ray image is focused on the output surface of the I.I 101 as an optical image by controlling the electronic lens as shown in FIG. 1B.

The X-ray diagnostic apparatus provided with the I.I 101 is capable of changing the magnification for the X-ray image by the electronic lens. Further, by narrowing an observation region for the X-ray image irradiated to the input surface of the I.I, a high resolution optical image can be obtained easily.

The size of the imaging region of the I.I-TV system is determined by a bore of the an I.I. Recently, I.I having a bore as large as 16" has been produced to meet a demand for enlargement of an imaging region. However, if the bore of the I.I is increased, a depth of its detecting system as well as the imaging region is increased, so that its weight also naturally increases. As a result, such an X-ray diagnostic apparatus becomes difficult to use. Further, the service life of the X-ray diagnostic apparatus is short because of tube structure.

Thus, an X-ray diagnostic apparatus utilizing a thin type X-ray flat panel detector has been regarded as a hopeful alternative to compensate for such disadvantages of the I.I-TV system.

The X-ray flat panel detector is capable of reading an X-ray strength distribution projected on a plane as data in each pixel. This X-ray flat panel detector is classified to two types. One is an indirect type in which the X-ray is converted to a light wavelength which can be detected by an photoelectric conversion element by using a fluorescent material, and the other one is a direct type in which the X-ray is directly detected by a semiconductor such as selenium. Both types of the X-ray flat panel detectors are produced by applying fine processing technology like semiconductor production technology, liquid crystal display panel production technology or the like and a panel of about 40 cm×40 cm can be produced now.

Recently, a case using the X-ray radiography to grasp a patient's condition has been increased in an emergency field such as an accident or disaster. In the conventional X-ray diagnostic apparatus, because its radiography region is relatively small, positioning for taking a region of interest within that radiography region must be achieved in even an emergency case or a number of radiographs must be taken to radiograph an entire field of the region of interest.

However, in case of the conventional X-ray diagnostic apparatus, if its X-ray source and X-ray detector are connected to each other in the system, detection of the position thereof and control of the position thereof must be carried out so as to place the X-ray detector at a position on which the X-ray is irradiated, so that labor and time are needed for this positioning.

Further in the conventional X-ray diagnostic apparatus, if the X-ray source and X-ray detector are not connected in the system, the position thereof must be determined by a number of pre-irradiation to place the detector at a position on which the X-ray is irradiated. Thus, in addition to the above problem, there is another problem that exposure to the X-ray is increased.

Further in a case of an X-ray diagnostic apparatus utilizing a large vision field X-ray flat panel detector, because entire pixel data of that X-ray detector are collected, it takes a long time to collect the data, and further it takes time and labor to extract and display data including an interest position from the collected data. That is, there is still another problem that high speed and detailed radiography is impossible.

From another point of view, the X-ray diagnostic apparatus is demanded to satisfy the following two points. One of them is ability to observe a wide region at a relatively low spatial resolution. The other is the ability to observe at a relatively high spatial resolution although the area is small. To satisfy these two requirements, an X-ray diagnostic flat panel detector having as high a spatial resolution as possible and as wide a vision field as possible is demanded to be produced.

However, if such an X-ray flat panel detector having the high spatial resolution and large vision field is used, data amount per frame output from the X-ray flat panel detector increases tremendously, thereby producing an inconvenience that its image processing circuit at a next step is burdened with a large load. Particularly, in case where X-ray consecutive image data (e.g., 30 frames/second) is collected, data transmission and processing at a very high data rate must be carried out, so that an expensive unit needs to be provided as a signal transmission system and signal processing system.

In a field of X-ray image diagnosis, angiography has been important for diagnosis on a circulatory organ such as the heart and blood vessel. According to this angiography, a tube called a catheter is inserted into a blood vessel up to near an object artery of a patient under fluoroscopy and then X-ray contrast medium is injected into the blood vessel through the catheter. The X-ray contrast medium flowing in the blood vessel is radiographed at a high speed with the X-ray diagnostic apparatus. As a result, the condition of the blood in the blood vessel is visualized.

Particularly, this inspection is carried out for diseases of the circulatory organ like myocardial infarction, cerebral infarction. Because the tube is inserted into the blood vessel, this inspection is conducted in a relatively clean inspection room. In this case, a patient lies on a diagnostic bed for the catheter and an operator and several assistants stand around him. A pair or two pairs of the X-ray sources and X-ray TV units (hereinafter referred to as X-ray TV chain) for obtaining X-ray images are placed just beside the patient (see FIG. 2).

In such an environment, a supporting device supporting the X-ray tube and X-ray TV unit is brought near to the patient as required from various angles like the head portion, leg, right hand side, left hand side to ensure a better access to the patient (see FIG. 3)

Conventionally, when the I.I.-TV camera is used as the X-ray TV system, even if the direction for approaching the I.I to the patient is changed, the X-ray image is obtained with a constant direction by turning the image by, for example, image processing because the image formed by the I.I.-TV system is circular.

However, in a case where the X-ray flat panel detector is used in the X-ray diagnostic apparatus, if the insertion direction of the supporting device to the patient is changed, the X-ray flat panel detector fixed on the supporting device is disposed in a different direction depending on the insertion direction relative to the patient.

Thus, if the X-ray detecting device is of rectangular shape, its corner moves relative to the patient corresponding to the direction of the supporting device. As a result, there occurs a problem that the patient feels a fear that that corner may strike him.

Further, in a case of radiographing the same portion, the direction of an image displayed on the monitor changes depending on a direction in which the X-ray—TV chain is brought to the patient.

Meanwhile, in conventional cardiac catheter inspection, generally, fluoroscopy by a bi-plane inspection unit is carried out because a complicated blood vessel system needs to be traced spatially.

In this bi-plane inspection unit, a C-arm holding device which is a floor placed type X-ray diagnostic apparatus (F: frontal holding device) and a Ω-arm holding device which is a mounting type (ceiling hoisting type) X-ray diagnostic apparatus (L: lateral holding device) are used at the same time and then fluoroscopy is achieved by irradiating a small mount of the X-ray continuously from each holding device to obtain an X-ray consecutive image. Consequently, fluoroscopy images of two directions are obtained at the same time.

FIG. 4 shows a schematic view on operation of the bi-planes in the conventional angiography and FIG. 5 shows fluoroscopy images of the frontal holding device and lateral holding device obtained by this bi-planes operation.

As for positioning for this angiography, the C-arm 201 of the frontal holding device (F) is set to RAO 30° and the Ω-arm 200 of the lateral holding device (L) is set to LAO 600.

Although a necessary vision field for the cardiac catheter inspection is 9 inch, intimate fluoroscopy at an enlargement mode of 6 inch is carried out by a vision field changing function of an image intensifier (I.I.). because a high quality X-ray image which enables to see blood vessel stricture or a tip of a fine catheter is demanded.

Because an entire cardiac blood vessel cannot be taken into a 6-inch vision field in the cardiac angiography using the frontal holding device (F) and lateral holding device (L), a table panel 202 on which a patient lies and two holding devices including the frontal (F) 201 and lateral (L) 200 are operated to trace a flow of contrast medium. Although FIG. 5 shows both the 9-inch vision field and 6-inch vision field, a fluoroscopy image which is actually displayed on the monitor is the 6-inch vision field fluoroscopy image.

In an operating procedure following a flow of the contrast medium in the vision field for fluoroscopy, the table panel 202 on which the patient lies is slid in the direction (to the right) indicated by the arrow A in FIG. 4 and the Ω-arm 200 of the lateral holding device (L) is moved in the direction (upward) indicated by the arrow B in the same figure. As a result, as shown in FIG. 5, the fluoroscopy image of the frontal holding device (F) is displayed such that an image in the center of the screen is slid to the left and the fluoroscopy image of the lateral holding device (L) is displayed such that an image in the center of the screen is slid to the right.

Next, the table panel 202 is slid in the direction (head direction) indicated by the arrow C of FIG. 4. Consequently, as shown in FIG. 5, as a fluoroscopy image of the frontal holding device (F), an end portion of the blood vessel which was out of the vision field is displayed by sliding the table panel 202. Then, as a fluoroscopy image of the lateral holding device (L), an end portion of the blood vessel which was out of the vision field is also displayed.

Each fluoroscopy image (DSA image) displayed on the monitor by such an operation is observed at real time to trace a flow of the contrast medium in the cardiac blood vessel.

However, in such a cardiac angiography, the table panel on which the patient lies and the two holding devices including the frontal holding device and lateral holding device must be operated to trace a flow of the contrast medium in the blood vessel. This operation is very complicated and requires a skill. Thus, it is very hard for a single operator to operate the frontal holding device and lateral holding device in two directions in a combined manner. Therefore, conventionally, there exists a problem that specialized operators (totally two operators) are required to operate the frontal holding device and lateral holding device.

SUMMARY OF THE INVENTION

In view of the above problems, an object of the present invention is to provide an X-ray diagnostic apparatus which can be used near a diagnostic bed, particularly in an emergency, not requiring any troublesome setting, capable of obtaining an X-ray image instantaneously and easily, and further capable of achieving both radiography and fluoroscopy.

Another object of the invention is to provide an X-ray diagnostic apparatus using a large vision field, high resolution X-ray flat panel detector, capable of carrying out image processing flexibly by changing resolution corresponding to the size of an observation region relative to the X-ray flat panel detector.

Still another object of the invention is to provide an X-ray diagnostic apparatus using the X-ray flat panel detector, in which even if its X-ray detecting system is inserted in any direction relative to the patient, he or she is never made to feel uneasiness and an observed image is always directed in a constant direction.

A further object of the invention is to provide an X-ray diagnostic apparatus having an excellent operability, which enables even an operator to operate well enough following a flow or the like of contrast medium.

To achieve the above objects, there is provided an X-ray diagnostic apparatus comprising: an X-ray source for irradiating X-ray; a flat panel detector for detecting the X-ray irradiated from the X-ray source; and a collection processing means for collecting and processing pixel data of any region detected by the flat panel detector.

According to a preferred embodiment of the invention, the collection processing means collects pixel data corresponding to an X-ray irradiation region determined based on, at least, a degree of opening of a beam limiting device of the X-ray source and a distance between the X-ray source and the flat panel detector.

According to a preferred embodiment of the invention, the collection processing means sweeps out pixel data corresponding to a region other than the X-ray irradiation region in the flat panel detector in batch when it collects pixel data corresponding to the X-ray irradiation region.

According to a preferred embodiment of the invention, a patient region determining means for determining and extracting pixel data corresponding to the patient from pixel data corresponding to the X-ray irradiation region is further included.

According to a preferred embodiment of the invention, a display means for displaying an image based on pixel data corresponding to the X-ray irradiation region or the patient region and a display control means for enlarging or reducing an image based on pixel data corresponding to the X-ray irradiation region or pixel data corresponding to the patient region, depending on a screen size of the display means, are further included.

To achieve the above objects, there is provided an X-ray diagnostic apparatus comprising: an X-ray source for irradiating X-ray; a flat panel detector for detecting the X-ray irradiated from the X-ray source; an irradiation region detecting means for detecting an X-ray irradiation region based on pixel data from the flat panel detector; a patient region detecting means for detecting a patient region from the X-ray irradiation region;

a display means; a setting means for setting all-pixel display mode, irradiation region display mode or patient region display mode; and a display control means for controlling so as to display an image based on all pixel data on the display means when the all-pixel display mode is set, an image based on pixel data corresponding to the X-ray irradiation region on the display means when the irradiation region display mode is set or an image based on pixel data corresponding to the patient region on the display means when the patient region display mode is set.

Further, to achieve the above objects, there is provided a control method for an X-ray diagnostic apparatus comprising an X-ray source for irradiating X-ray to a patient and a flat panel detector for detecting the X-ray irradiated from the X-ray source, the control method comprising: conducting a first irradiation of the X-ray from the X-ray source; reading pixel data from the flat panel detector; detecting a region irradiated with the X-ray on the flat panel detector based on read pixel data; selecting a region whose pixel data should be collected from the flat panel detector based on a result of that detection; memorizing information of a region whose image data should be collected;

conducting a second irradiation of the X-ray from the X-ray source; and reading pixel data from the flat panel detector based on the memorized region information.

Further, to achieve the above objects, there is provided a control method for an X-ray diagnostic apparatus comprising an X-ray source for irradiating X-ray to a patient and a flat panel detector for detecting the X-ray irradiated from the X-ray source, the control method comprising: conducting a first irradiation of the X-ray from the X-ray source; reading pixel data from the flat panel detector; detecting a region where a patient exists on the flat panel detector based on the read pixel data; selecting a region whose pixel data should be collected from the flat panel detector based on a result of that detection; memorizing information of the region whose image data should be collected;

conducting a second irradiation of the X-ray from the X-ray source; and reading pixel data from the flat panel detector based on the memorized region information.

Further, to achieve the above objects, there is provided an X-ray diagnostic apparatus comprising: an X-ray source for irradiating the X-ray; an X-ray beam limiting device for limiting an X-ray irradiation region; an opening degree setting means for setting a degree of opening of the X-ray beam limiting device;

a flat panel detector for detecting the X-ray irradiated from the X-ray source via the X-ray beam limiting device; an image processing means for receiving and processing pixel data detected by the flat panel detector;

and a control means for controlling the flat panel detector so as to compile adjacent pixel data from the flat panel detector as a single value, depending on the size of an irradiation region relative to the flat panel detector, determined by the opening degree setting means and a processing resolution of the image processing means and then input this value into the image processing means.

According to a preferred embodiment of the invention, when a resolution of pixel on the flat panel detector corresponding the size of the irradiation region is higher than the processing resolution of the image processing means, the control means controls the flat panel detector so as to compile adjacent pixel data to a single value and input this value into the image processing means, and when the resolution is lower than the processing resolution of the image processing means, it controls the flat panel detector so as to input the pixel data corresponding to the processing resolution of the image processing means into the image processing means as it is.

According to a preferred embodiment of the invention, the flat panel detector includes: a plurality of X-ray electric charge converting means disposed in matrix for generating electric charge corresponding to an amount of the impinging X-ray; a plurality of accumulating means for accumulating the electric charge generated from the plurality of the X-ray—electric charge converting means in each thereof; a plurality of switching elements each electrically connected to the plurality of the accumulating means; a scanning line driving means for controlling the plurality of the switching elements in the unit of row; a plurality of signal lines connected to an output side of the plurality of the switching elements for each line; and a selectively reading means for selectively reading signals on the signal lines, the control means controlling the scanning line driving means so that plural adjacent switching elements are turned ON at the same time.

According to a preferred embodiment of the invention, the control means controls the selectively reading means so that plural rows of the signal lines are get into reading condition.

According to a preferred embodiment of the invention, an irradiation position setting means for setting the X-ray irradiation position relative to the flat panel detector is further included.

To achieve the above objects, there is provided an X-ray diagnostic apparatus comprising: an X-ray source for irradiating the X-ray; an X-ray beam limiting device for limiting an X-ray irradiation region; an opening degree setting means for setting a degree of opening of the X-ray beam limiting device; a flat panel detector for detecting the X-ray irradiated from the X-ray source via the X-ray beam limiting device; a region setting means for setting the size of a region in the flat panel detector, whose pixel data should be read; an image processing means for receiving and processing pixel data detected by the flat panel detector; and a control means for controlling the flat panel detector so as to compile adjacent pixel data from the flat panel detector as a single value, depending on the size of an irradiation region relative to the flat panel detector, determined by the opening degree setting means, a processing resolution of the image processing means and a size of a region set by the region setting means and then input this value into the image processing means.

To achieve the above objects, there is provided an X-ray diagnostic apparatus comprising: an X-ray source for irradiating the X-ray; first and second X-ray beam limiting devices for limiting the X-ray irradiation region; an opening degree setting means for setting the degree of opening of the first X-ray beam limiting device; a flat panel detector for detecting the X-ray irradiated from the X-ray source via the first and second X-ray beam limiting devices; a region setting means for setting the size of a region in the flat panel detector, whose pixel data should be read and then setting a degree of opening of the second X-ray beam limiting device based on the size of the set region; an image processing means for receiving and processing pixel data detected by the flat panel detector and control means for controlling the flat panel detector so as to compile adjacent pixel data of the flat panel detector to a single value depending on the size of an irradiation region relative to the flat panel detector, determined by the opening degree setting means and the region setting means and then input this value to the image processing means.

To achieve the above objects, there is provided an X-ray diagnostic apparatus comprising: an X-ray source for irradiating the X-ray; an X-ray beam limiting device for limiting an X-ray irradiation region; an opening degree setting means for setting a degree of opening of the X-ray beam limiting device; a flat panel detector for detecting the X-ray irradiated from the X-ray source via the X-ray beam limiting device, the flat panel detector having high resolution detecting elements in the center thereof and low resolution detecting elements in a peripheral portion thereof; an image processing means for receiving and processing pixel data detected by the flat panel detector; and a control means for controlling the flat panel detector so that if the size of an irradiation region relative to the flat panel detector determined by the opening degree setting means is smaller than the size of the low resolution detecting element, pixel data detected by the high resolution detecting element is input to the image processing means as it is and if the size of the irradiation region relative to the flat panel detector determined by the opening degree setting means is larger than the size of the low resolution detecting element, the pixel data detected by the low resolution detecting element and the pixel data detected by the high resolution detecting element are compiled in the unit of adjacent data and input to the image processing means.

To achieve the above objects, there is provided an X-ray diagnostic apparatus comprising: an X-ray source for irradiating the X-ray; a flat panel detector for detecting the X-ray irradiated from the X-ray source; an operating means for operating to move a region in the flat panel detector whose pixel data should be read at real time; and a control means for controlling to read the pixel data in the region moved by the operating means from the flat panel detector.

According to a preferred embodiment of the invention, frontal X-ray source and lateral X-ray source; frontal flat panel detector and lateral flat panel detector; frontal operating means and lateral operating means and frontal operating means and lateral operating means are further comprised and the control means reads pixel data in a region moved by the frontal operating means from the frontal flat panel detector and further reads pixel data moved by the lateral operating means from the lateral flat panel detector.

According to a preferred embodiment of the invention, if one of the frontal operating means and the lateral operating means is operated, the control means controls to read pixel data in a region moved by the operated operating means from a corresponding flat panel detector and, while determining that the other operating means moves interlockingly with the operated operating means, controls to read pixel data from a corresponding flat panel detector To achieve the above objects, there is provided X-ray diagnostic apparatus comprising: an X-ray source for irradiating X-ray; a flat panel detector for detecting the X-ray irradiated from an X-ray source; a memorizing means for memorizing a moving pattern of a region in the flat panel detector whose pixel data should be read; and a control means for controlling to read the pixel data from the flat panel detector according to the moving pattern memorized in the memorizing means.

To achieve the above objects, there is provided an X-ray diagnostic apparatus comprising: an X-ray source for irradiating X-ray; a flat panel detector for detecting the X-ray irradiated from an X-ray source; a reading region determining means for, in a condition that the region of the flat panel detector is divided to plural regions, determining a region to be moved to read its pixel data by detecting changes in the pixel data value among the respective regions and a control means for controlling so as to read pixel data from the flat panel detector based on a result of a determination of the reading region determining means.

To achieve the above object, there is provided an X-ray diagnostic apparatus comprising: an X-ray source for irradiating X-ray; a flat panel detector for detecting the X-ray irradiated from an X-ray source; a holding means rotatable relative to a patient, holding the flat panel detector and the X-ray source such that they oppose each other and further holding the flat panel detector such that it is rotatable; and a control means for detecting a rotation angle of the holding means relative to the patient and controlling an angle of the flat panel detector relative to the holding means so that the angle of the flat panel detector relative to the patient is constant.

The nature, principle and utility of the invention will become more apparent from the following detailed description when read in conjunction with the accompanying drawings.

BRIEF DESCRIPTION OF THE DRAWINGS

In the accompanying drawings:

FIGS. 1A, 1B are block diagrams showing a conventional X-ray diagnostic apparatus using an image intensifier as a radiography means;

FIG. 6 is a block diagram showing a structure of an X-ray diagnostic apparatus of the present invention;

FIGS. 12A–12C are diagrams for explaining a relation in position between an X-ray irradiation region and an X-ray flat panel detector and a display on a monitor;

FIGS. 14A–14D are diagrams showing examples of indication of a display region on the monitor;

FIG. 15 is a flow chart for explaining an example of a case for increasing a speed for reading pixel data produced by a following X-ray irradiation, with reference to a display region produced by a preceding X-ray irradiation according to a second embodiment;

FIGS. 18A–18C are diagrams showing a case for determining whether or not the pixel data reading region of the following X-ray irradiation is within a margin area;

FIG. 24 is a diagram for explaining the reading control at the first-third mode carried out by the X-ray diagnostic apparatus of the fifth embodiment;

DESCRIPTION OF THE PREFERRED EMBODIMENTS

Figure 2:
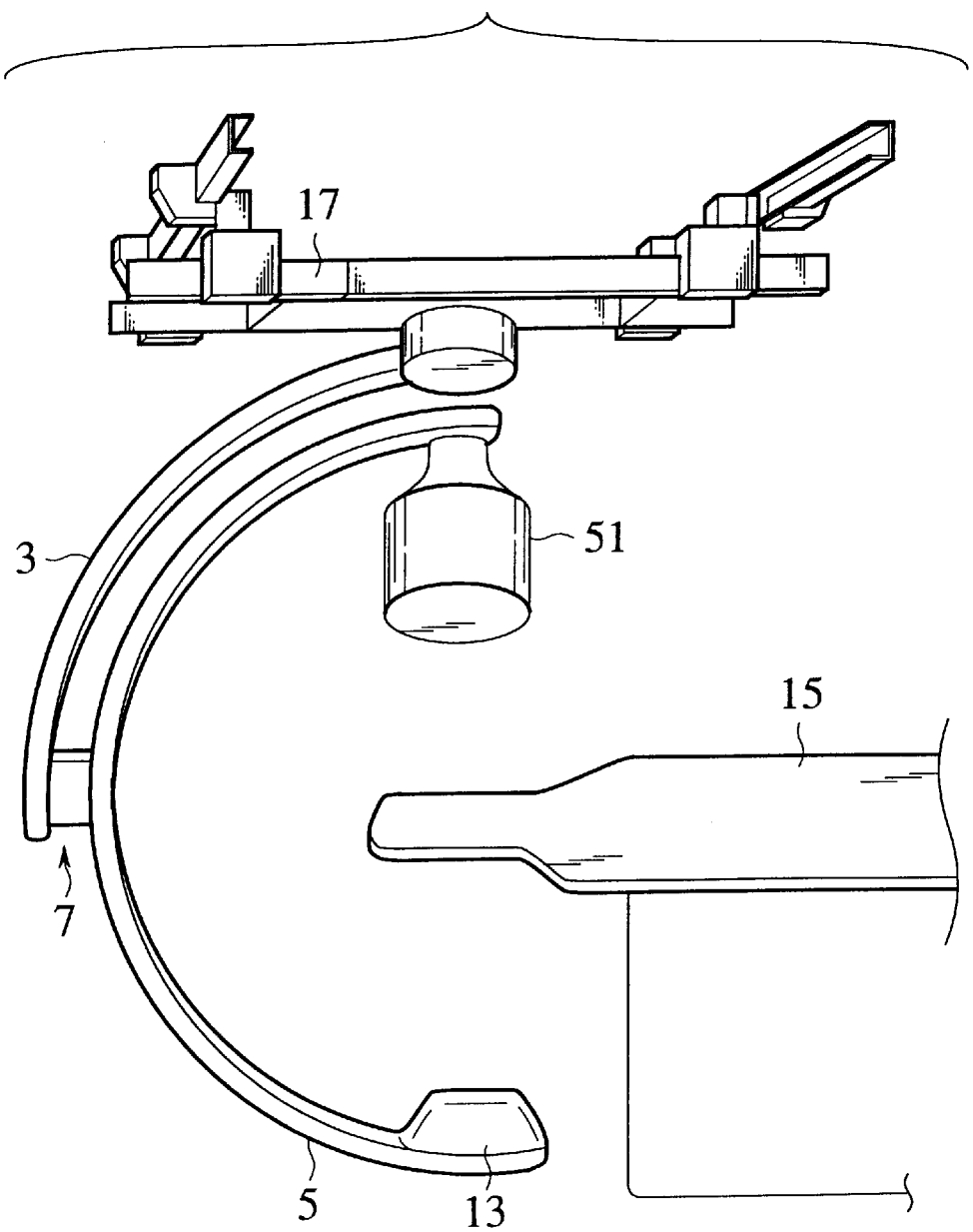
FIG. 2 is a construction diagram showing a conventional I.I-TV system.
Figure 3:
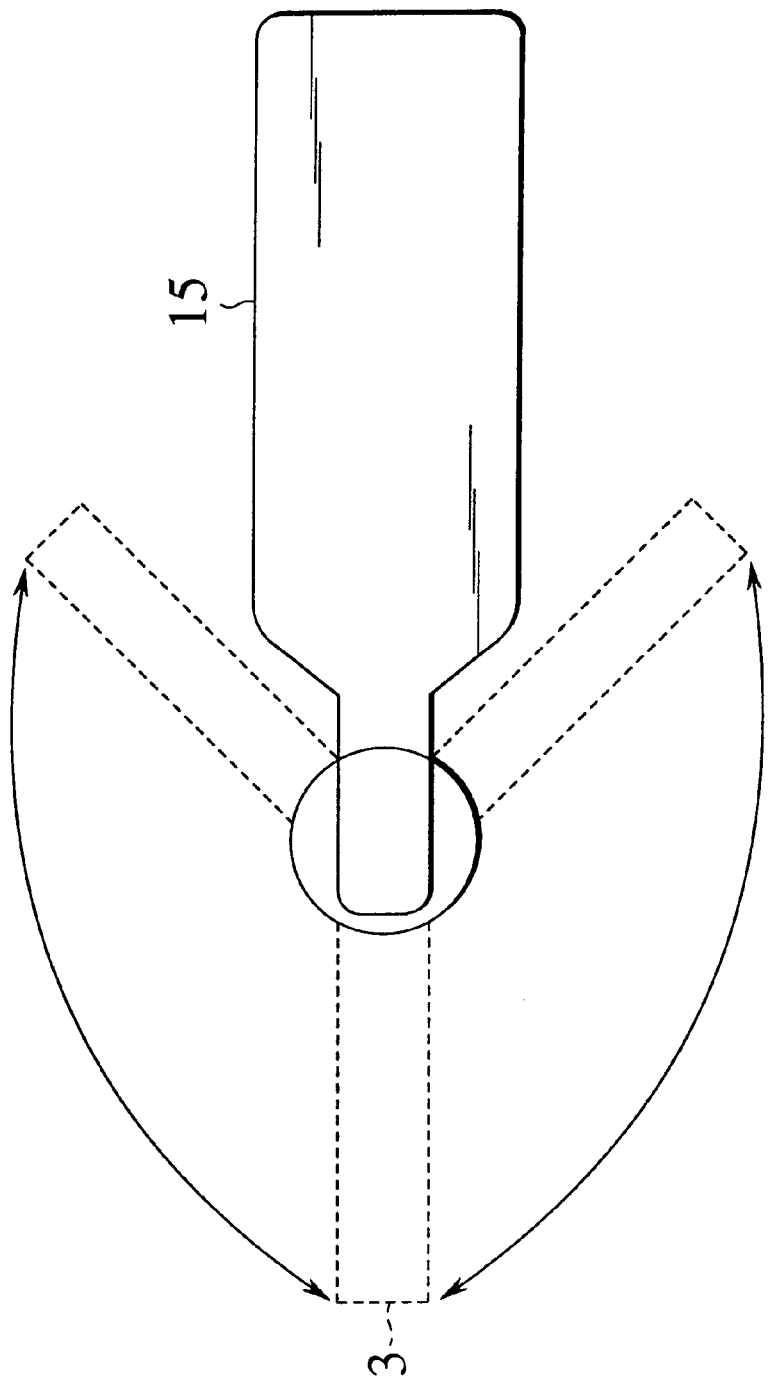
FIG. 3 is a plan view showing examples of arm insertion direction in the conventional I.I-TV system.
Figure 4:
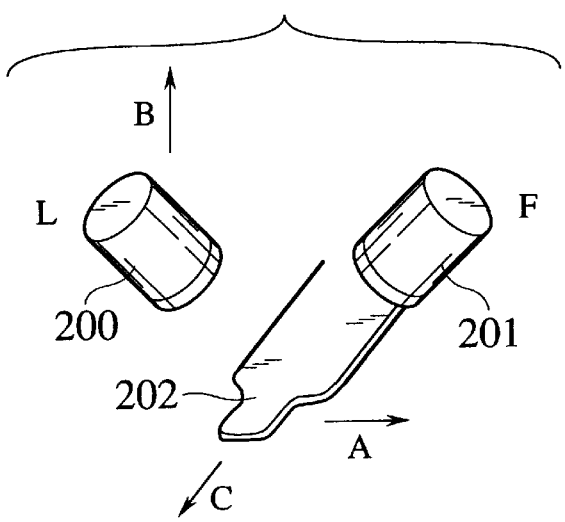
FIG. 4 is a diagram for explaining an operation of bi-planes with a conventional lateral holding device and frontal holding device in cardiac angiography.
Figure 5:
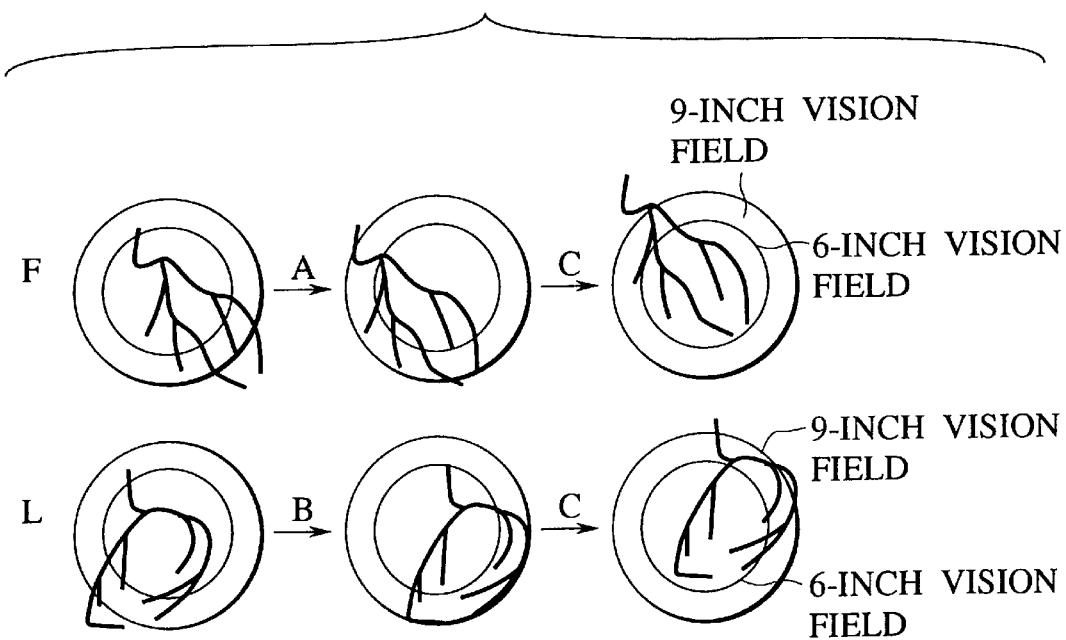
FIG. 5 is a view showing a fluoroscopy image obtained by the conventional bi-plane operation.

Hereinafter, the embodiments of the present invention will be described in detail with reference to the accompanying drawings.

FIG. 6 is a block diagram showing a structure of a first embodiment of an X-ray diagnostic apparatus according to the present invention.

Referring to the same FIG. 6, the X-ray diagnostic apparatus 1 comprises an X-ray tube 3 for irradiating X-ray to a patient P, an X-ray beam limiting device 5, an irradiation region indicating device 6 for irradiating a guide beam to a scheduled position on which the X-ray is intended to be projected of the patient P, an X-ray flat panel detector 7 for detecting the X-ray, a tube/aperture control portion 9 for controlling irradiation from the X-ray tube 3 and the beam limiting device 5, a detector I/F 11, a main memory 13, a CPU 15, LAN,I/F 17 for connecting the X-ray diagnostic apparatus 1 to an outside medical image observing apparatus, medical database and the like, a bus 19, a monitor 21 for displaying the X-ray image and control screen, a mouse 23 as an input means for inputting control information, an image memory 25, a high-speed disc 27 for storing still images, animation pictures and control programs and a digital VTR 29 for recording and playing back the animation pictures.

The X-ray flat panel detector 7 has a radiography region 1, of, for example, 40 cm×40 cm and is mounted below a panel (not shown) on which the patient P is to be placed.

Figure 7A:
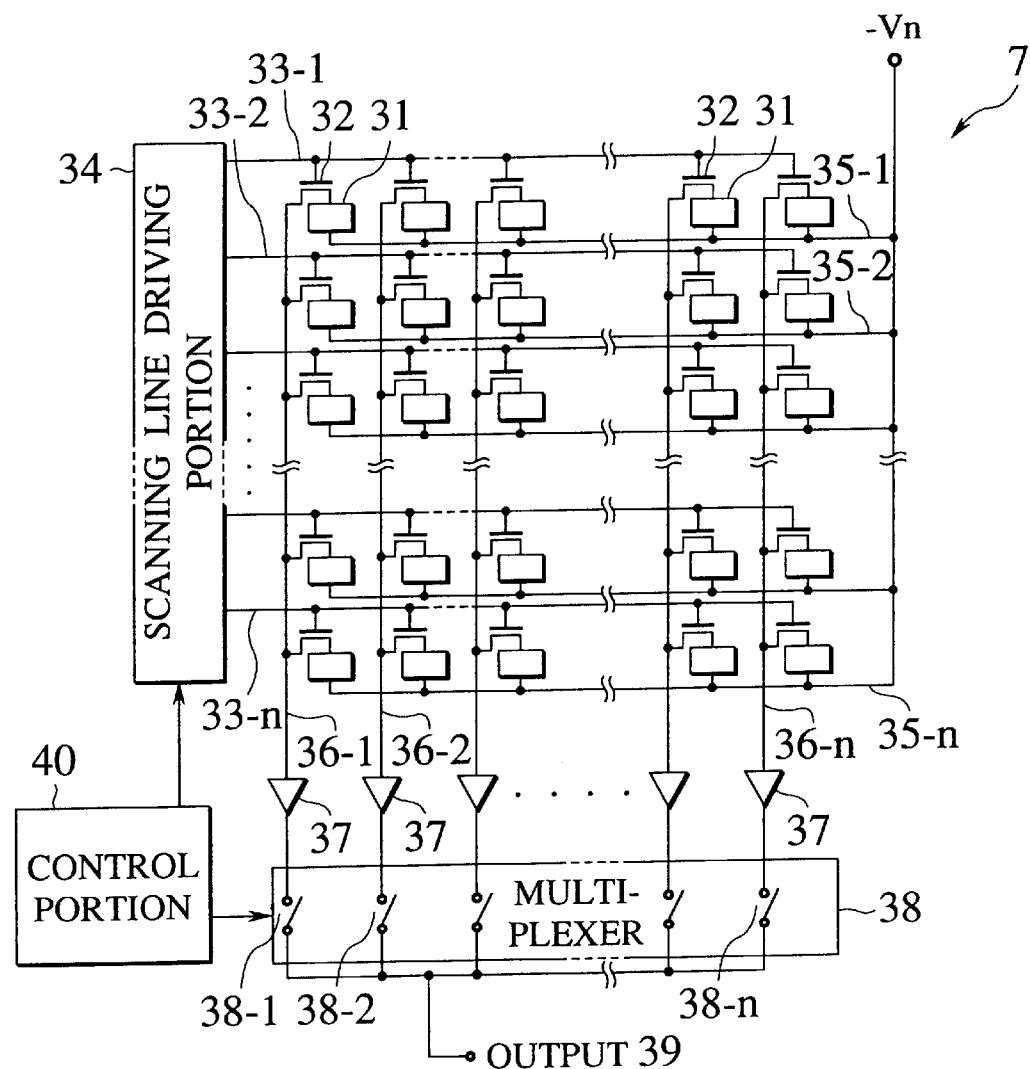
FIGS. 7A, 7B are diagrams showing a structure of an X-ray flat panel detector.

The X-ray flat panel detector 7 is, for example, an indirect conversion type X-ray flat panel detector for detecting an X-ray image by converting it to an optical image. Concretely speaking, the X-ray flat panel detector 7 comprises X-ray detecting elements each comprising a pixel 31 and TFT 32, arranged two-dimensionally in the form of an array as shown in FIG. 7A. Although in the above example, the X-ray flat panel detector is an indirect conversion type X-ray flat panel detector, it is permissible to use another detection method X-ray flat panel detector such as a direct conversion type X-ray flat panel detector in which the X-ray is caught by photoconductive material layer and directly converted to electric charges.

That is, the X-ray flat panel detector 7 comprises fluorescent material for converting the X-ray image to a visible optical image (visible light), a plurality of pixels 31 for sensing this visible light to form an electric charge corresponding to the incident light quantity, and a plurality of thin film transistors (TFT) 32 for use as a switch for reading the electric charge accumulated in these pixels 31.

Figure 7B:
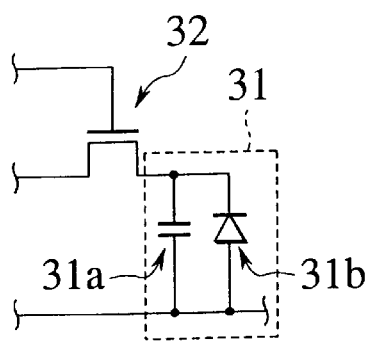

As shown in FIG. 7B, each pixel 31 is constituted of a photo diode 31b for sensing visible light so as to form an electric charge corresponding to the incident light quantity and a capacitor (accumulative capacitor) 31a for accumulating the electric charge formed by this photo diode 31b.

A junction point between a cathode of the photo diode 31b and a terminal of the accumulative capacitor 31a is connected to inverse bias power source (−Vn) via power line 35 (35-1, 35-2, . . . 35-n) shown in FIG. 7B and a junction point between an anode of the photo diode 31b and the other terminal of the accumulative capacitor 31a is connected to a source terminal of the TFT 32.

Each gate terminal of the TFT 32 is connected to a common scanning line 33 (33-1, 33-2, . . . 33-n) in each row and each scanning line is connected to each scanning line terminal of a scanning line driving portion 34. Each drain terminal of the TFT 32 is connected to a common signal line 36 (36-1, 36-2, . . . 36-n) in each column and each signal line is connected to each switch 38-1, 38-2, . . . 38-n of a multiplexer 38 via a readout amplifier 37.

Figure 8:
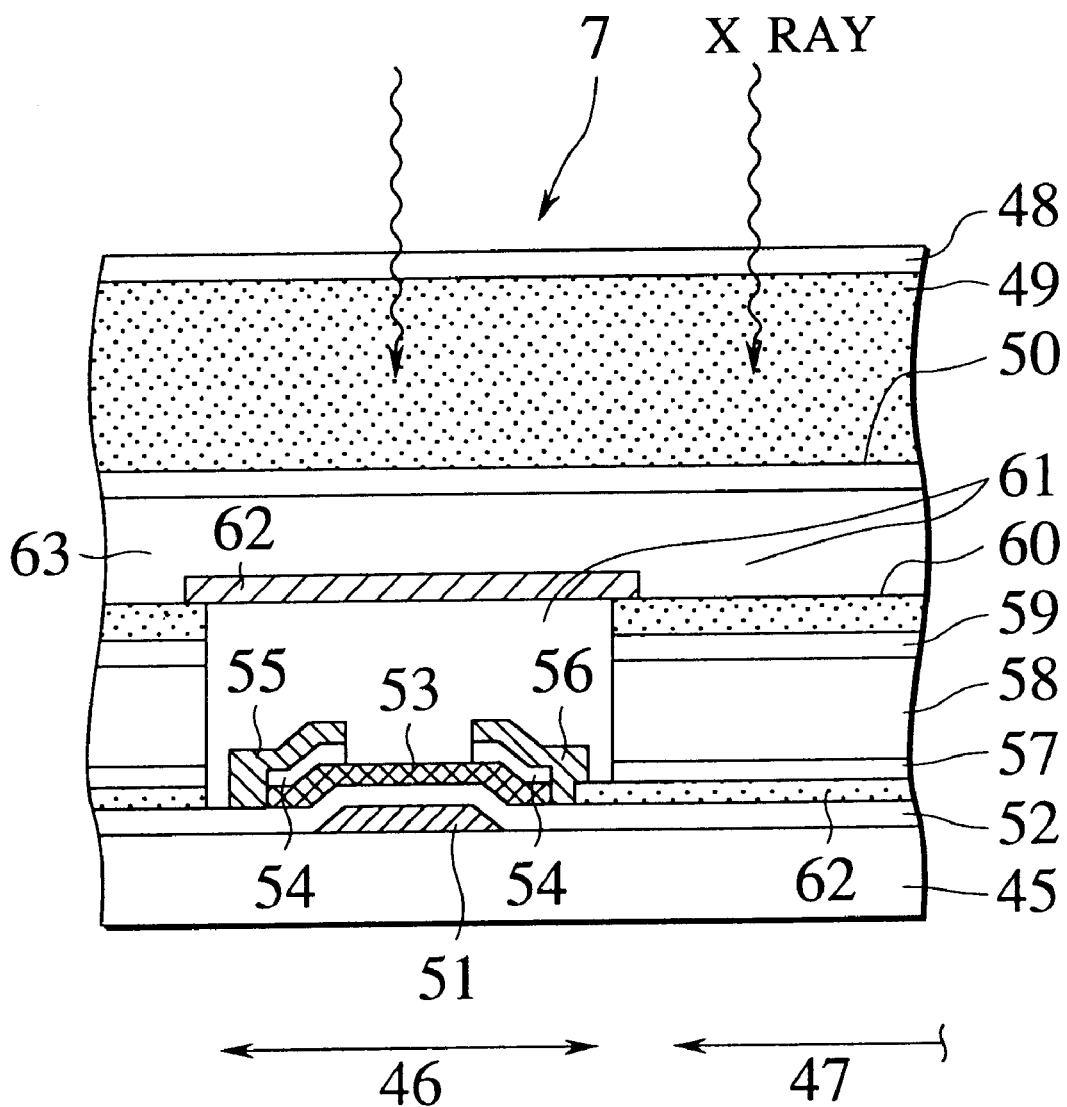
FIG. 8 is a sectional view of the X-ray flat panel detector.

If explaining about the X-ray detecting element comprising the pixel 31 and TFT 32 further in detail, as shown in FIG. 8, a gate electrode 51 is formed in a TFT region 46 on a supporting material 45 and SiNx layer 52 is formed thereon. Further, i type amorphous silicone layer (i type a-si layer) 53 is formed on the SiNx layer 52 in the TFT region 46. Then, a drain electrode 55 and a source electrode 56 are formed on the amorphous silicone layer 53 via n$^+$a-Si layer 54 so as to form the TFT 32.

Then, n$^+$a-Si layer 62 is formed in PD region 47 on the supporting material 45 such that it is connected to the SiNx layer 52 and source electrode 56. n$^+$a-Si layer 57, ia-Si layer 58 and p$^+$a-Si layer 59 are formed in succession and thereby a pin-structure photo diode 31b is formed.

A first polyimide resin layer 61 is formed on the TFT 32 and a transparent electrode 60 is formed on the photo diode 31b. A metal electrode 62 for connecting the transparent electrodes 60 of photo diodes 31b is formed on the first polyimide resin layer 61.

Then, a second polyimide resin layer 63 is formed on the transparent electrode 60 and metal electrode 62. A transparent protective film 50, fluorescent material 49 and light reflective layer 48 are formed in succession on the second polyimide resin layer 63.

In the X-ray flat panel detector 7 having such a structure, if an X-ray beam passing through a patient impinges, visible light is reflected by the light reflective layer 48 and only the X-ray passes through the light reflective layer 48 and enters the fluorescent material 49. Energy of this incident X-ray is converted to light energy (visible light) by the fluorescent material 49 and this visible light passes through the transparent protective film 50 and second polyimide resin layer 63 and further is received by the photo diode 31b more sensitive to the visible light via the transparent electrode 60.

This photo diode 31b forms an electric charge proportional to light energy and supplies this to the aforementioned accumulative capacitor 31a. The electric charge accumulated in the accumulative capacitor 31a is read out as an image signal of each pixel in each line. Because this read out image signal is proportional to the energy of the X-ray, this image signal is supplied to the CPU 15 through the multiplexer 38 and subjected to video process or the like, and then supplied to the monitor 21 so as to obtain an X-ray picture.

The main memory 13 stores a control program for the X-ray diagnostic apparatus 1 which is read out from the high-speed disc 27 and this control program contains an irradiation region detecting portion 13a and an indication region selecting portion 13b.

When X-ray radiography or fluoroscopy is carried out with the X-ray diagnostic apparatus 1 according to this embodiment, the position of the X-ray tube 3 and a degree of opening of the X-ray beam limiting device are adjusted while observing a guide beam projected from the irradiation region indicating device 6 onto the patient P so as to set an X-ray irradiation region. Then, a control screen is displayed on the monitor 21 and an icon on the control screen is specified with the mouse 23 so as to set radiography conditions including tube voltage, tube current, irradiation time and the like. Particularly in a case when radiography is requested urgently, it is possible to set radiography conditions by selecting any appropriate condition from plural predetermined standard radiography conditions.

Figure 9:
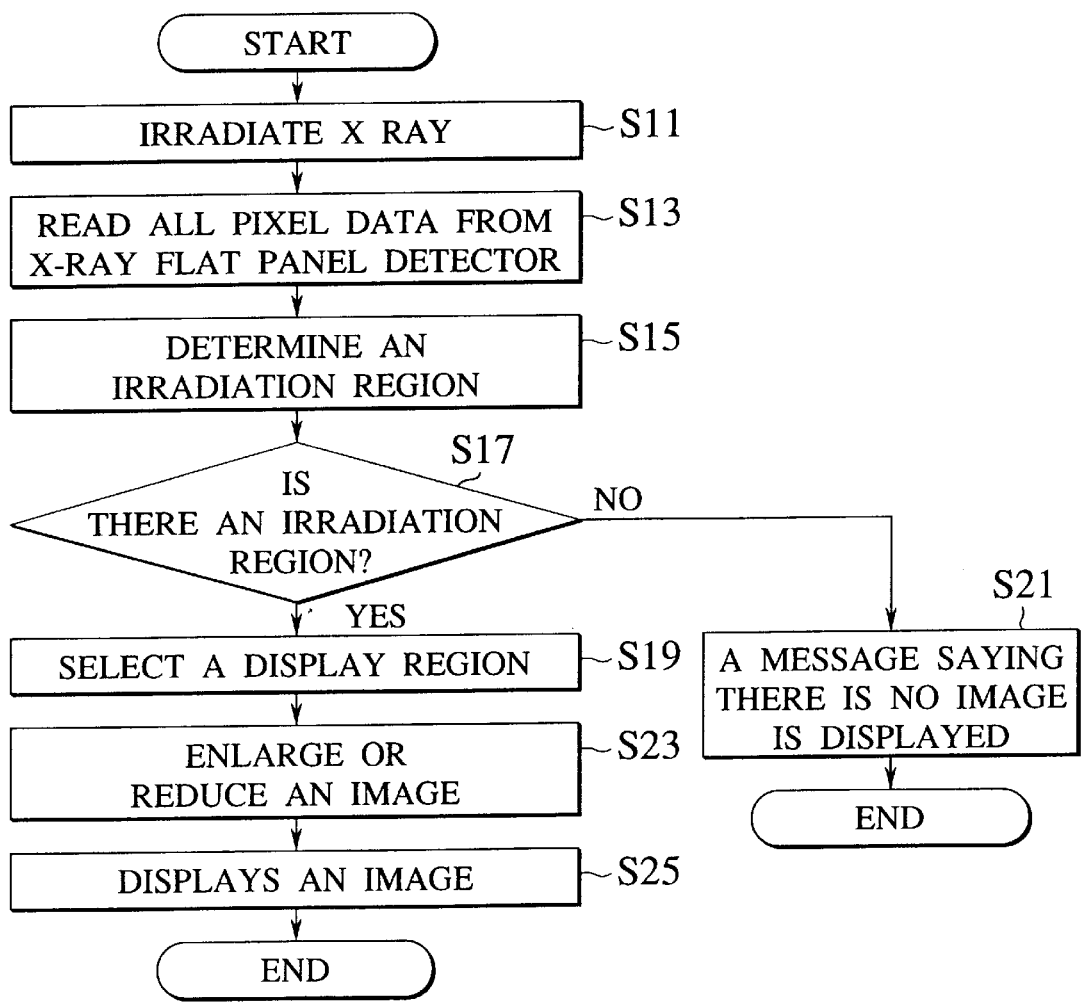
FIG. 9 is a flow chart for explaining an operation of a first embodiment.

Next, when the X-ray irradiation is instructed from the control screen of the monitor 21, the CPU 15 resets the X-ray flat panel detector 7 through the detector I/F 11 so as to return the amount of the electric charge accumulated in each pixel to a predetermined quantity, and then permits the X-ray tube 3 to project the X-ray beam through the tube/aperture control portion 9 (step S11) (see FIG. 9). If an irradiation time set in the radiography condition is terminated, the irradiation from the X-ray tube 3 is finished.

A high voltage for irradiation of the X-ray beam is supplied from a high voltage generator (not shown) to the X-ray tube 3 and the voltage, current and supply time of this high voltage power supplied to the X-ray tube 3 from the high voltage generator are controlled by control of the tube/aperture control portion 9. The detector I/F 11 and tube/aperture control portion 9 may be connected with cable or radio.

After the termination of the X-ray beam, an electric charge is generated in a pixel exposed to the X-ray of the X-ray flat panel detector 7. A signal corresponding to an electric charge generated in each of all the pixels is read out, A/D converted and stored in the image memory 25 (step S13).

Then, the irradiation region detecting portion 13a determines a region to which the X-ray is projected of the X-ray flat panel detector 7 with reference to the pixel values stored in the image memory 25 (step S15). The method for determination will be described later. If there is found no irradiation region in this determination, a message saying that there is no image is displayed (step S21) and the processing is terminated.

If the position and size of a region to be irradiated is determined, the indication region selecting portion 13b determines a region to be displayed (step S19), enlarges or reduces an image corresponding to this region corresponding to the monitor screen (step S23) and displays this image on the monitor 21 (step S25). The indication region selecting portion 13b has an all-pixel display mode, an irradiation region display mode, and a patient region display mode, which are to be selected by operating the control panel.

If the all-pixel display mode is selected, an entire irradiation surface of the X-ray flat panel detector 7 is displayed on the monitor screen. If the irradiation region display mode is selected, a region to which the X-ray is projected of the X-ray flat panel detector 7 plus an appropriate margin is determined as the display region and displayed on the monitor screen. If the patient region display mode is selected, a region in which an image of the patient is received on the X-ray flat panel detector 7 plus an appropriate margin is determined as the display region and displayed on the monitor screen.

Preferably the display region should be made to coincide with the shape of the X-ray beam limiting device 5 and usually is a rectangular region.

The region detecting function of the irradiation region detecting portion 13a and the indication selecting function of the indication region selecting portion 13b are shown conceptually in FIGS. 12A–12C.

As shown in FIG. 12A, when the entire irradiation region is detected by the X-ray flat panel detector, if the all-pixel display mode is selected, that region is displayed as it is as shown on top. If the irradiation region display mode is selected, only the irradiation region plus a margin is displayed in enlargement as shown in the middle. If the patient region display mode is selected, only the patient region plus a margin is displayed in enlargement as shown on bottom.

Further, as shown in FIG. 12B, when only part of the irradiation region is detected by the X-ray flat panel detector, if the all-pixel display mode is selected, that region is displayed as it is as shown on top. If the irradiation region display mode is selected, only a detected irradiation region is displayed in enlargement as shown in the middle. If the patient region display mode is selected, only a detected patient region is displayed in enlargement as shown on bottom.

Further, if no irradiation region is detected by the X-ray flat panel detector as shown in FIG. 12C, for example, "NO IMAGE" is displayed regardless of the all-pixel display mode, irradiation region display mode and patient region display mode.

Figure 10:
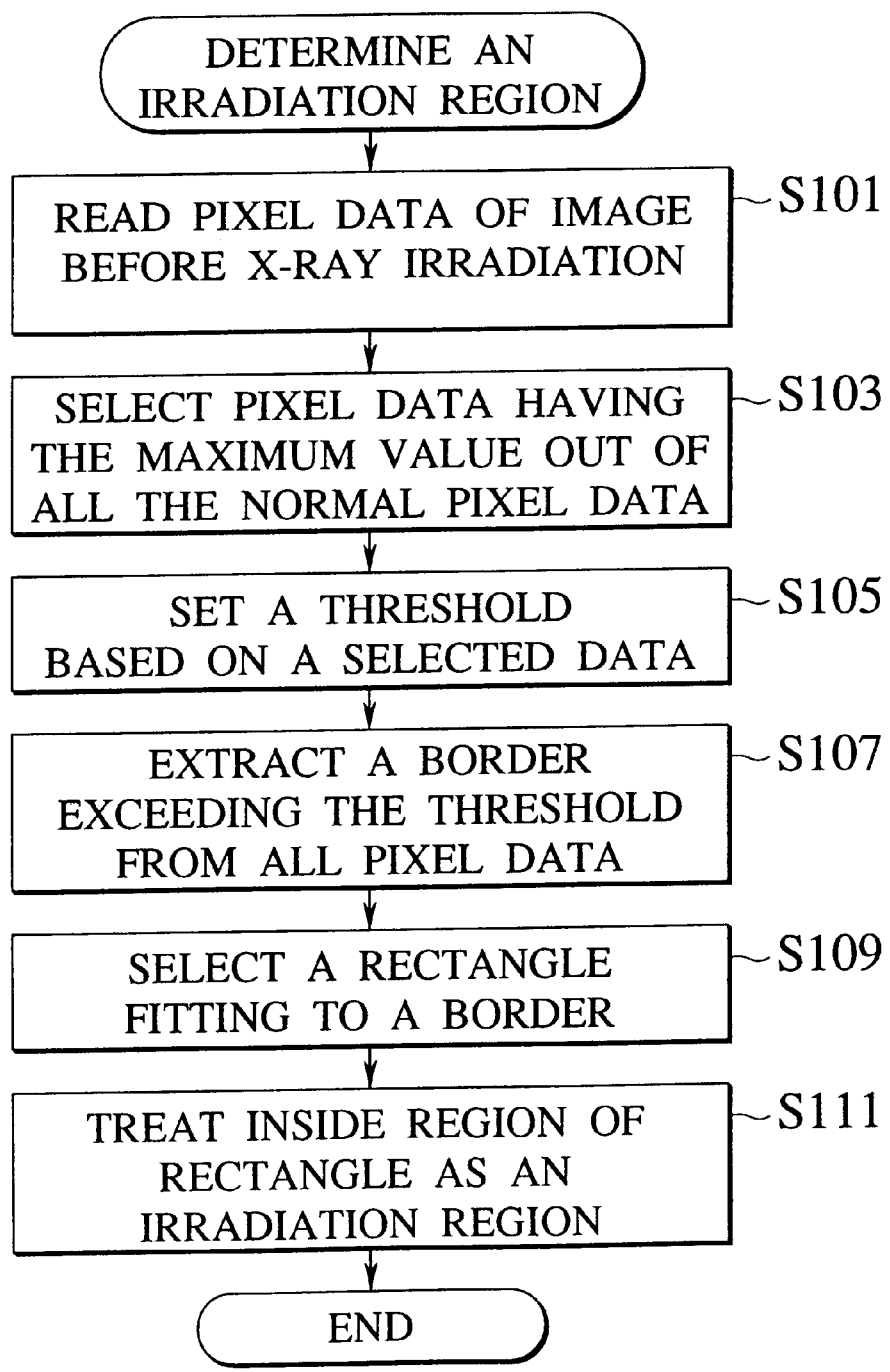
FIG. 10 is a flow chart for explaining a detail of an irradiation region determination.

FIG. 10 provides a flow chart indicating a detailed procedure for determining the irradiation region. First, pixel data of an image in such a state that an X-ray is not irradiated are read out before X-ray irradiation (step S101) and then pixel data having the maximum value out of all the normal pixel data excluding abnormal pixel data is selected (step S103). Then, a value acquired by multiplying the selected pixel value by 1.1, for example, is set as a threshold (step S105).

Then, a border between pixel data having values exceeding that threshold and pixel data having values not exceeding the threshold is extracted (step S107) and a rectangle fitting to this border is selected (step S109). Then, a region within this rectangle is determined as an irradiation region (step S111). If no border exceeding the threshold can be detected at step S107, a flag saying that there is no irradiation region is posted, so that this is used for determining whether or not there is an irradiation region at step S17 of FIG. 9.

Upon detecting the border, it is permissible to differentiate the pixel data and apply a portion in which the result of this differentiation maximizes as the border.

Figure 11:
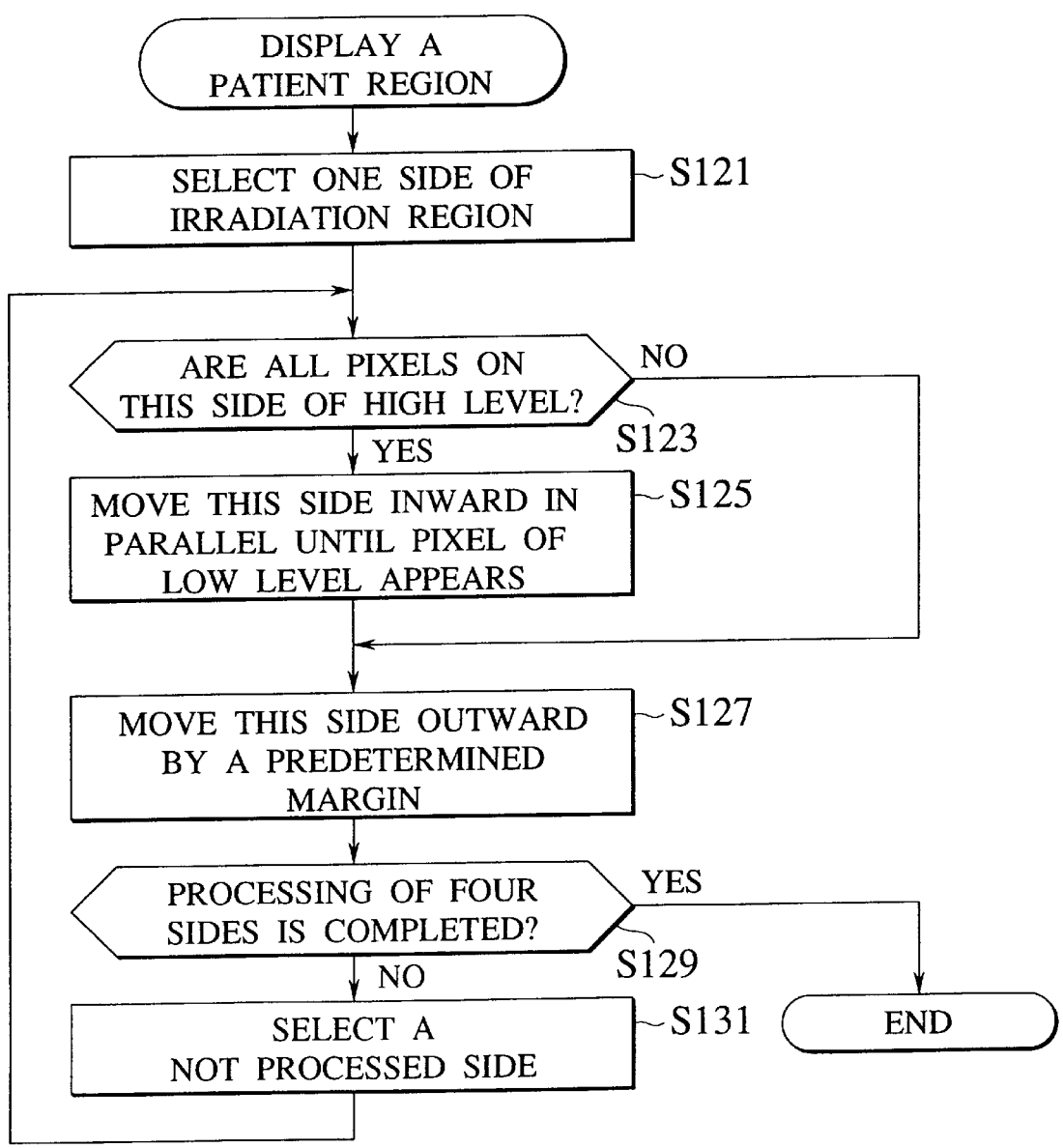
FIG. 11 is a flow chart for explaining a detail of patient region display.

FIG. 11 is a flow chart showing a procedure for determining and displaying the patient region.

If the patient region display mode is selected, a region determined by the irradiation region determination of FIG. 10 is input and one side of this irradiation region is selected and then its pixel data is read (step S121). Then, whether or not all pixel data on this side are of high level is determined (step S123). If all the pixel data are of high level, it comes that this side exists outside the patient region. Thus, the side is moved in parallel inward of an image until a low level pixel appears (step S125). If the low level pixel is found in the determination of step S123, it comes that this side exists inside the patient region, and thus the processing jumps to step S127 immediately.

Then, at step S127, this side is moved in parallel outward by a predetermined margin. The predetermined margin is, for example, 2–3 cm on the X-ray flat panel detector.

Then, whether or not processing about four sides is completed is determined (step S129) and if such a procedure is not completed, a not treated side is selected (step S131) and the processing returns to step S123. If processing on the four sides is completed, a region surrounded by these four sides is picked up as a display region and the processing is terminated.

FIGS. 13A–13D explain operations of the irradiation region detecting portion 13a and indication region selecting portion 13b in a case when the patient region display mode is set based on a concrete X-ray radiography condition.

Figure 13A:
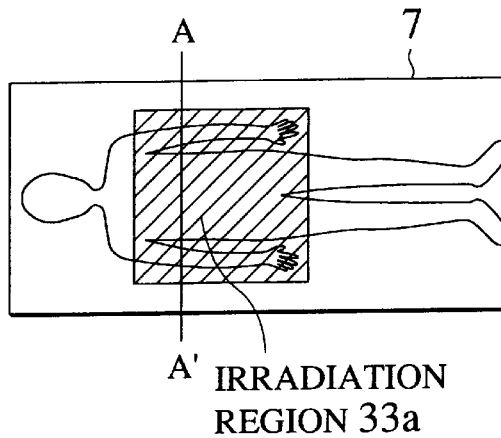
FIGS. 13A–13D are diagrams for explaining the irradiation region and display region.
Figure 13B:
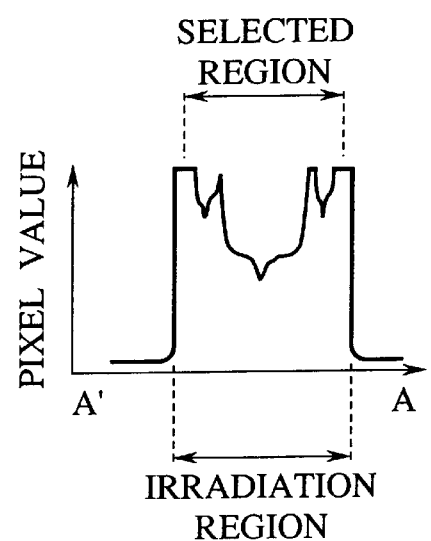

If the patient is placed in the X-ray irradiation region as shown in FIG. 13A, pixel values on the lines A–A' of the same figure detected by the X-ray flat panel detector 7 are output as values indicated in FIG. 13B.

Referring to FIG. 13B, a range in which the pixel value reaches the highest level is an irradiation region including no patient and a valley of the pixel value corresponds to a bone of the hand or spinal portion. Because pixel values outside the irradiation region in the X-ray flat panel detector are pixel values indicating low level because of only scattered beam, a position in which the pixel value rises suddenly from this low level is determined as a border of the irradiation region. In this case, if the display region is determined on the patient region display mode, the patient region plus a predetermined margin from an end thereof, namely, a selected region shown in FIG. 13B is employed.

Figure 13C:
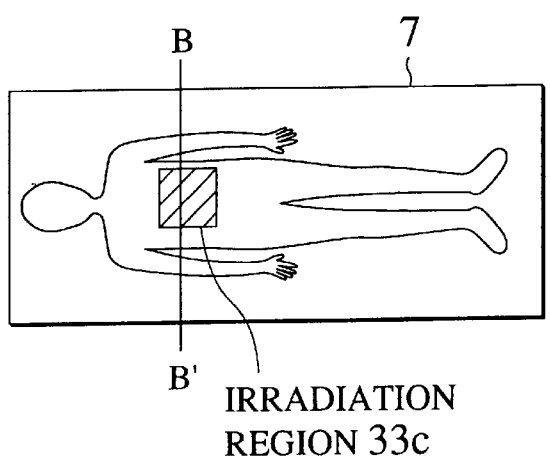
Figure 13D:
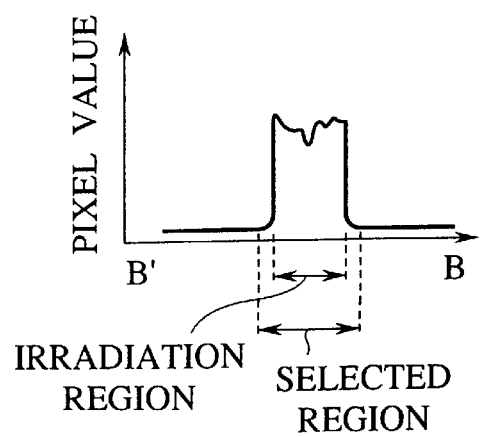

If the patient is placed beyond the X-ray irradiation region as shown in FIG. 13C, the pixel values on the lines B–B' are output as values shown in FIG. 13D.

Referring to FIG. 13D, pixel values corresponding to the patient are obtained within the irradiation region and outside the irradiation region, only pixel values of low level due to scattered beam are obtained. Therefore, a position in which the pixel value rises suddenly from this low level is determined as a border of the irradiation region. In this case, if the display region is determined on the patient region display mode, a patient region, in this case, an irradiation region plus a predetermined margin from an end thereof is employed as a selected region shown in FIG. 13D.

FIGS. 14A–14D explain a procedure for enlarging or reducing a region selected as the display region corresponding to the monitor. Suppose that live data of a region selected as the display region is, for example, that is shown in FIG. 14A. In FIG. 14A, 16 pixel data D1, D2, D3, . . . , D16 are indicated in a cube of 4×4.

As for the display method, the pixels are displayed in the same quantity of the pixels as in the selected region. As shown in FIG. 14C, the quantity of the pixels is enlarged an integer times that of the selected pixels within a range which can be brought into the monitor size. Alternatively, as shown in FIG. 14D, the quantity of the pixels is reduced by an integer time after averaging plural continuous pixels.

Next, a second embodiment of the present invention will be described. FIG. 15 is a flow chart showing an operation of the second embodiment. According to this embodiment, by using an irradiation region determined by a result of pre-irradiation or preceding irradiation, a region for read out in subsequent irradiation is limited so as to enhance reading speed for pixel data from the X-ray flat panel detector.

Although the overall structure of the X-ray diagnostic apparatus of this embodiment is like the first embodiment shown in FIG. 6, operations of the irradiation region detecting portion 13a and indication region selecting portion 13b are different.

Referring to FIG. 15, first, irradiation time (n) is initialized (n=0) (step S41). Next, the X-ray is irradiated (step S43) and then the irradiation time is updated (step S45). Then, whether or not the irradiation time n is larger than 1 is determined (step S47).

Because n=1 at the first irradiation, a determination result is first NO. Next, all pixel data are read out from the X-ray flat panel detector (step S49), an irradiation region is determined (step S51), a display region is selected (step S53) and this display region is stored (step S55).

As for selection of the display region at step S53, the display region is selected based on a mode selected from the all-pixel display mode, irradiation region display mode and patient region display mode as in the first embodiment.

Then, an image in the display region is enlarged or reduced corresponding to the size of the screen like the first embodiment (step S57) and this image is displayed (step S59). In a case when the patient region display mode is selected and the patient region is a part of the irradiation region, a degree of the opening of the X-ray beam limiting device is reduced so as to project the X-ray only within the display region. As a result, irradiation on an unnecessary region with the X-ray beam can be cut off, and thereby exposure on the patient is reduced. Then, whether or not the irradiation with the X-ray beam is terminated is determined (step S61), and if that procedure is not terminated, the processing returns to step S43.

In case of the irradiation with the X-ray at a second or following time, the determination result at step S47 is YES so that the processing goes to step S63. At step S63, when the pixel data is read out from the X-ray flat panel detector, only the pixel data within a display region memorized at step S55 is read out.

In a this case, the processing time can be reduced as shown in FIGS. 16A, 16B and FIGS. 17A, 17B.

Figure 17A:
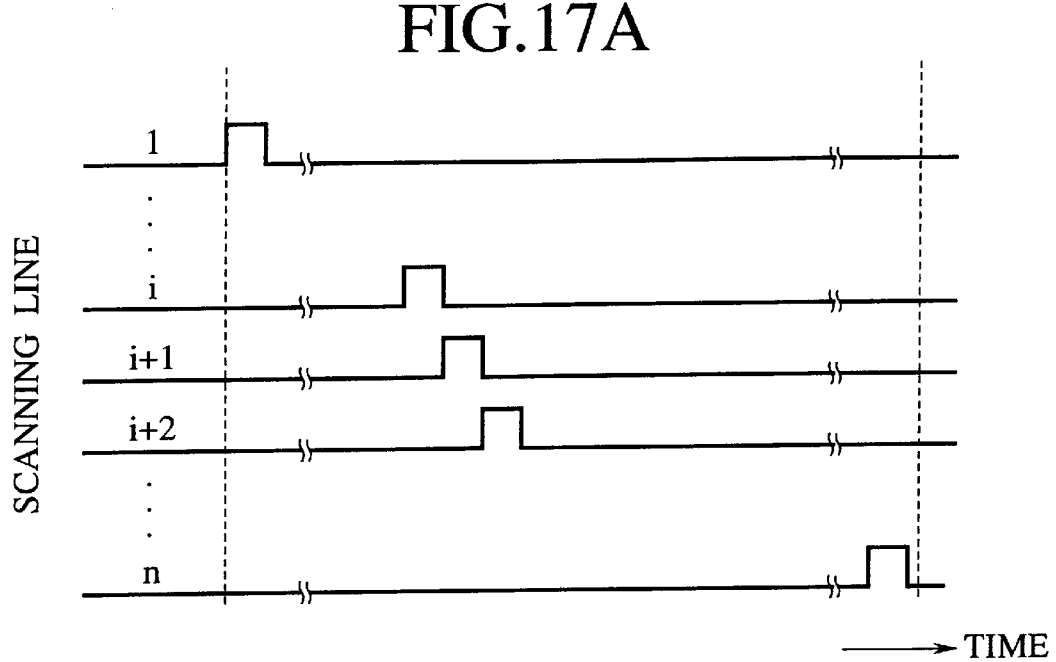
FIGS. 17A, 17B are diagrams for explaining a method for reading only part of data in the irradiation region.

In a case of collecting all pixel data, processing for collection and read-out takes a time corresponding to the quantity of scanning lines as shown in FIG. 17A. Suppose that the width of a pulse for read-out is required to be 30 $\mu$s, if there are 1,000 scanning lines, it comes that 30 $\mu$s×1000= 30 ms is taken to collect all the pixel data.

Figure 16A:
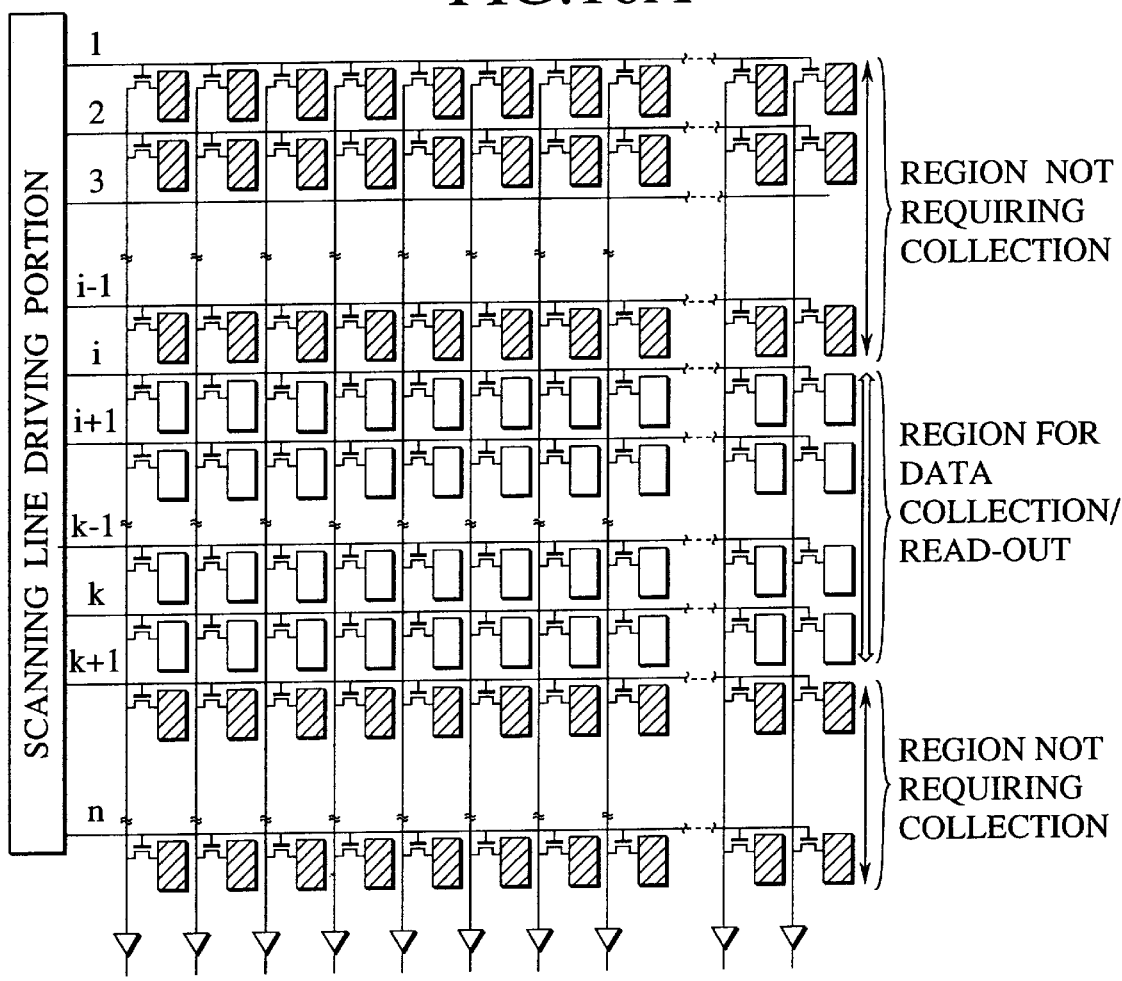
FIGS. 16A, 16B are diagrams for explaining a method for reading only part of data in the irradiation region.
Figure 17B:
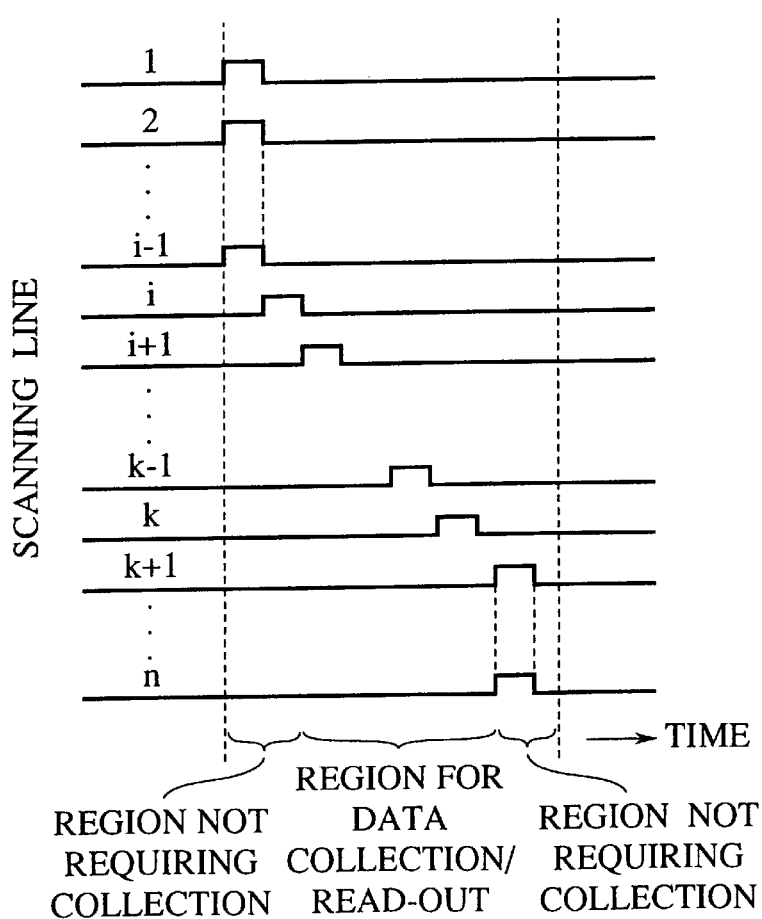

On the other hand, assume that as shown in FIG. 16A, only the pixel data corresponding to scanning lines i, i+1, . . . , k+1, k are data which should be collected. In this case, the region not requiring collection of data has only to be subjected to a processing for sweeping data out in batch. For this purpose, as shown in FIG. 17B, reading control pulses are generated about the scanning lines 1–(i−1) in the same time zone and the reading control pulses about the scanning lines (k+1)–n are generated in the same time zone. As a result, the processing time can be reduced corresponding to an area of a region of pixels from which data is read out.

Figure 16B:
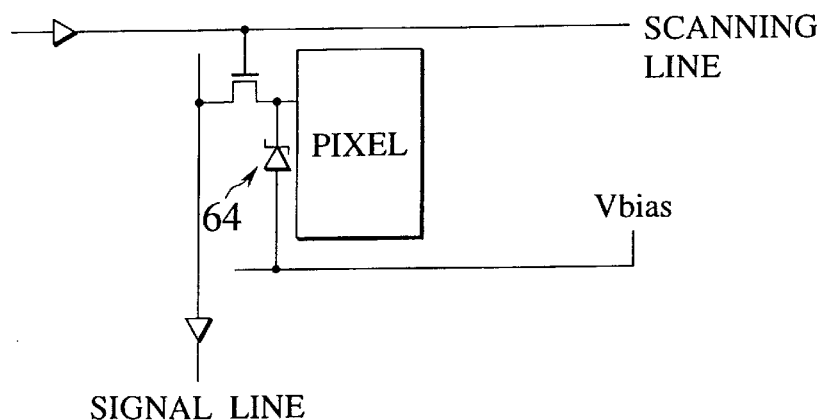

As for an electric charge on a pixel in a region not requiring collection of data, it is effective to discharge it to a power supply line via a zener diode 64 as shown in FIG. 16B. If the bias voltage Vbias supplied to the power supply line is turned to a low level, the zener diode 64 is opened so that the electric charge is discharged. As a result, destruction of insulation can be prevented, and further, a leakage of the electric charge to a signal line via the TFT can be prevented.

Although most preferably data in a region not requiring collection of data should be swept out at the same time, it is also permissible to sweep out such data in succession by comparing with a region requiring collection of data quickly.

Returning to the description of the flow chart of FIG. 15, the margin around an image region whose pixels have been read out is compared with a predetermined margin (step S65). If that margin is larger than the predetermined margin, the processing goes to step S57, in which the image is enlarged or reduced and then displayed.

If the margin is smaller than the predetermined value, the processing proceeds to step S49, in which a processing after reading of all the pixel data from the X-ray flat panel detector is carried out. At step S65, only when the irradiation region display mode is selected, will it be determined whether the subsequent processing should proceed to step S49 or S57. If the all-pixel display mode or patient region display mode is selected, the subsequent processing proceeds to step S57 without any determination.

By the above processing, read-out of the pixel data from the X-ray flat panel detector at a second time and on for collection of the X-ray irradiation data can be conducted by reading only its display data preliminarily stored unless the patient and X-ray source are not moved, so that reduction of the reading time can be achieved. Further if the patient or X-ray source is moved, its display region can be updated following this moving. Thus, the X-ray image collected on the X-ray flat panel detector can be displayed on the monitor. As a result, fluoroscopy can be carried out.

FIGS. 18A–18C show an example for determining whether or not the pixel data reading region for subsequent irradiation with an X-ray beam exists within a margin region. In a case the pixel data is read out from the X-ray flat panel detector with respect to a display region memorized preliminarily, in case shown in FIG. 18B, the irradiation region is within the display region but in case of FIG. 18C, the irradiation region is outside the display region.

Figure 19A:
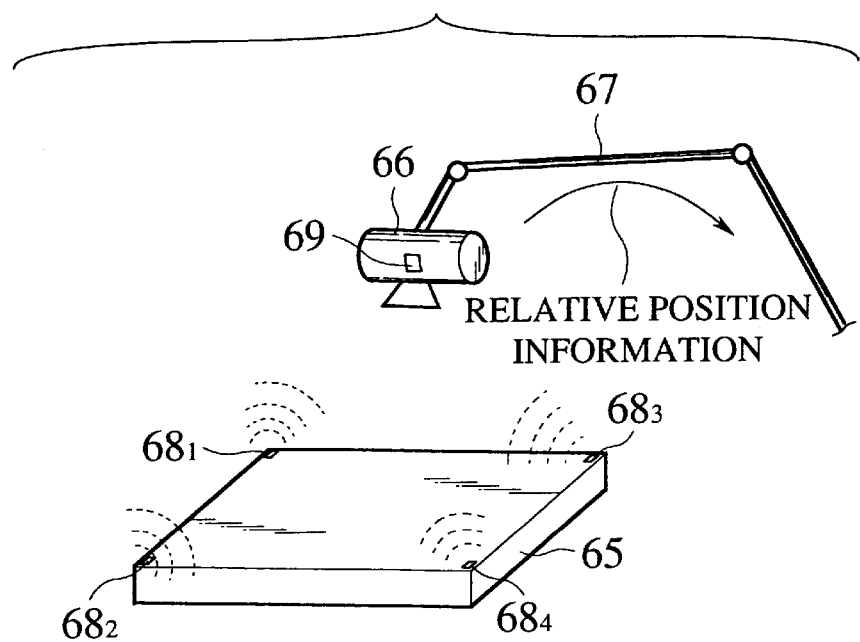
FIGS. 19A, 19B are configurational diagrams showing major parts of a third embodiment.
Figure 19B:
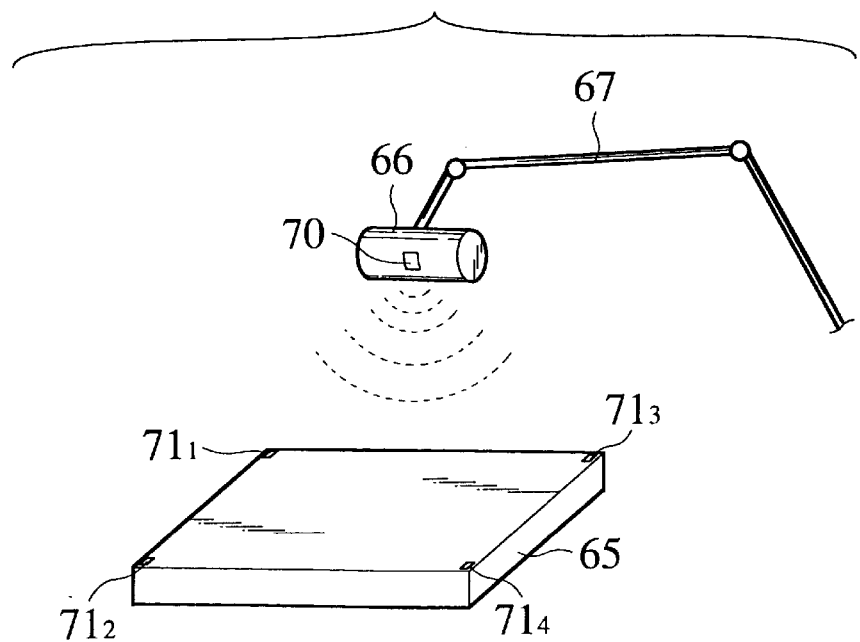

FIG. 19 is a diagram for explaining a structure of major components of a third embodiment of the X-ray diagnostic apparatus according to the present invention. According to this embodiment, the irradiation region is estimated based on a distance between an X-ray focal point and an X-ray flat panel detector and a degree of opening of the beam limiting device and data collection region is selected according to this estimation result.

In FIG. 19A, ultrasonic wave generators $68_1$–$68_4$ are placed on four corners of the X-ray flat panel detector 65. An X-ray head 66 containing an X-ray tube and X-ray beam limiting device (both not shown) is provided on an end portion of an adjustable arm 67 having plural rotatable articulates. An ultrasonic wave receiver 69 having a directivity downward in a wide range is provided on a side of the X-ray head 66.

The ultrasonic wave receiver 69 receives ultrasonic wave pulses dispatched from the ultrasonic wave generators 681-684 to measure a transmission delay time of each pulse and then calculates a distance between the X-ray head 66 and X-ray flat panel detector 65 based on this measured time and sound velocity. If a room temperature is measured to correct the sound velocity at this time, a more accurate distance can be obtained.

Next, the degree of opening of the X-ray beam limiting device provided in the X-ray head 66 is read out and an irradiation region on the X-ray flat panel detector is calculated according to the degree of opening of the beam limiting device and the distance between the X-ray head and X-ray flat panel detector.

Then, X-ray beam is irradiated from the X-ray tube in the X-ray head. If the X-ray flat panel detector is not located at a position irradiated with the X-ray beam, it is permissible to suppress the irradiation with the X-ray beam and dispatch an alarm to an operator. Further, it is permissible to provide a mechanism for indicating which part of the patient can be taken by projecting visible laser beam or the like to a region which can be irradiated with the X-ray beam.

Although FIG. 19A has explained a case in which the ultrasonic wave generators are provided on the X-ray flat panel detector and the ultrasonic wave receiver is provided on the X-ray head, on the contrary, it is needless to say that the distance can be measured even if the ultrasonic wave generator 70 is provided on the X-ray head 66 and the ultrasonic wave receivers $71_1$–$71_4$ are provided on four corners of the X-ray flat panel detector 65.

Figure 20:
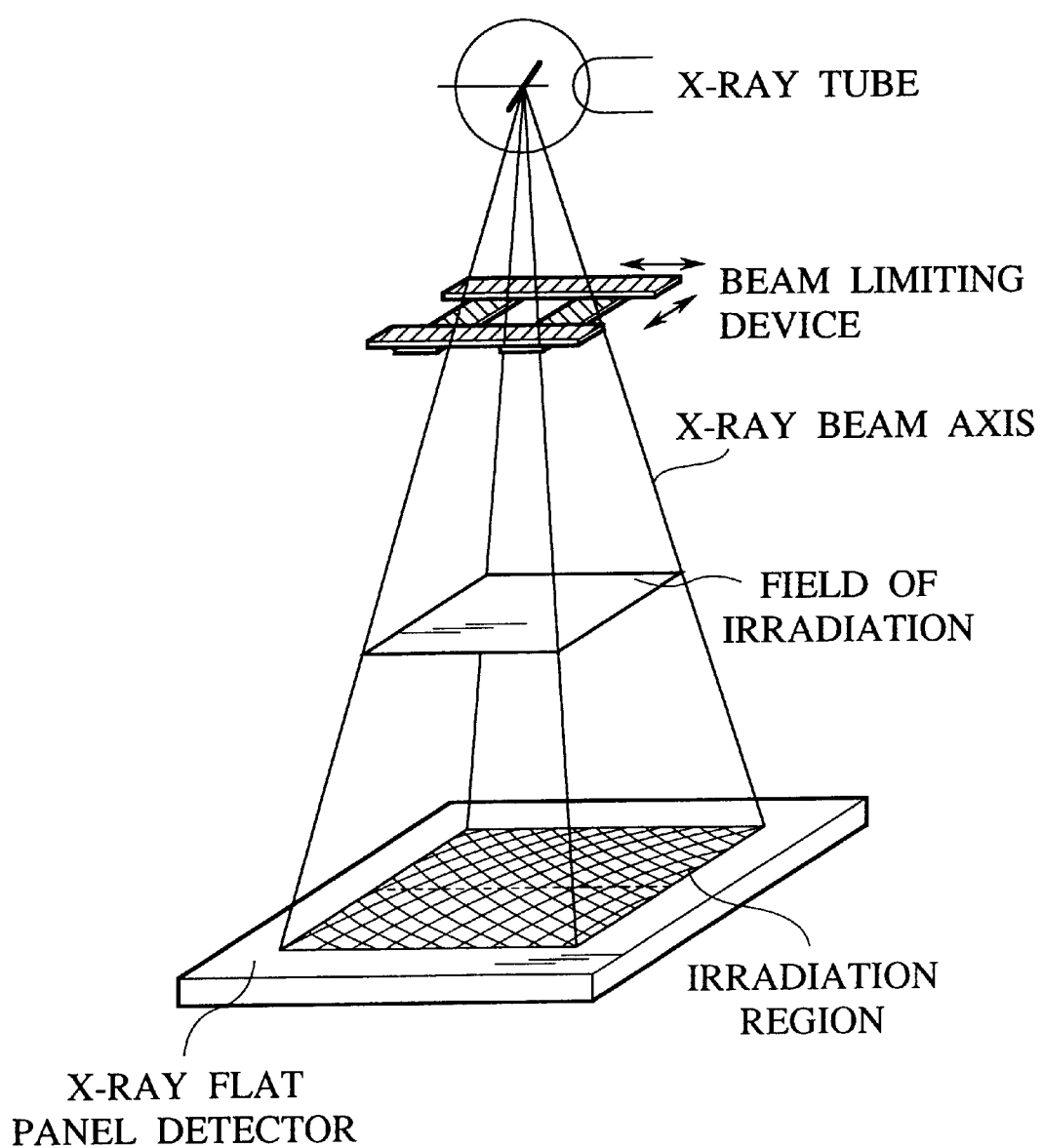
FIG. 20 is a diagram for explaining X-ray focal point, beam limiting device, and geometry of the irradiation region in the X-ray flat panel detector.

FIG. 20 is a diagram showing a geometry between the X-ray tube and X-ray beam limiting device in the X-ray head and the irradiation region of the X-ray flat panel detector. As shown in the same figure, the irradiation region is automatically determined by a relation between the X-ray focal point and X-ray flat panel detector and the degree of opening of the beam limiting device.

Figure 21:
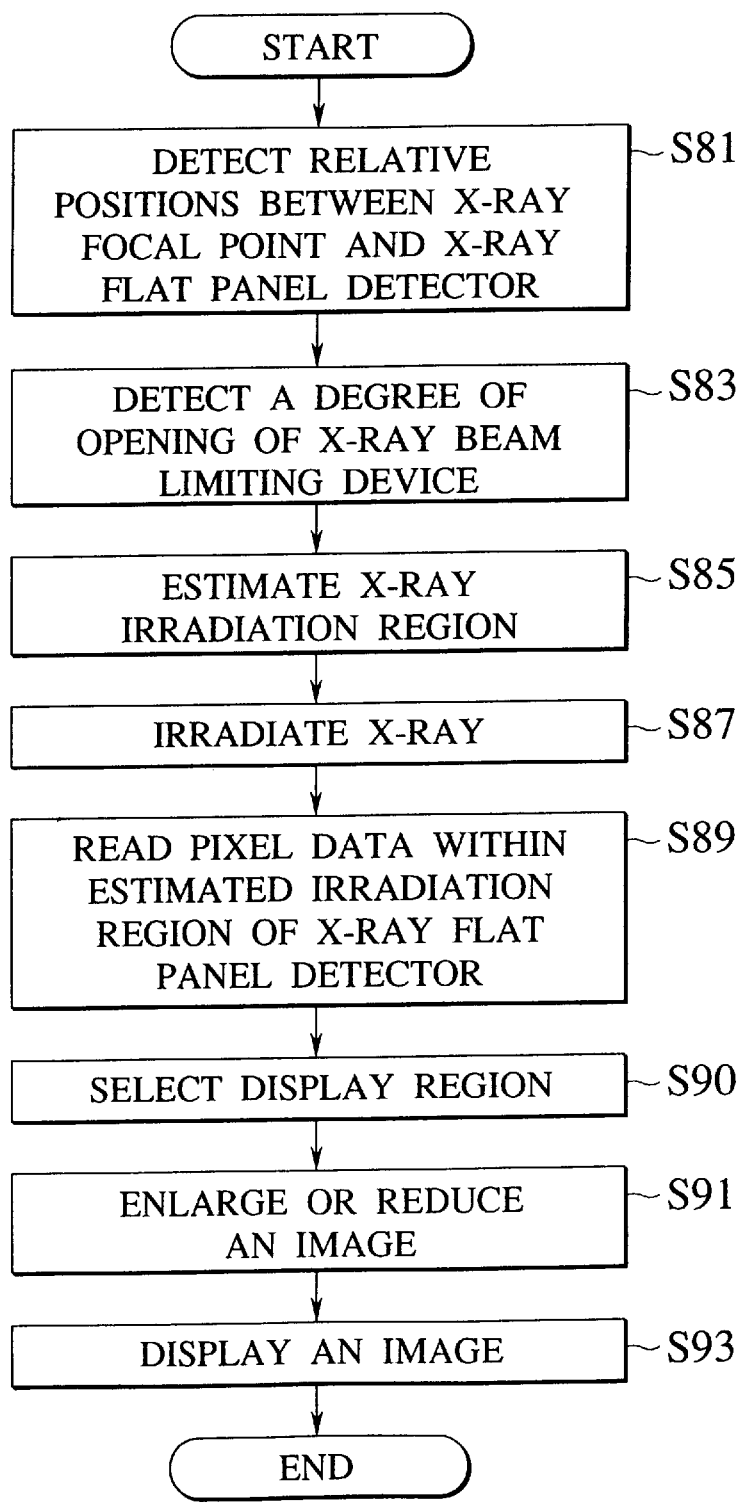
FIG. 21 is a flow chart for explaining an operation of the third embodiment.

FIG. 21 is a flow chart for explaining an operation of the third embodiment.

First, a relative position between the X-ray focal point and X-ray flat panel detector is detected (step S81) and then the degree of opening of the X-ray beam limiting device is detected (step S83). An order for detecting the relative position and degree of opening of the beam limiting device may be exchanged.

Then, an expected irradiation region on the X-ray flat panel detector is calculated according to the relative position between the X-ray focal point and X-ray flat panel detector and the degree of opening of the beam limiting device (step S85). In this case, it is permissible to dispatch an alarm so as to urge the operator to correct the position of the X-ray flat panel detector if the X-ray flat panel detector is not located within a region which can be irradiated with X-ray beam. Further, it is also permissible to provide a function enabling to recognize which part of the patient can be taken by projecting visible light to a region which can be irradiated.

Next, the X-ray is irradiated from the X-ray head (step S87), only the pixel data of the X-ray flat panel detector included by this calculated expected irradiation region is read out (a method shown in FIGS. 16A and 17B can be employed) and that pixel data is stored in the image memory (step S89). Then, a display region is selected as in the first embodiment (step S90). This display region selection is carried out based on a mode selected from the irradiation region display mode and patient display mode. Then, the image is enlarged or reduced (step S91), displayed on the monitor (step S93) and the processing is terminated.

In a case of fluoroscopy, consecutive images are taken by repeating steps S81–S91. If the patient region display mode is selected, the degree of opening of the X-ray beam limiting device is reduced so that the X-ray beam can be irradiated only within the display region, and thereby the exposure on the patient is reduced.

Then, a fourth embodiment of the present invention will be described.

According to this embodiment, a thin type X-ray flat panel detector is provided on an entire range of a patient bed fixedly or removably and this X-ray flat panel detector is combined with a movable diagnostic X-ray apparatus for round of visit for medical check. The X-ray apparatus for round of visit comprises an X-ray tube as an X-ray source for generating the X-ray beam, a power source for supplying a required power to this X-ray tube and a control unit for processing and memorizing image data obtained from the X-ray flat panel detector and displaying on the display unit.

Because a bed provided with such an X-ray flat panel detector allows radiography on the patient without a necessity of taking him to an X-ray radiography room, it enables to easily radiograph a patient with a serious disease or a patient having difficulty with walking or moving.

A single X-ray apparatus for round of visit for medical check can correspond to a plurality of the X-ray flat panel detectors, thereby making it possible to take a number of radiographs.

According to the respective embodiments described above, setting of relative positions of the X-ray source and X-ray detector and setting of the position of the patient are not required, so that the X-ray image can be obtained without any trouble and labor.

Particularly, in a case of emergency diagnosis, there is such an effect that the labor necessary for the radiography is reduced so that the X-ray image can be obtained quickly.

Further, the respective embodiments described above can be applied to both radiography and fluoroscopy.

Next, a fifth embodiment of the present invention will be described.

Figure 22:
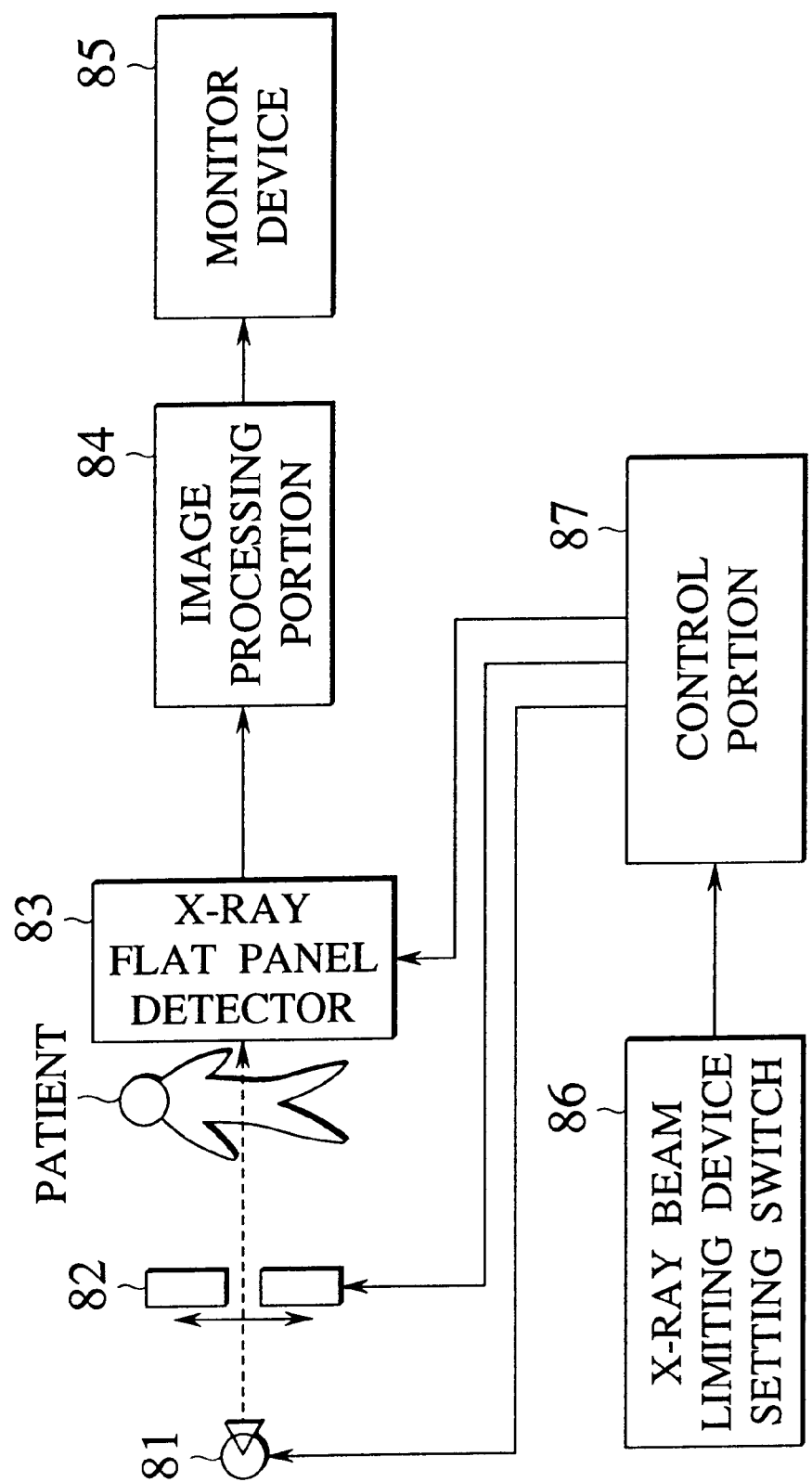
FIG. 22 is a block diagram of an X-ray diagnostic apparatus according to a fifth embodiment of the present invention.

As shown in FIG. 22, the X-ray diagnostic apparatus according to the fifth embodiment of the present invention comprises an X-ray tube 81 controlled so as to generate X-ray having a large dose at the time of radiography and X-ray having a small dose at the time of fluoroscopy, an X-ray beam limiting device 82 for narrowing the X-ray irradiation region so that the X-ray is irradiated to only an interest region, an X-ray flat panel detector 83 for receiving an X-ray image which passes through the patient and converting this X-ray image to image signal as an electric signal, and an image processing portion 84 for subjecting an image signal sent from the X-ray flat panel detector 83 to a predetermined signal processing and supplying that signal to a monitor device 85.

This X-ray diagnostic apparatus comprises an X-ray beam limiting device setting switch 86 which is operated by an operator to specify an X-ray irradiation region and a control portion 87 for controlling the X-ray tube 81 so as to change the X-ray dose corresponding to an object of irradiation, control the width of opening of the X-ray beam limiting device 82 so as to obtain an X-ray irradiation region specified by the X-ray beam limiting device setting switch 86 and controlling a reading region of the X-ray flat panel detector by the first-third mode described later corresponding to this X-ray irradiation region.

Next, an operation of the X-ray diagnostic apparatus according to the fifth embodiment having such a structure will be described.

The X-ray flat panel detector 83 has the same structure as the X-ray flat panel detector 7 as shown in FIG. 7A.

In a following description, it is assumed that the numbers of pixels in the longitudinal and lateral directions of the X-ray flat panel detector 83 are 4000 pixels×4000 pixels and the processing capacity of the image processing portion 84 on a following step is 1000 pixels×1000 pixels.

In a case of obtaining an X-ray image, generally an object portion is found by fluoroscopy or timing is measured, and then the X-ray image is taken by radiography. If the description is proceeded following this general procedure for the X-ray image, in FIG. 22, the operator specifies fluoroscopy and then specifies an object area for observation by fluoroscopy with the X-ray beam limiting device setting switch 86 (specifying an X-ray irradiation region).

If the object area for observation by fluoroscopy is specified by the X-ray beam limiting device setting switch 86, the control portion 87 controls the X-ray tube 81 so as to continuously irradiate X-ray of a smaller dose than that for radiography, control the width of the opening of the X-ray beam limiting device 82 so that the X-ray is irradiated only within that specified region and control the reading of the X-ray flat panel detector 83 so as to read out the X-ray image corresponding to that specified X-ray irradiation region.

A concrete operation will be described below.

The control portion 87 changes the size of the X-ray irradiation region by moving the X-ray beam limiting device 82 based on an input into the X-ray beam limiting device setting switch 6. At this time, the control portion 87 regards the X-ray irradiation region set by the X-ray beam limiting device setting switch 86 as an object area for observation and decides an operation mode based on the size of this observation region.

(First Mode)

Figure 23:
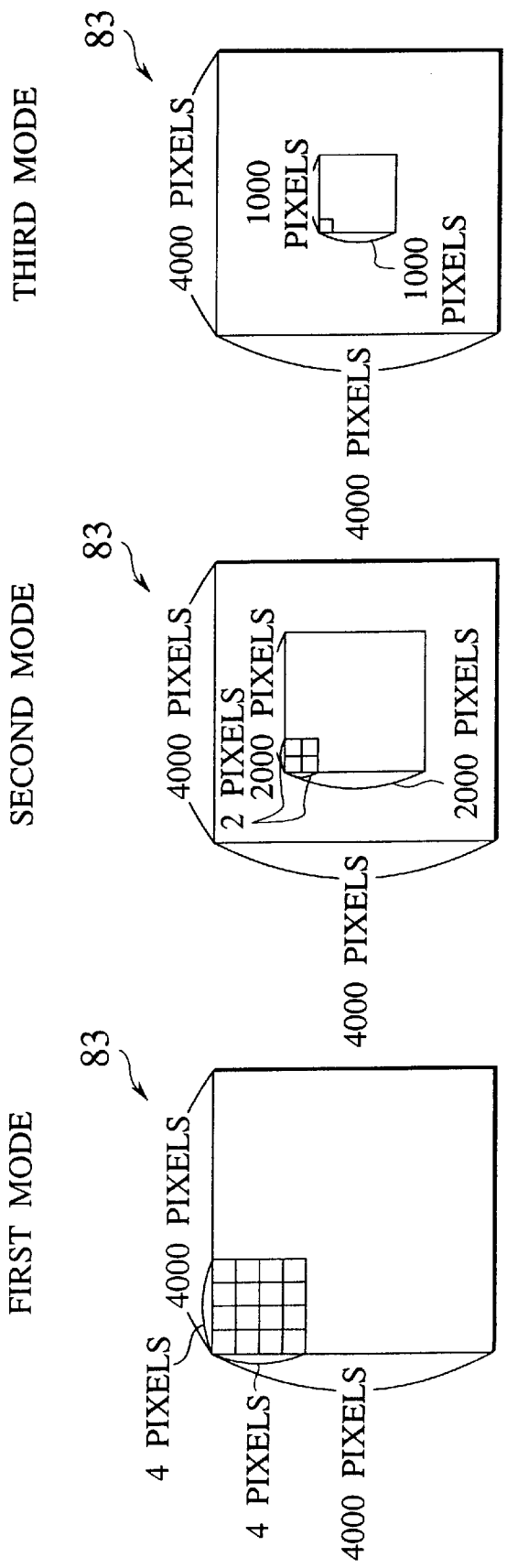
FIGS. 23A–23C are diagrams showing a reading region of the X-ray flat panel detector in case where the X-ray diagnostic apparatus of the fifth embodiment controls reading at first-third mode.

In a case when length in the longitudinal direction of the X-ray flat panel detector 83 divided by 2 is smaller than the length in the longitudinal direction of the observation region and the length in the lateral direction of the X-ray flat panel detector divided by 2 is smaller than the length in the lateral direction of the observation region (or in a case when an area of the observation area is ¼–¹⁄₁ the radiography surface of the X-ray flat panel detector 83), the first mode is set. In this first mode, as shown in FIG. 23A, the reading of the X-ray flat panel detector is controlled so as to read an entire image of 4000 pixels×4000 pixels in such a condition that 16 pixels of 4 pixels×4 pixels is regarded as a single pixel.

In a case when the X-ray flat panel detector 83 reads out totally 16 pixels of 4 pixels×4 pixels as a single pixel, the control portion 87 turns ON the TFTs 32 provided on each pixel 31 of every four lines (row) at the same time via the scanning line driving portion 34 shown in FIG. 7A. As a result, electric charges of the four lines in which each TFT 32 is turned ON are read out to the signal line 36 at the same time and summed up, and then supplied to the multiplexer 38 via the readout amplifier 37.

Next, the control portion 83 turns ON every four switch 38-1–38-4, 38-5–38-8, . . . adjacent in the direction of column in the multiplexer 38 at the same time. Consequently, the image signals of four signal lines are summed up, so that the image signals of totally 16 pixels of 4 pixels×4 pixels are read out as an image signal of a single pixel.

Further concretely speaking, the control portion 37 turns ON each TFT 32 connected to each of totally four lines of the scanning lines 33-1, 33-2, 33-3, 33-4. Consequently, electric charge is read out to the signal line 36 through each TFT 32 of the aforementioned four lines and supplied to the multiplexer 38. Next, the control portion 37 turns ON the four switches 38-1–38-4 adjacent in the direction of the column in the multiplexer 38. As a result, the image signals of the four signal lines are summed up, so that an image signal of totally 16 pixels of 4 pixels×4 pixels is read out as a single image signal.

Therefore, in the first mode, total pixels of 4000 pixels× 4000 pixels in the X-ray flat panel detector 3 can be output in the form of an image signal of 1000 pixels×1000 pixels. Because the processing capacity of the image processing portion 84 at the following step in the X-ray flat panel detector 83 is 1000 pixels×1000 pixels, by controlling this readout, the pixels in the X-ray flat panel detector 83 can be handled as a signal rate within a range of processing capacity of the image processing portion 84.

Next, the image signal read out from the X-ray flat panel detector 83 is supplied to the image processing portion 84 via the output terminal 39. The image processing portion 84 carries out a predetermined image processing (video processing or the like) on this image signal and supplies this signal to the monitor device 85. Consequently, an X-ray image (fluoroscopy image) obtained from an entire region of the X-ray flat panel detector 83 can be displayed on the display screen of the monitor device 85.

(Second Mode)

In a case when length in the longitudinal direction of the X-ray flat panel detector 83 divided by 2>length in the longitudinal direction of the object area for observation>length in the longitudinal direction of the X-ray flat panel detector 83 divided by 4, and further length in the lateral direction of the X-ray flat panel detector 83 divided by 2>length in the lateral direction of the object area for observation>length in the lateral direction of the X-ray flat panel detector 83 divided by 4 (or in case when an area of the object area for observation is ¹⁄₁₆–¼ the radiography surface of the X-ray flat panel detector 83), the second mode is set. In this second mode, as shown in FIG. 23B, an area which is ¼ the entire region is an area in which the numbers of pixels in the longitudinal and lateral directions are 2000 pixels×2000 pixels. The control portion 87 controls reading of the X-ray flat panel detector 83 so as to read totally four pixels of 2 pixels×2 pixels as a single pixel in 2000 pixels× 2000 pixels.

In a case of reading totally four pixels of 2 pixels×2 pixels as a single pixel in the X-ray flat panel detector 83, the control portion 87 turns ON every two line in the scanning lines 33 corresponding to an image constituted of 2000 pixels×2000 pixels and turns ON every two switches adjacent in the direction of the column in the multiplexer 38 corresponding to the image of 2000 pixels×2000 pixels.

Consequently, totally two pixels×two pixels can be read out as a single pixel like in the aforementioned control for reading of four pixels×four pixels. Therefore, in this second mode, an X-ray image of 2000 pixels×2000 pixels on the X-ray flat panel detector 83 can be read out as an image signal of 1000 pixels×1000 pixels, so that those signals can be handled as a signal rate within the processing capacity of the image processing portion 84 on the following step. Because totally four pixels of 2 pixels×2 pixels are read out as a single pixel, as compared to the first mode, four times higher resolution fluoroscopy image can be obtained so that an image of an interest area can be observed in detail.

Next, if there is an area which the operator wants to observe further in detail in the displayed entire fluoroscopy image or an interest area, the operator specifies an X-ray irradiation region so that that interest area is irradiated with the X-ray, with the X-ray beam limiting device setting switch 86.

(Third Mode)

In a case when the length in the longitudinal direction of the X-ray flat panel detector 83 divided by 4 is larger than or equal to the length in the longitudinal direction of the object area for observation and the length in the lateral direction of the X-ray flat panel detector 83 divided by four is larger than or equal to the length in the lateral direction of the object area for observation (or in a case when an area of the object area for observation is 1/16–1/4 the radiography surface of the X-ray flat panel detector 83), the third mode is set. In this third mode, as shown in FIG. 23C, an area which is 1/16 the entire region is an area in which the numbers of pixels in the longitudinal and lateral directions are 1000 pixels×1000 pixels. The control portion 87 controls the reading of the X-ray flat panel detector 83 so as to read out total pixels of 1000 pixels×1000 pixels one by one.

As described, the X-ray flat panel detector 83 is constituted of such multiple pixels as 4000 pixels×4000 pixels. Thus, by reading the X-ray image in a region of 1000 pixels×1000 pixels as it is, they can be handled at a signal rate within a processing capacity of the image processing portion 84 at the following step, and further a high resolution fluoroscopy image can be taken. Concretely speaking, in this third mode, a high resolution fluoroscopy which is 16 times higher than the first mode and four times higher than the second mode can be obtained, so that an image of an interest area can be observed further in detail.

Summarizing the reading control on the first mode third mode by the control portion 87, the control portion 87 controls so as to read total pixels of 4000 pixels×4000 pixels on the X-ray flat panel detector in such a condition that totally 16 pixels of 4 pixels×4 pixels are handled as a single pixel. In the second mode, as shown in FIG. 24, the control portion 87 controls so as to read out 2000 pixels×2000 pixels in an area located in the center of the X-ray flat panel detector as indicated by leftward descending oblique lines of FIG. 24 in a condition that totally four pixels of 2 pixels×2 pixels are handled as a single pixel.

In the third mode, 1000 pixels×1000 pixels in an area located in the center of the X-ray flat panel detector 83 as indicated by rightward descending oblique lines of FIG. 24 are read out one by one as it is.

As a result, a resolution can be selected depending on a degree of accuracy for observation and thereby convenience of the X-ray diagnostic apparatus is improved. Because plural pixels are taken together as a single pixel for read-out, although the X-ray flat panel detector 83 is constituted of multiple pixels so as to raise a spatial sampling frequency, the image processing portion 84 at the following step is never burdened with a high load due to read out image signal, and therefore an existing system can be applied just as it is.

Then, if fluoroscopy at each mode is terminated, the operator instructs radiography on that portion at an arbitrary timing. If this radiography is instructed, the control portion 87 drives the X-ray tube 81 so as to irradiate a great deal of X-ray to the patient and simultaneously controls to fully open the opening of the X-ray beam limiting device 82. As a result, it is possible to obtain an X-ray image including the interest area subjected to fluoroscopy from the entire region of the X-ray flat panel detector 83.

The control portion 87 controls the reading from the X-ray flat panel detector 83 so as to read totally 16 pixels of 4 pixels×4 pixels as a single pixel as in the first mode for fluoroscopy. Consequently, an image of 1000 pixels×1000 pixels can be supplied to the image processing portion 84, so that a burden on the image processing portion 84 can be reduced at the time of radiography. The radiography image via the image processing portion 84 is supplied to the monitor device 85 and displayed thereon.

Because in the description of the fifth embodiment, it is assumed that the image processing portion on the next step of the X-ray flat panel detector 83 has a processing capacity for an image signal of 1000 pixels×1000 pixels, the numbers of the pixels of the image signal to be read out from the X-ray flat panel detector 83 are unified to be 1000 pixels× 1000 pixels at each mode. However, it is permissible to unify 500 pixels×500 pixels, for example, alternatively or set like 1000 pixels×1000 pixels in the first mode, 800 pixels×800 pixels in the second mode, and 400 pixels×400 pixels in the third mode within a range not exceeding the processing capacity of the image processing portion 84.

Although it is assumed that totally three modes, the first mode—third mode are set, it is permissible to set further plural modes depending on resolution, such as first mode—fourth mode or first mode—fifth mode.

Because generally the operator makes fluoroscopy so that a portion which he wants to observe is located in the center of the screen, 2000 pixels×2000 pixels or 1000 pixels×1000 pixels located in the center of the X-ray flat panel detector 83 is controlled so as to be read out at the second or third mode. Alternatively, it is permissible to fix a region located out of the center of the X-ray flat panel detector 83 and read out (an embodiment for reading out an arbitrary region will be described in a seventh embodiment described later). Although reading control on the X-ray flat panel detector 83 at each mode is carried out only for fluoroscopy, this procedure may be carried out at the time of radiography.

Although totally 16 pixels of 4 pixels×4 pixels are read out as a single pixel at the time of radiography, it is permissible to read out the pixels one by one and instead retard frame rate so as to treat within a processing capacity of the image processing portion on the next step.

Next, an X-ray diagnostic apparatus according to a sixth embodiment of the present invention will be described.

Although in the X-ray diagnostic apparatus according to the fifth embodiment, the reading region on the X-ray flat panel detector 83 is automatically set corresponding to an X-ray irradiation region set by the X-ray beam limiting device setting switch 86, in the X-ray diagnostic apparatus of the sixth embodiment, it is possible to set an X-ray irradiation region by an operation of the X-ray beam limiting device setting switch 86 and a reading region on the X-ray flat panel detector 83 separately.

In a description on the X-ray diagnostic apparatus according to the sixth embodiment, the same reference numerals are attached to positions indicating the same operations as the X-ray diagnostic apparatus according to the fifth embodiment and a detailed description thereof is omitted.

Figure 25:
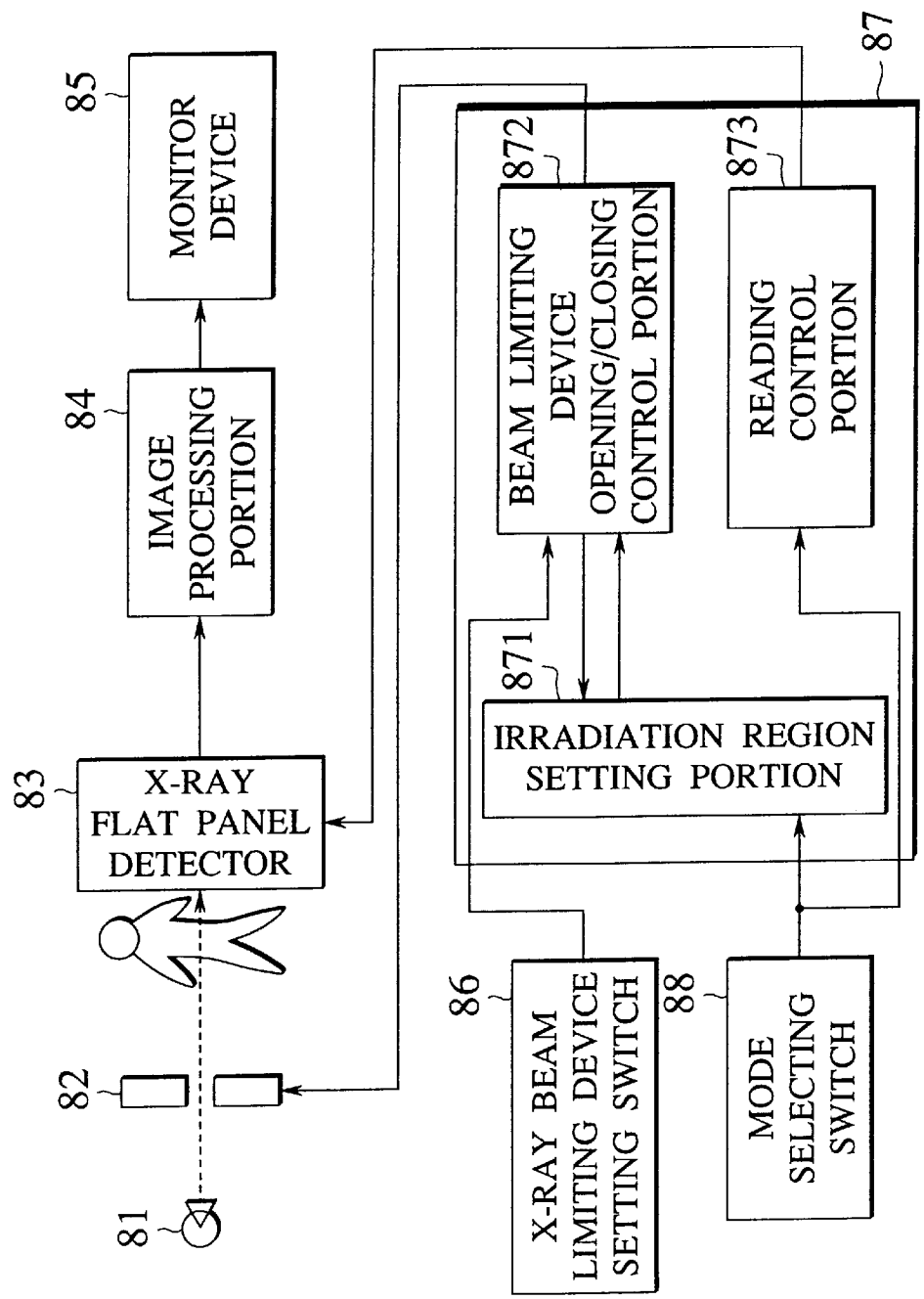
FIG. 25 is a block diagram of the X-ray diagnostic apparatus according to a sixth embodiment of the present invention.

The X-ray diagnostic apparatus according to the sixth embodiment comprises an X-ray beam limiting device setting switch 86 for moving the X-ray beam limiting device 82 and a mode selecting switch 88 for setting an operation mode as shown in FIG. 25. The control portion 87 includes a beam limiting device opening/closing control portion 872 for moving the X-ray beam limiting device 82 and obtaining a position of the X-ray beam limiting device 82, an irradiation region setting portion 871 for obtaining an X-ray irradiation region according to a position of the X-ray beam limiting device 82 and operation mode, a reading control portion 873 for controlling the scanning line driving portion 34 and multiplexer 38 of the X-ray flat panel detector 83 according to mode information from the mode selecting switch 88.

The reading control portion 873 stores size information on the reading region at each mode and a method for summing up pixels. Based on this stored information, a reading region corresponding to mode information from the mode selecting switch 88 and the method for summing up the pixels are obtained.

According to this method for summing up the pixels, the line driving portion 34 and multiplexer 38 are controlled so as to read out pixel information within a reading region. An operation of the X-ray diagnostic apparatus according to the sixth embodiment will be described.

When the operator operates the X-ray beam limiting device setting switch 86, the beam limiting device opening/closing control portion 872 moves the X-ray beam limiting device based on a signal from the setting switch 86.

If setting of the X-ray beam limiting device by the operator is finished, the beam limiting device opening/closing control portion 872 obtains an X-ray irradiation region from the X-ray beam limiting device 82 and sends it to an irradiation region setting portion 871.

If the operator selects one of the first—third modes by operating the mode selecting switch 88, the selected mode information is transmitted to the irradiation region setting portion 871 and reading control portion 873.

If the operator selects one of the first—third modes by operating the mode selecting switch 88, the selected mode information is transmitted to the irradiation region setting portion 871 and reading control portion 873. When the first mode is selected, in the irradiation region setting portion 871 and reading control portion 873, the reading region is set to an entire radiography surface (4000 pixels×4000 pixels) on the X-ray flat panel detector 83 and the method for summing up the pixels is set to every area of 4×4. When the second mode is selected, the irradiation region setting portion 871 and reading control portion 873 sets the reading region to ¼ the radiography surface (2000 pixels×2000 pixels) of the X-ray flat panel detector and the method for summing up the pixels to every area of 2×2. When the third mode is selected, the irradiation region setting portion 871 and reading control portion 873 set the reading region to ¹⁄₁₆ the radiography surface (1000 pixels×1000 pixels) of the X-ray flat panel detector 83 and the method for summing up the pixels to every area of 1×1 (the summing of the pixels is not conducted).

If X-ray irradiation region information and mode information are input, the irradiation region setting portion 871 obtains an optimum X-ray irradiation region based on these information and sends to the beam limiting device opening/closing control portion 872. That is, the irradiation region setting portion 871 outputs an overlapping area between an X-ray irradiation region specified by the operator and a reading region based on a set mode as an optimum X-ray irradiation region. The beam limiting device opening/closing control portion 872 moves the X-ray beam limiting device 82 so that the optimum X-ray irradiation region sent from the irradiation region setting portion 871 is irradiated with the X-ray beam.

Although ½ the entire region of the X-ray flat panel detector 83 is specified as an irradiation region by the operation of the X-ray beam limiting device setting switch 86, if the second mode for handling ¼ the entire region of the X-ray flat panel detector 83 is specified by an operation of the mode selecting switch 88, the opening/closing control portion 872 controls the aperture width of the X-ray beam limiting device 82 so as to project the X-ray beam to only ¼ the region of the X-ray flat panel detector 83 corresponding to the second mode.

On the contrary, if, as a result of comparing the irradiation region with the reading region in the irradiation region setting portion 871, the reading region is wider than the irradiation region (in a case when the X-ray is projected in a narrower region than the reading range), the opening/closing control portion 54 maintains an irradiation region controlled based on the setting on the X-ray beam limiting device setting switch 86.

As a result, such an inconvenience that an excessive X-ray is irradiated out of the reading region of the X-ray flat panel detector 83 is prevented thereby making it possible to reduce an exposure on the patient and further, the same effect as the above described fifth embodiment can be obtained.

Figure 26:
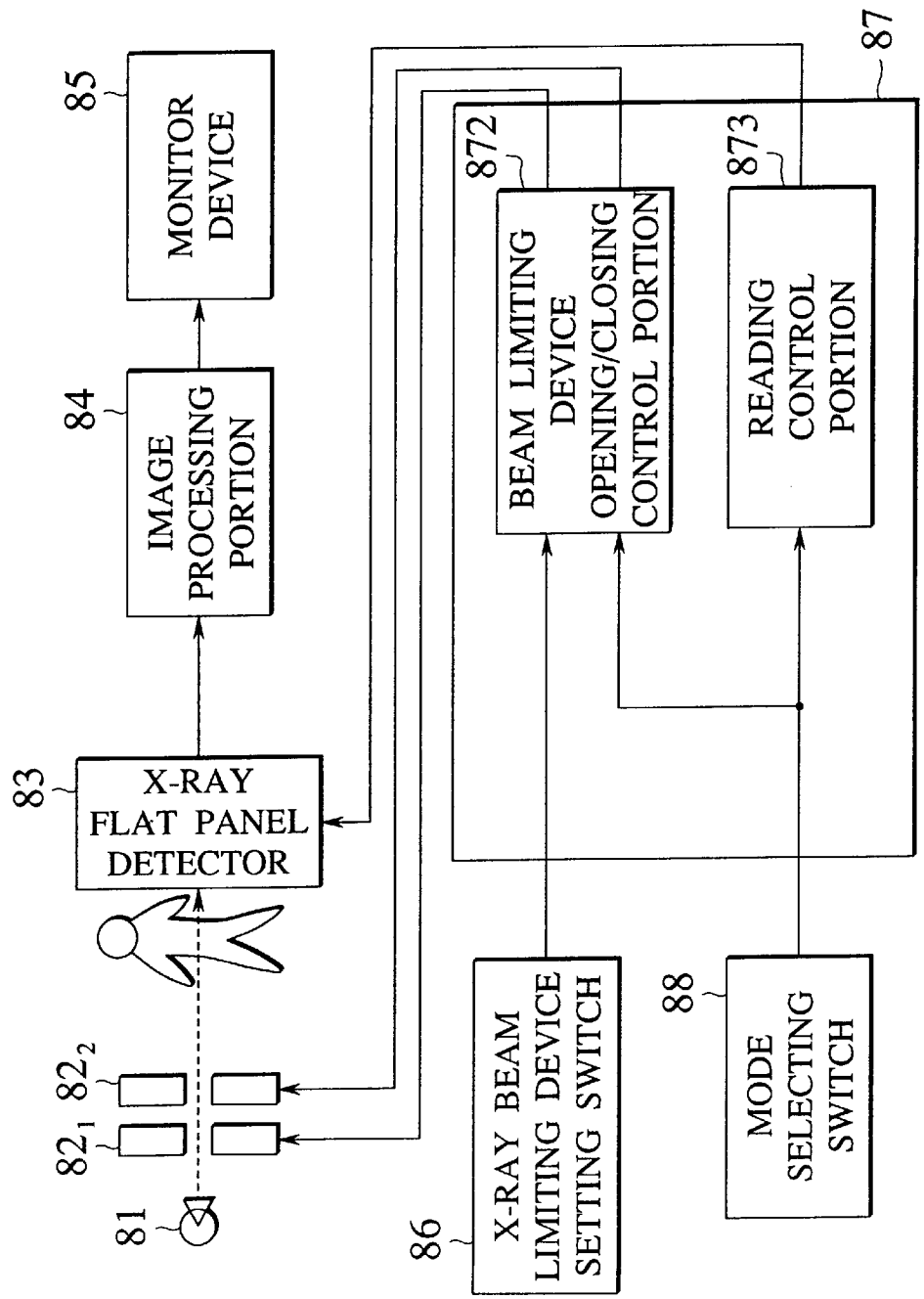
FIG. 26 is a diagram showing a modification of the sixth embodiment.

FIG. 26 shows a modification of the sixth embodiment. This modification has two X-ray beam limiting devices $^{82}1$, 822. The beam limiting device opening/closing control portion 872 controls the X-ray beam limiting device 82, based on the setting on the X-ray beam limiting device setting switch 86 and controls the X-ray beam limiting device 822 based on the setting on the mode selecting switch 88. Consequently, the same effect as in the sixth embodiment can be obtained.

The controls on the opening width and the reading region of the X-ray flat panel detector 83 may be used for radiography as well as fluoroscopy.

Next, the X-ray diagnostic apparatus according to the seventh embodiment will be described.

Although in the X-ray diagnostic apparatus according to the fifth embodiment and sixth embodiment, the reading region of each mode is fixed with respect to the center of the X-ray flat panel detector 83, in the X-ray diagnostic apparatus of the seventh embodiment, the reading region can be set at any position of the X-ray flat panel detector 83.

Figure 27:
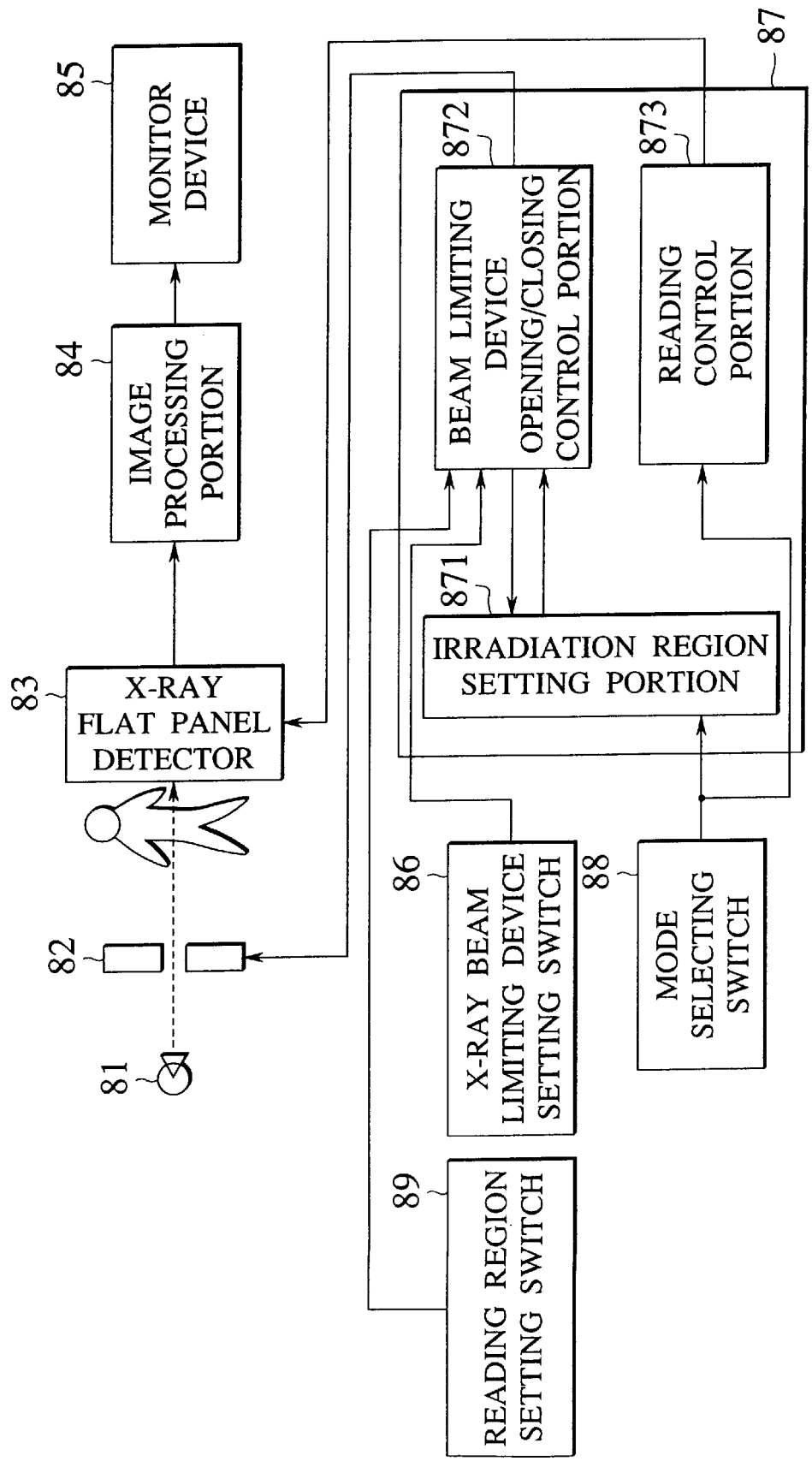
FIG. 27 is a block diagram of the X-ray diagnostic apparatus according to a seventh embodiment of the present invention.

FIG. 27 shows a structure of the X-ray diagnostic apparatus according to the seventh embodiment.

The X-ray diagnostic apparatus according to the seventh embodiment is the aforementioned X-ray diagnostic apparatus of the sixth embodiment provided with a reading region setting switch 89 for an operator to set a reading region at any position of the X-ray flat panel detector 83. A signal from the reading region setting switch 89 is input to the beam limiting device opening/closing control portion 872.

Figure 28:
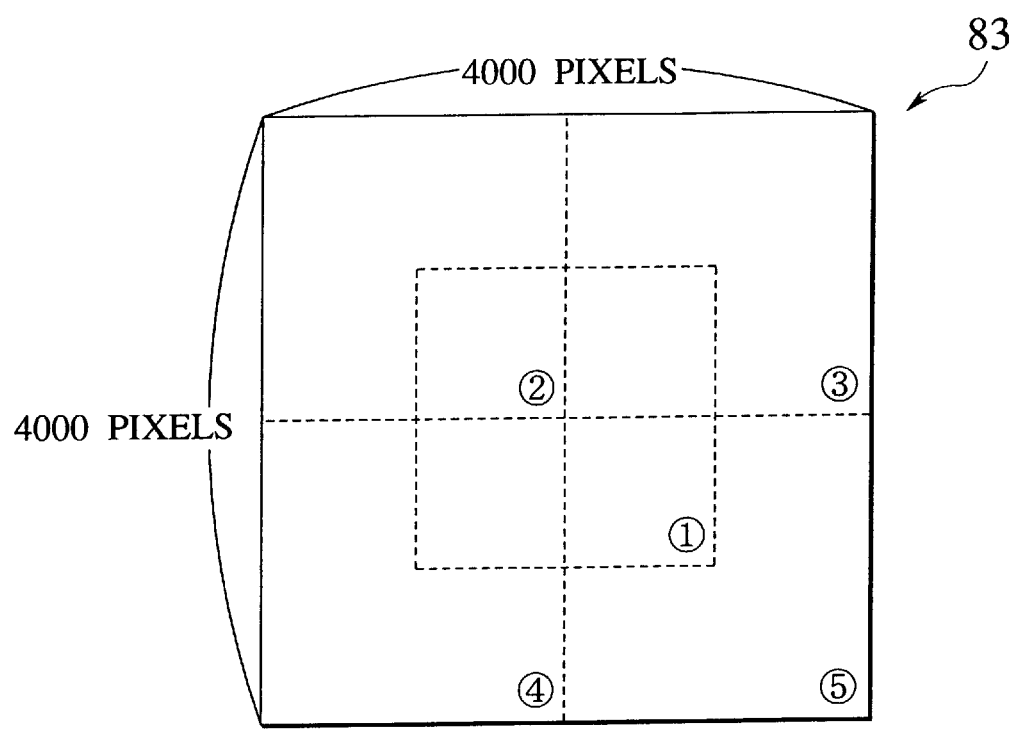
FIG. 28 is a diagram for explaining the X-ray diagnostic apparatus according to the seventh embodiment.

In the X-ray diagnostic apparatus according to the seventh embodiment, as shown in FIG. 28, the entire region of the X-ray flat panel detector 83 is divided into plural reading areas and each of the respective divided reading areas is provided with an area number. An example shown in FIG. 28 indicates a case of the second mode in which five areas ①, ②, ③, ④, ⑤ are provided. In the third mode, the region is divided to its corresponding sizes.

The reading region setting switch 89 is constituted of plural switches for selecting each area number and the operator selects an area number corresponding to a desired reading position when the second or third mode is selected.

The beam limiting device opening/closing control portion 872 controls reading of a fluoroscopy image from a reading area of X-ray flat panel detector 83 selected by the reading region setting switch 89 at a mode specified by the mode selecting switch 88 described with reference to FIG. 25.

When the second mode is selected with the mode selecting switch 88, the X-ray flat panel detector 83 is controlled so as to read a fluoroscopy image in such a condition that totally four pixels of 2 pixels×2 pixels are read out as a single pixel from the reading areas at a position selected by the reading region setting switch 89. If the third mode is selected with the mode selecting switch 88, the X-ray flat panel detector 83 is controlled so as to read a fluoroscopy image from a reading area at a position selected by the reading region setting switch 89.

As a result, a fluoroscopy image at a desired position can be obtained without moving the patient, X-ray flat panel detector and the like, and the same effect as in the fifth and sixth embodiments can be obtained.

Next, an X-ray diagnostic apparatus according to an eighth embodiment will be described.

Although the X-ray diagnostic apparatus according to the fifth-seventh embodiment utilizes the X-ray flat panel detector 83 in which the size of each pixel (sizes in the longitudinal and lateral directions) is the same, the X-ray diagnostic apparatus of the eighth embodiment utilizes an X-ray flat panel detector in which pixels having a different size are mixed.

Figure 29:
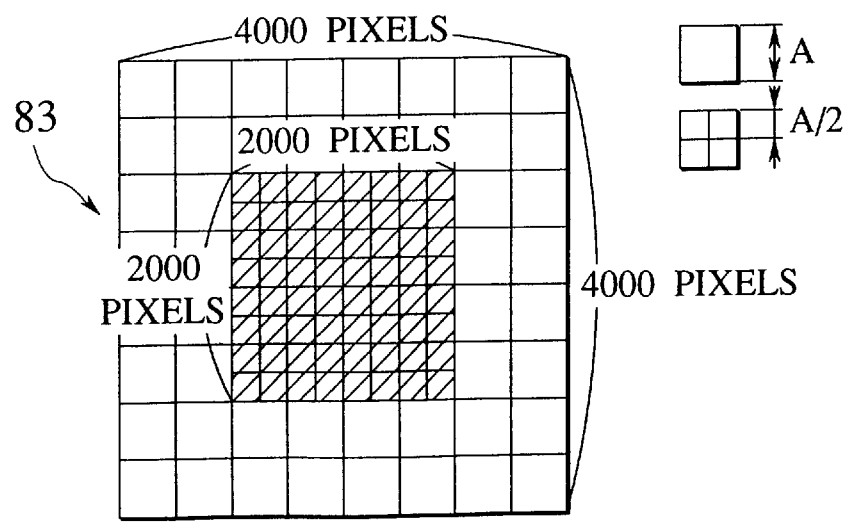
FIG. 29 is a diagram showing an X-ray flat panel detector provided in the X-ray diagnostic apparatus according to an eighth embodiment of the present invention.

The X-ray flat panel detector 83 provided in the X-ray diagnostic apparatus according to the eighth embodiment has a size in which its entire region is 4000 pixels×4000 pixels as shown in FIG. 29. An area (indicated by oblique lines in FIG. 29 referred to as a "high resolution areas) of 2000 pixels×2000 pixels located in the center of that entire region is constituted of pixels having a size ¼ each of pixels forming an area other than this high resolution area (this area is referred to as a "low resolution area"). That is, when the X-ray flat panel detector is produced, it is designed and produced so that pixels having a different size are mixed.

The X-ray diagnostic apparatus of the eighth embodiment has the first mode for reading an image in an entire region of the X-ray flat panel detector 83 and the second mode for reading an image in an area of 2000 pixels×2000 pixels.

If the first mode is specified, the control portion 87 controls so as to read the pixels in the low resolution region as it is and the pixels in the high resolution region are read in such a condition that totally four pixels of 2 pixels×2 pixels are treated as a single pixel. Consequently, in the first mode, a fluoroscopy image of the entire region of the X-ray flat panel detector 83 can be obtained.

If the second mode is specified, the control portion 87 controls so as to read pixels of the high resolution region one by one. As described above, the pixels in the high resolution region have a size which is ¼ the pixel in an area other than the high resolution region. Thus, in the second mode, the field of vision is narrowed to the high resolution region, so that an object portion can be observed at a resolution four times better than the first mode.

Because, in the X-ray diagnostic apparatus of the eighth embodiment, its X-ray flat panel detector itself is constructed of an area having rough pixels and an area having fine pixels, the X-ray flat panel detector can be constituted of a number of pixels smaller than that of the pixels of the X-ray flat panel detector 83 in the X-ray diagnostic apparatus according to the fifth-seventh embodiment, thereby contributing to improvement of yield rate upon production of the X-ray flat panel detector.

In the eighth embodiment also, such reading control may be carried out for radiography as well as for fluoroscopy.

Finally, the X-ray diagnostic apparatus of the present invention can be applied to any type as long as it is an apparatus for obtaining an X-ray image by irradiating a patient with the X-ray like an X-ray CT apparatus.

Although it has been described that the numbers of the pixels in the longitudinal and lateral directions of the X-ray flat panel detector 83 are 4000 pixels×4000 pixels and the processing capacity of the image processing portion 84 at the next step is 1000 pixels×1000 pixels, by picking up concrete numerals for convenience for the description, this is only an example and it is needless to say that various modifications are possible within a scope not departing from the technical philosophy of the present invention.

According to the above described embodiment, in the X-ray diagnostic apparatus using the X-ray flat panel detector in which the spatial resolution is fixed, both radiographies of a wide field of vision and at a high spatial resolution can be carried out corresponding to the processing capacity of the image processing portion at the next step. As a result, a burden on the image processing portion of the next step can be reduced. Therefore, the given apparatus can be constructed at a low cost.

Next, an X-ray diagnostic apparatus of the ninth embodiment of the present invention will be described.

Figure 30:
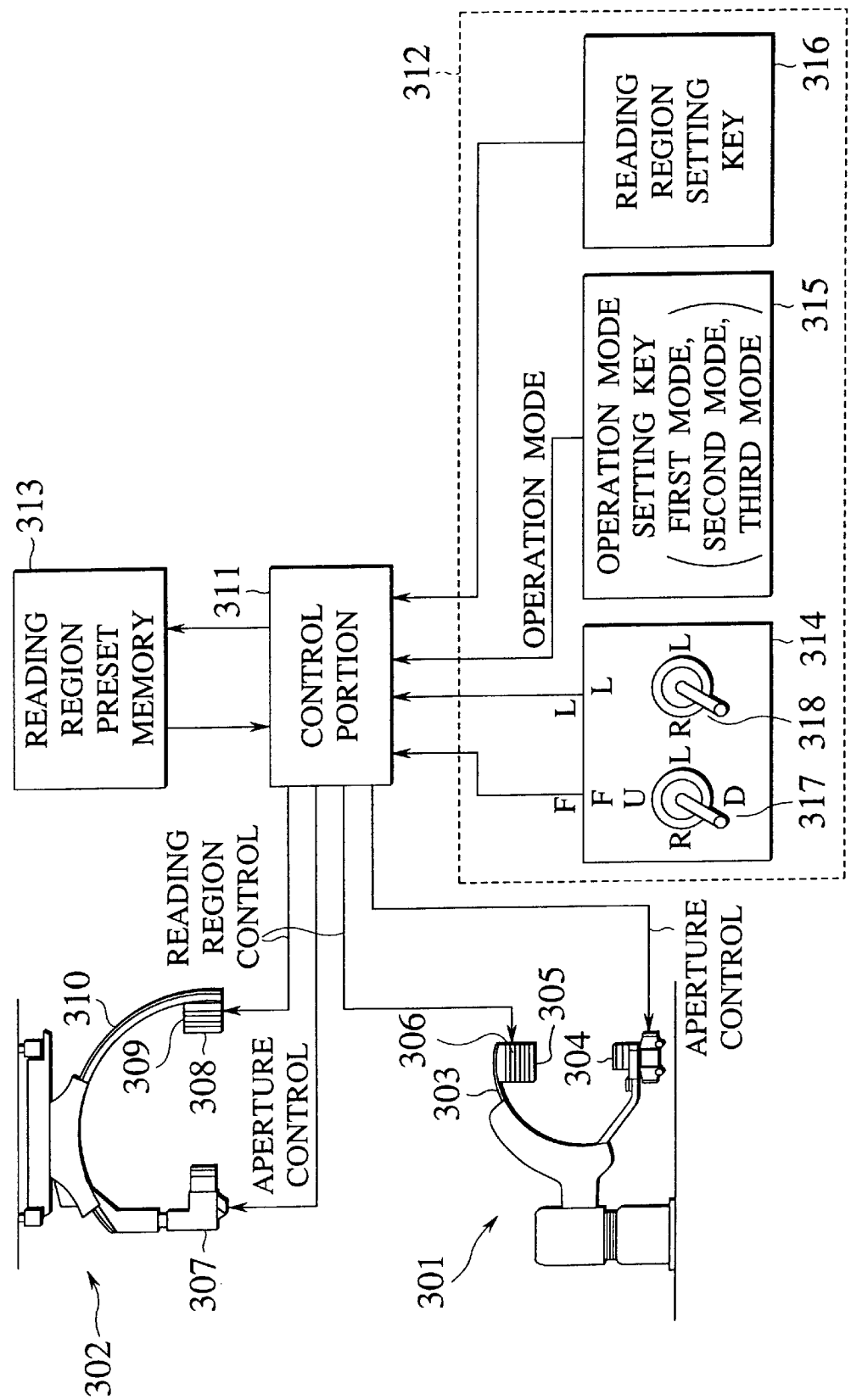
FIG. 30 is a block diagram of a bi-plane inspection apparatus according to a ninth embodiment utilizing the X-ray diagnostic apparatus of the present invention.

The X-ray diagnostic apparatus according to the ninth embodiment can be applied to a bi-plane inspection apparatus for use in mainly cardiac angiography as shown in FIG. 30.

In FIG. 30, the bi-plane inspection apparatus of the ninth embodiment includes a frontal holding device 301 which is a floor placed type X-ray diagnostic apparatus and a lateral holding device 30 which is a mounting type X-ray diagnostic apparatus to be mounted on the ceiling.

The frontal holding device 301 comprises an X-ray beam generating portion 304 and an X-ray detecting portion which is an X-ray flat panel detector 305, provided on both ends of the C letter shaped C-arm 303 such that they face each other, and a moving mechanism 306 for moving the X-ray flat panel detector 305 to a side of the X-ray generating portion 304 or an opposite side of the X-ray generating portion 304.

The lateral holding device 302 comprises an X-ray generating portion 307 and an X-ray flat panel detector 308 which is an X-ray detecting portion, provided on both ends of the Ω letter shaped Ω-arm 310 such that they face each other and a moving mechanism 309 for moving the X-ray flat panel detector 308 to the side of the X-ray generating portion or an opposite side of the X-ray generating portion 307.

The X-ray flat panel detectors 305, 308 have the same structure shown in FIG. 7A as that of the X-ray flat panel detector 7.

The bi-plane inspection apparatus comprises a control portion 311 for controlling the entire portion of the inspection apparatus, an operation portion 312 for operating to specify a desired action and a reading region preset memory 313 in which the size of a reading region in each of the X-ray flat panel detectors 305, 308 to be moved following a stream of contrast medium.

The operation portion 312 includes a vision field moving tool 314 having a frontal joystick 317 (joystick for F) and a lateral joystick 318 for moving the reading region of each of the X-ray flat panel detectors 305, 308 manually, an operation mode setting key 315 for setting an operation mode for moving the reading region, and a reading region setting key 316 for presetting the reading region of each of the X-ray flat panel detectors 305, 308.

Next, an operation of the bi-plane inspection apparatus according to the ninth embodiment having such a structure will be described.

For example, upon carrying out cardiac angiography using this bi-plane inspection apparatus, the operator sets the C-arm of the frontal holding device 301 to RAO30" and the Ω-arm of the lateral holding device 302 to LAO60°, which is a typical positioning for this inspection for a patient placed on a diagnostic bed (not shown).

Next, the operator operates the reading region setting key 316 so as to set the reading region size of each of the X-ray flat panel detectors 305, 308 which follow the stream of contrast medium.

If the operator specifies the reading region size by operating the reading region setting key 316, the control portion 311 displays such a closed line as a circle and rectangle to specify a region on the monitor device. If the operator operates a mouse, a cross key or the like, for example, the control portion 311 moves this closed line vertically or horizontally corresponding to the motion of the mouse or the like. Further, if the operator positions the mouse or cross key on the closed line and operates it vertically or horizontally, the size of the closed line is changed. Then, when the closed line displayed on the monitor is changed to a desired size at a desired position, the operator turns ON a decision key. If the decision key is turned ON, the control portion 311 fetches a size of a reading region set just before.

As a result, the operator can obtain the desired size by expanding or contracting the size of the reading region. The control portion 311 controls the reading on each of the X-ray flat panel detectors 305, 308 according to the size of a reading region set in this way.

In the bi-plane inspection apparatus, not only can a desired size of the reading region can be set as required, but also the size of a reading region frequently used be preset.

Assuming that each of the X-ray flat panel detectors 305, 308 has a totally 9-inch field of vision, a reading region selecting key for specifying the size of a reading region such as 4-inch, 6-inch or the like is provided as the reading region setting key 316. The operator selects a reading region selecting key corresponding to the size of a reading region frequently used from the reading region selecting keys. As a result, the control portion 311 memorizes a reading region size corresponding to the reading region selecting key turned ON in a reading region preset memory 313. When the reading from each of the X-ray flat panel detectors 305, 308 which will be described later is controlled, that reading control is carried out with this preset reading region size.

If the setting or instruction on the reading region size is terminated, the operator selects a mode for moving the reading region by operating the operation mode setting key 315.

As the operation mode which can be set with this operation mode setting key 315, totally three modes, the first-third modes are provided. The first mode is a mode for operating the joysticks 317, 318 of the vision field moving tool 314 independently to move each of the X-ray flat panel detectors 305, 308 independently, the second mode is a mode for moving respective reading regions of the X-ray flat panel detectors 305, 308 interlockingly by only operating the frontal joystick 317, and the third mode is a mode for moving the reading region of the X-ray flat panel detector 305 by only operating the frontal joystick 317 in the direction of the operation of the joystick 317 and moving the reading region of the X-ray flat panel detector 308 in a direction perpendicular to the direction of the operation of the joystick 317.

Next, if the operator sets a desired mode with this operation mode setting key 315, a fluoroscopy specifying key (not shown) is turned ON to start fluoroscopy. If the fluoroscopy specifying key ON is detected, the control portion 311 controls the X-ray generating portions 304, 307 of the holding devices 301, 302 so as to irradiate a small amount of the X-ray to the patient.

The X-ray flat panel detectors 305, 308 of the holding devices 301, 302 fetch an X-ray image formed by the irradiation of the X-ray.

Concretely speaking, each of the X-ray flat panel detectors 305, 308 reflects visible light other than the X-ray passing through the patient by the light reflective layer 48 shown in FIG. 8. As a result, only the X-ray is entered into the fluorescent material 49 via the light reflective layer 48. The fluorescent material 49 converts the entered X-ray to visible light and then this visible light is entered into a photo diode via the transparent protective film 50, the second polyimide resin layer 63 and transparent electrode 60.

The photo diode forms an electric charge corresponding to a light amount of this visible light and supplies it to the aforementioned accumulative capacitor.

The control portion 311 controls the scanning line driving portion 34 and multiplexer 38 of each of the X-ray flat panel detectors 305, 308 so as to ensure a reading region size stored in the reading region setting key 316 or reading region preset memory 313 shown in FIG. 30

As a result, the electric charge stored in each of the accumulative capacitors of the X-ray flat panel detectors 305, 308 is read out to each line in the unit of a pixel as an image signal via the signal lines 36-1, 36-2, . . . 36-n, selected by the multiplexer 38 and supplied to the monitor device via the output terminal 39.

Figure 31:
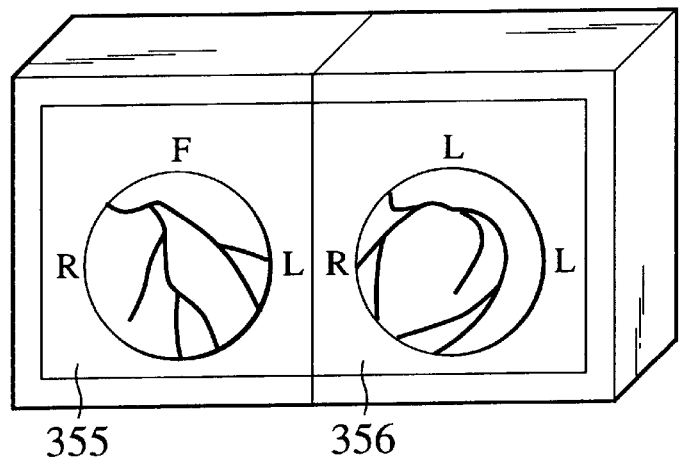
FIG. 31 is a diagram showing a monitor device in which fluoroscopy images taken by a lateral holding device and a frontal holding device are displayed.

Because the read out image signal is proportional to the exposure of the X-ray, as shown in FIG. 31, the X-ray image fetched by the X-ray flat panel detectors 305, 308 can be displayed on the monitor devices 355, 356 of the holding devices 301, 302.

Next, the operator recognizes a flow of the contrast medium flowing through a cardiac blood vessel displayed on each of the monitor devices 355, 356 and operates each of the joysticks 317, 318 following the flow of the contrast medium.

As described above, the operation mode for the operation of the joysticks 317, 318 is selected by the operation mode setting key 315 from the first-third modes. When the first mode is selected, the control portion 311 controls to move each of the reading regions of the X-ray flat panel detectors 305, 308 independently corresponding to each operation of the joysticks 317, 318. If the second mode is selected, the control portion 311 controls to move the reading regions of the X-ray flat panel detectors 305, 308 interlockingly by operating only the frontal joystick 317. If the third mode is selected, the control portion 311 controls to move the reading region of the X-ray flat panel detector 305 in the direction of the operation of the joystick 317 by operating only the frontal joystick 317 and then controls to move the reading region of the X-ray flat panel detector 308 in a direction perpendicular to that of the joystick 317.

Further, the control portion 311 controls the X-ray beam limiting device provided in the X-ray generating portions 304, 307 with a control on the moving of the reading region, so as to irradiate the X-ray to the reading region subjected to this moving control.

In a case where there is a correlation between a moving direction and a moving amount of each reading region of each of the holding devices 301, 302, the operator selects the third mode.

If the third mode is selected, the control portion 311 controls to move the reading region of the X-ray flat panel detector 305 corresponding to the direction of the operation of the frontal joystick 17 and simultaneously controls to move the reading region of the X-ray flat panel detector 308 in the direction perpendicular to the direction of the operation of the joystick 317. Further, the control portion 311 controls the X-ray beam limiting device provided on each of the X-ray generating portions 304, 307 so as to irradiate the X-ray to only the reading region of each of the X-ray flat panel detectors 305, 308.

Figure 32:
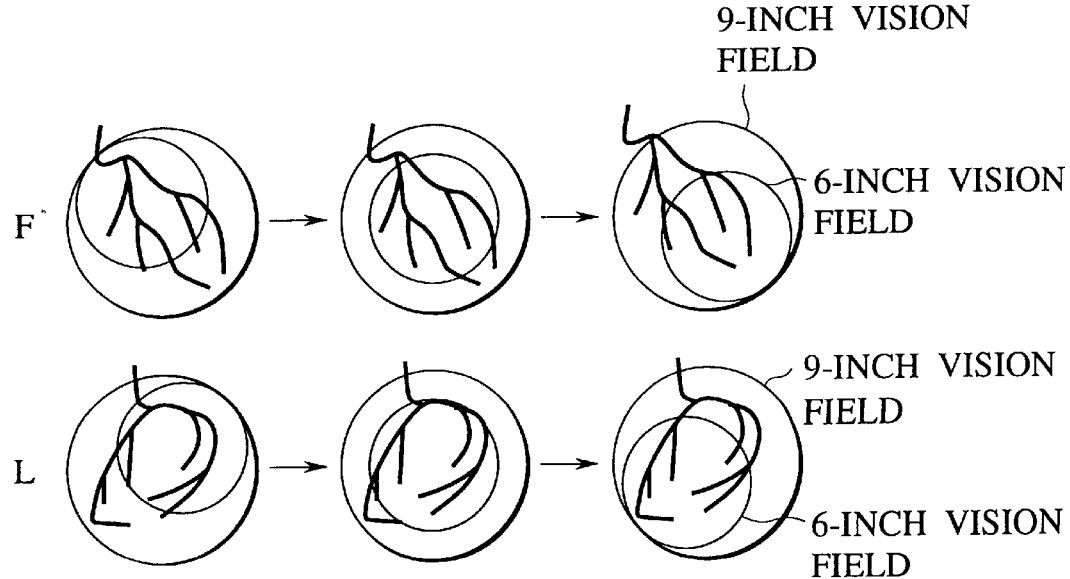
FIG. 32 is a diagram showing a condition in which each fluoroscopy image of the lateral holding device and frontal holding device is displayed following a flow of contrast medium.

Consequently, the moving of the reading region of each of the X-ray flat panel detectors 305, 308 can be controlled by only operating the frontal joystick 317, so that an image in each of the holding devices 301, 302 following a stream of the contrast medium as shown in FIG. 32 can be obtained. Further, it is possible to prevent an inconvenience that the X-ray is irradiated on an unnecessary place other than the reading region, and thereby an unnecessary exposure on the patient is being reduced.

The BP inspection apparatus is provided with the joysticks 317, 318 for frontal and lateral moves to control the moving of the reading region. Unless the moving amounts in the back and forth directions of the reading region controlled by the joysticks 317, 318 are set to the same quantity in each of the holding apparatuses 301, 302, there occurs a deviation in each image (region of interest) on the monitor device.

Thus, in the bi-plane inspection apparatus, the moving amounts in the back and forth directions are made common. If one of the joysticks 317, 318 is operated, the control portion 311 controls to move the reading region corresponding to the other joystick by the same amount as the moving amount in the back and forth directions produced by that operation.

As a result, it is possible to prevent such an inconvenience that there occurs a deviation in each image (region of interest) displayed on the monitor due to a deviation in the moving amount in the back and forth directions produced by the operation of the joysticks 317, 318.

As for each image read out from each of the X-ray flat panel detectors 305, 308, displayed on the monitor, generally, a left portion of the region of interest is displayed on the right side of the display screen and a right portion thereof is displayed on the left side of the display screen. Thus, if the right portion of a region of interest is so constructed to be moved to the center of the monitor when each of the joysticks 317, 318 is turned to the right, namely, the region of interest located in an opposite direction to the operation direction is so constructed to be moved to the center of the monitor, a feeling of disharmony is produced.

Thus, when the control portion 311 moves the reading region of each of the X-ray flat panel detectors 305, 308, it controls the reading so that the region of interest is moved in the operation directions of the joysticks 317, 318. As a result, an image corresponding to the operation direction of the joysticks 317, 318 can be displayed on the monitor.

As evident from the above description, in the bi-plane inspection apparatus of the ninth embodiment, the reading regions of the X-ray flat panel detectors 305, 308 are controlled corresponding to the operation of the joysticks 317, 318 so as to take radiography following a stream of the contrast medium.

Therefore, the cardiac angiography can be conducted by only the operation of the joysticks 317, 318 without operating the holding devices 301, 302 and the diagnostic bed. Therefore, in the BP inspection such as cardiac angiography, an operation following a flow of the contrast medium can be carried out well enough by only an operator so that the best X-ray image can be obtained securely without a possibility of failure.

Further, because the fluoroscopy position on the patient is changed by changing the reading region of the X-ray flat panel detector, motions of the C-arm 303, $\Omega$-arm 310 and top panel on which the patient is to be placed which may occur when the fluoroscopy position is changed can be reduced. Because the motions of the C-arm 303, $\Omega$-arm 310 and top panel on which the patient is to be placed when the fluoroscopy position is changed can be reduced, such an accident as a collision which may occur when the arms or top panel is moved can be reduced.

Next, the BP inspection apparatus according to the tenth embodiment of the present invention will be described.

Although in the bi-plane inspection apparatus of the ninth embodiment, the operator operates the joysticks 317, 318 watching images displayed on the X-ray flat panel detectors 305, 308 so as to control the moving of the reading region, the bi-plane inspection apparatus of the tenth embodiment controls the moving of the reading region along a predetermined path to thereby simplify the moving operation.

That is, usually the positioning of each of the holding devices 301, 302 is determined depending on an inspection content, so that there is not much difference depending on the patient in a way of flow of the contrast medium. Therefore, the bi-plane inspection apparatus of the tenth embodiment is so constructed as to contain a moving pattern memory 357 memorizing a moving pattern of the reading region depending on the content of each inspection.

Further, the operation portion 312 includes an inspection content setting portion 356 for setting the inspection content and the control portion 311 fetches contrast medium injection information (injection information) from an injector 355 for injecting the contrast medium to the patient.

Figure 33:
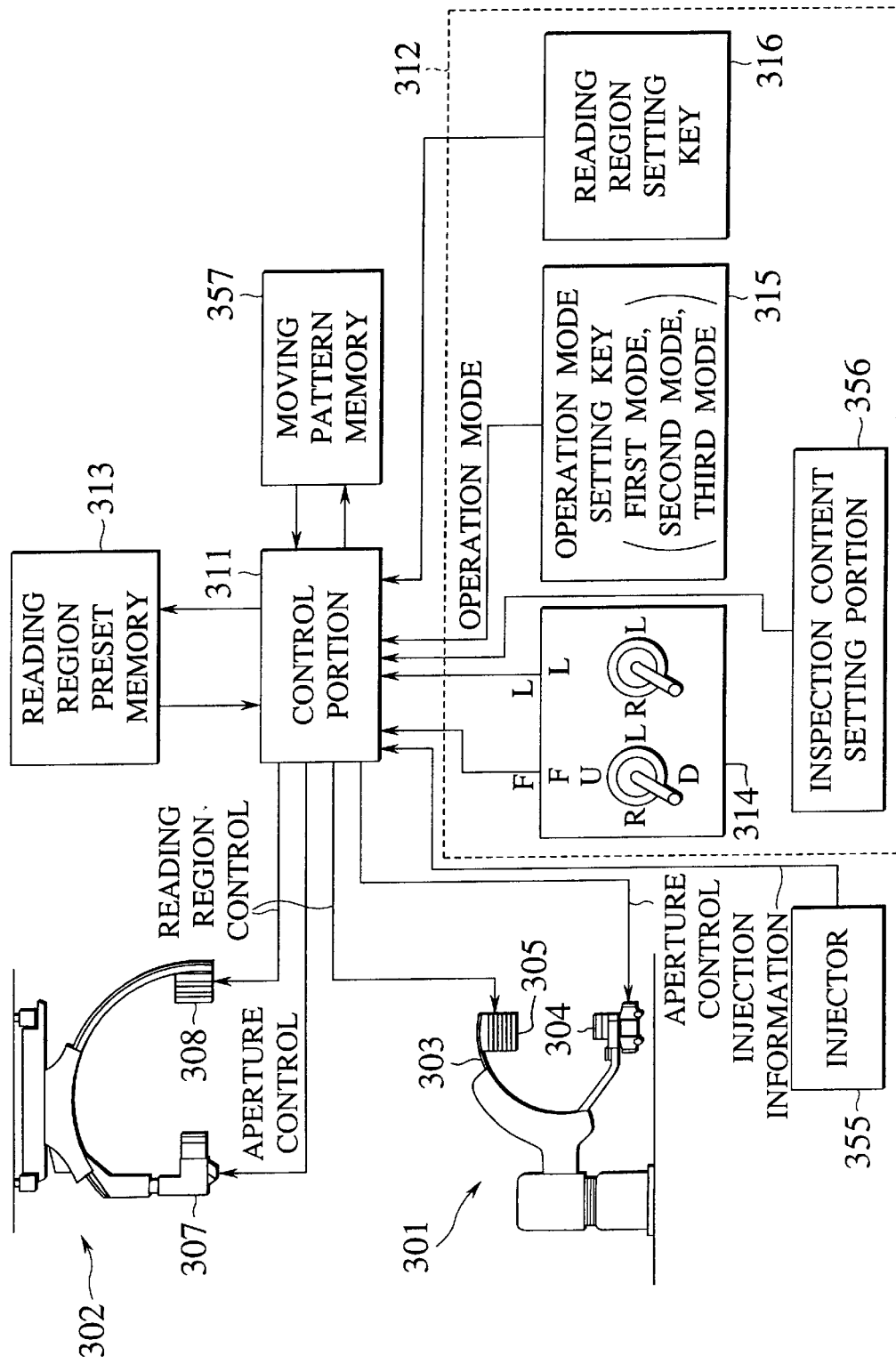
FIG. 33 is a block diagram of a bi-plane inspection apparatus according to a tenth embodiment utilizing the X-ray diagnostic apparatus of the present invention.

Because the other structure is the same as the bi-plane inspection apparatus of the ninth embodiment, in FIG. 33, the same reference numerals are attached to portions carrying out the same operations so as to avoid a duplicated description.

In such a bi-plane inspection apparatus of the tenth embodiment, the operator specifies an inspection content using the inspection content setting portion 356. The inspection content setting portion 356 is provided with a plurality of selection keys for specifying an inspection content corresponding to each inspection and the operator turns ON a desired selection key.

If the ON operation on the selection key is detected, the control portion 311 reads out a moving pattern program of a reading region corresponding to that selection key from the moving pattern memory 357. This control portion 311 is supplied with injection information indicating an injection condition of the contrast medium from the injector 355.

The control portion 311 detects a condition of flow of the contrast medium corresponding to injection information and controls the moving of the reading region in each of the X-ray flat panel detectors 305, 308 based on a moving pattern program.

As a result, only by selecting an inspection content by operating the inspection content setting portion 356, the moving of the reading region can be automatically controlled following the flow of the contrast medium. The same effect as in the bi-plane inspection apparatus of the ninth embodiment can be ensured.

In a case of a special inspection, a technique similar to bolus chasing conducted in lower limb angiography may be used. Next, a bi-plane inspection apparatus according to an eleventh embodiment will be described.

Although in the bi-plane inspection apparatus of the tenth embodiment, the moving of each reading region is controlled along a path preliminarily programmed depending on a set inspection content, the bi-plane inspection apparatus of the eleventh embodiment fetches image information at real time and controls the moving of the reading region corresponding to a change in the pixel value of this image.

Figure 34:
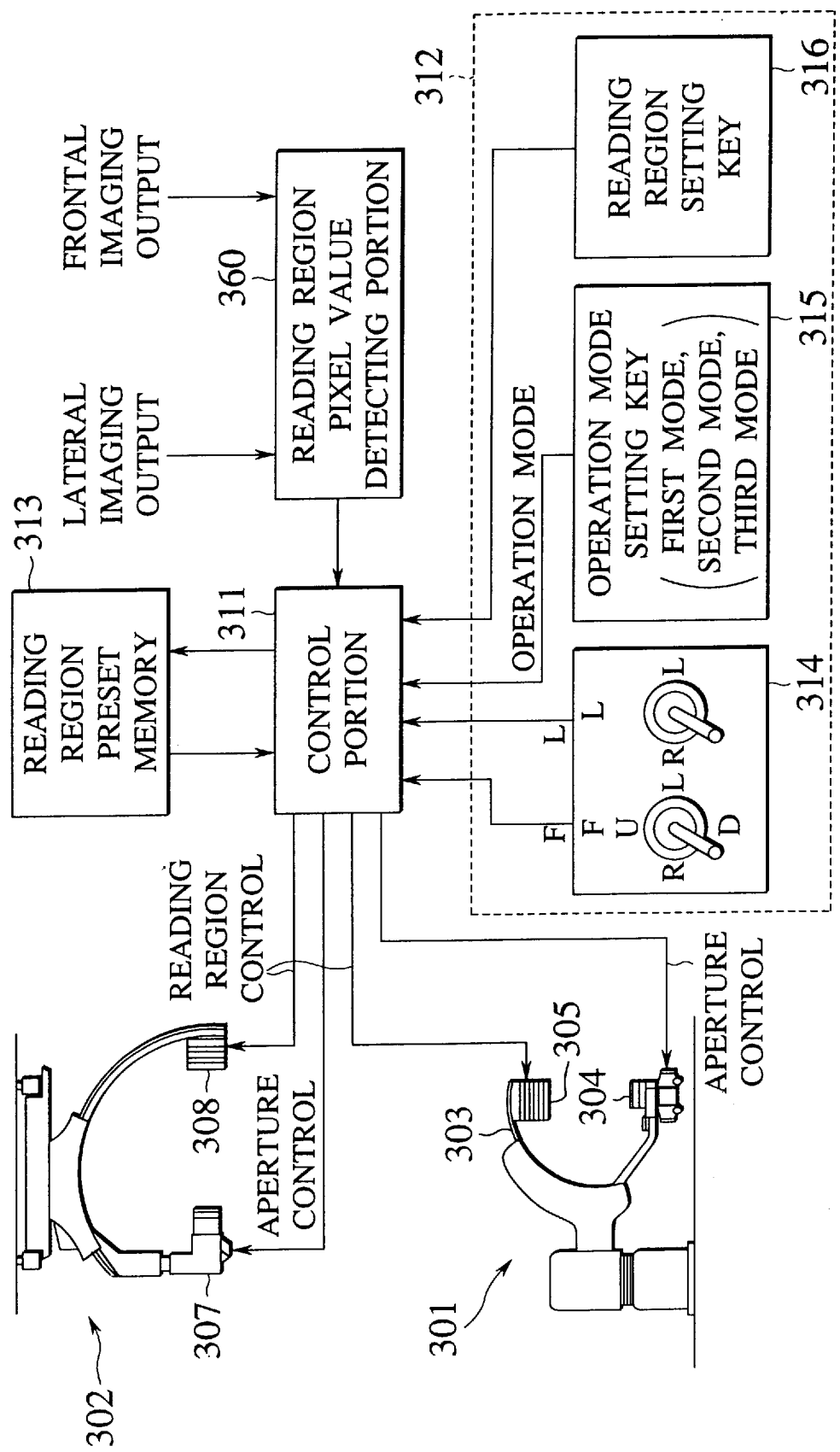
FIG. 34 is a block diagram of a bi-plane inspection apparatus according to an eleventh embodiment utilizing the X-ray diagnostic apparatus of the present invention.

That is, the bi-plane inspection apparatus of the eleventh embodiment detects a change in pixel value of each image information from each of the X-ray flat panel detectors 305, 308 as shown in FIG. 34 and includes a reading region pixel value detecting portion 360 for supplying this inspection output to the control portion 311.

Because the other structure is the same as that of the bi-plane inspection apparatus according to the ninth embodiment, the same reference numerals are attached to portions performing the same operation in FIG. 34, thereby avoiding a duplicated description.

In the bi-plane inspection apparatus of the eleventh embodiment, the control portion 311 divides the entire image region of each of the X-ray flat panel detectors 305, 308 vertically and horizontally to four division areas, controls the reading of an image in each division area at every predetermined time and supplies the image data to the reading region pixel value detecting portion 360.

The reading region pixel value detecting portion 360 integrates pixel values for each image in each division area supplied at each predetermined time, and when that integrated pixel values exceed a predetermined level (or falls below a predetermined level), determines that the contrast medium has flown into a blood vessel located in that division area, and controls to move the reading region to that division area.

Concretely, if the contrast medium flows along the blood vessel, the pixel values of an image in that division area gradually begin to have a white level. Thus, if the pixel values are integrated, total pixel values of an image where the contrast medium beings to flow into the blood vessel gradually become a lower value. Therefore, the control portion 311 controls to move the reading region following that division area having the low pixel value.

Figure 35:
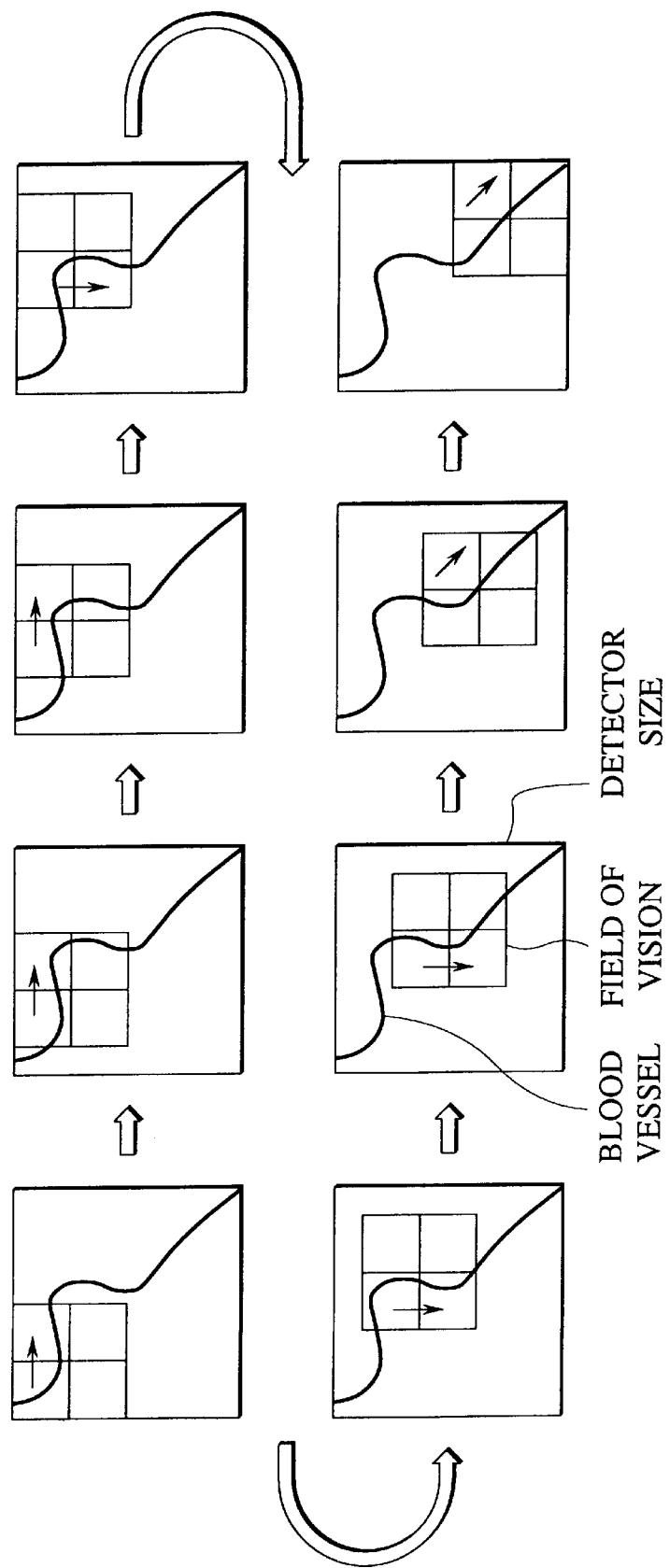
FIG. 35 is a diagram for explaining an operation for automatically making a fluoroscopy field follow a flow of the contrast medium by moving the fluoroscopy field according to a pixel value of a fluoroscopy image in a bi-plane inspection apparatus according to the eleventh embodiment.

As a result, as shown in FIG. 35, the moving of the reading region can be automatically carried out following the flow of the contrast medium, so that the same effect as the bi-plane inspection apparatus of the ninth embodiment can be obtained.

Although, in the description of the eleventh embodiment, each of the X-ray flat panel detectors 305, 308 is divided to four division areas, it is permissible to divide to a desired number of divisions like 9 divisions or 16 divisions. If the number of divisions is increased, the accuracy of tracing along the blood vessel is improved. If the direction of tracing along the blood vessel is limited, it is permissible to divide to two portions.

The image in the reading region may be displayed as it is without being enlarged or may be displayed in enlargement.

Upon displaying in enlargement, it is desirable to preliminarily form a pixel density in each of the X-ray flat panel detectors 305, 308 so as to obtain a necessary resolution.

Finally, although a case in which the X-ray diagnostic apparatus of the present invention is applied to the bi-plane inspection apparatus has been described, it is needless to say that the present invention may be modified in various ways within a scope not departing from a technical philosophy relating to the present invention such as an application of the present invention to single plane inspection apparatus.

In the X-ray diagnostic apparatus of the above described embodiments, the operation thereof can be simplified. Thus, the bi-plane inspection such as cardiac angiography can be operated by only a single person following a flow of the contrast medium, so as to obtain the best X-ray image securely without any failure.

Next, the X-ray diagnostic apparatus according to the twelfth embodiment of the present invention will be described.

Figure 36:
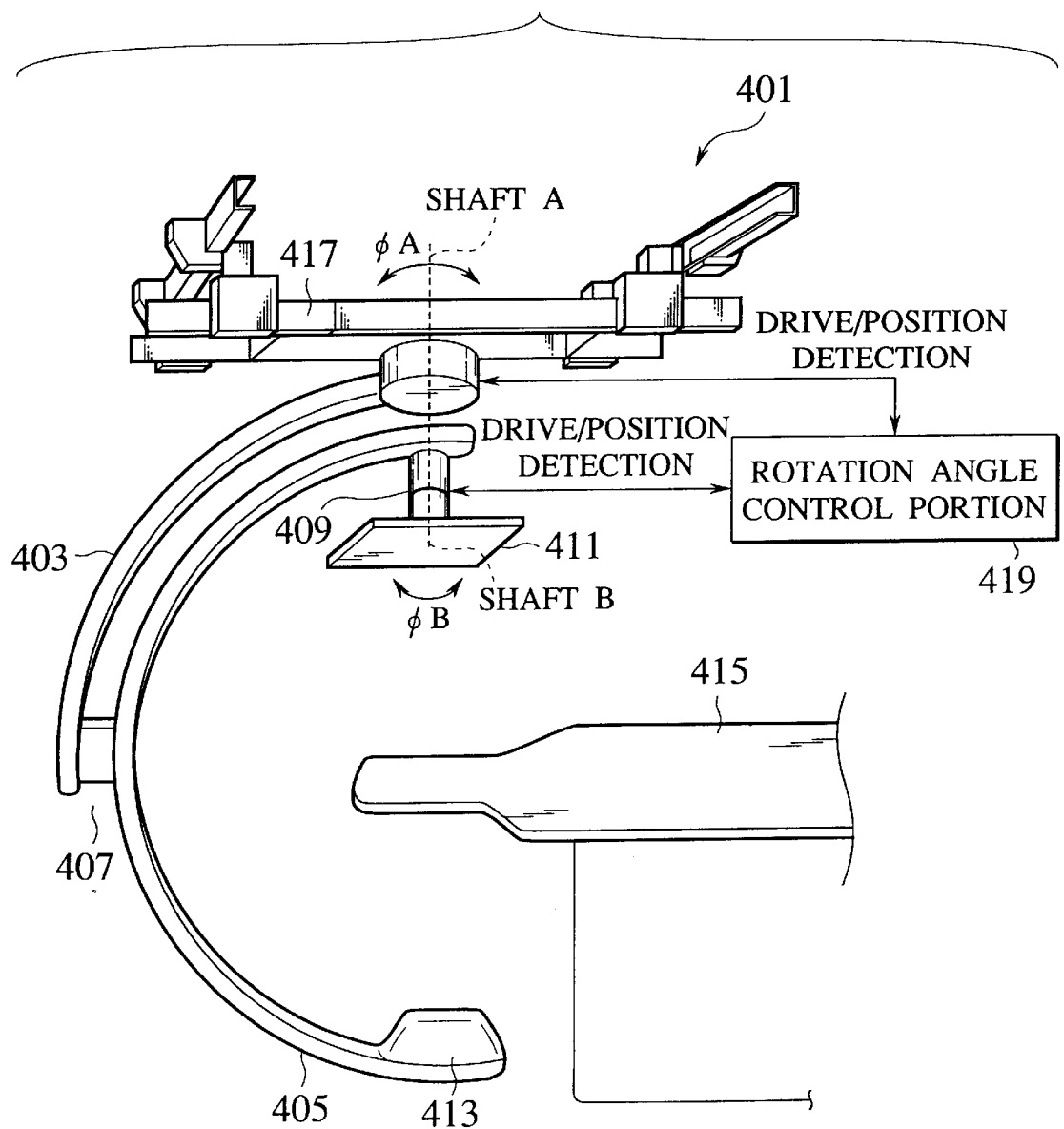
FIG. 36 is a structural diagram of the X-ray diagnostic apparatus according to a twelfth embodiment of the present invention.
Figure 37:
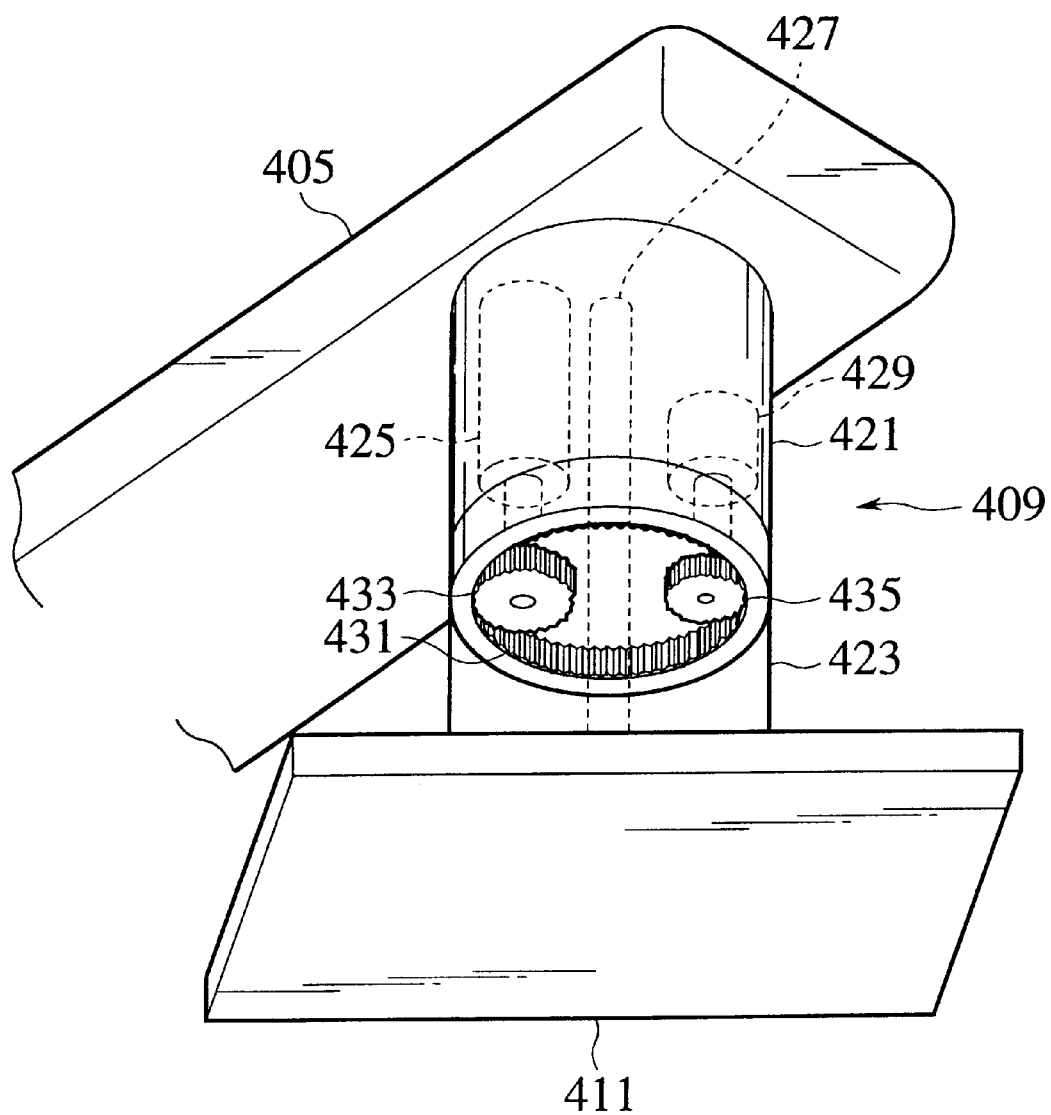
FIG. 37 is an enlarged sectional view of major parts of the X-ray diagnostic apparatus of the twelfth embodiment.
Figure 38:
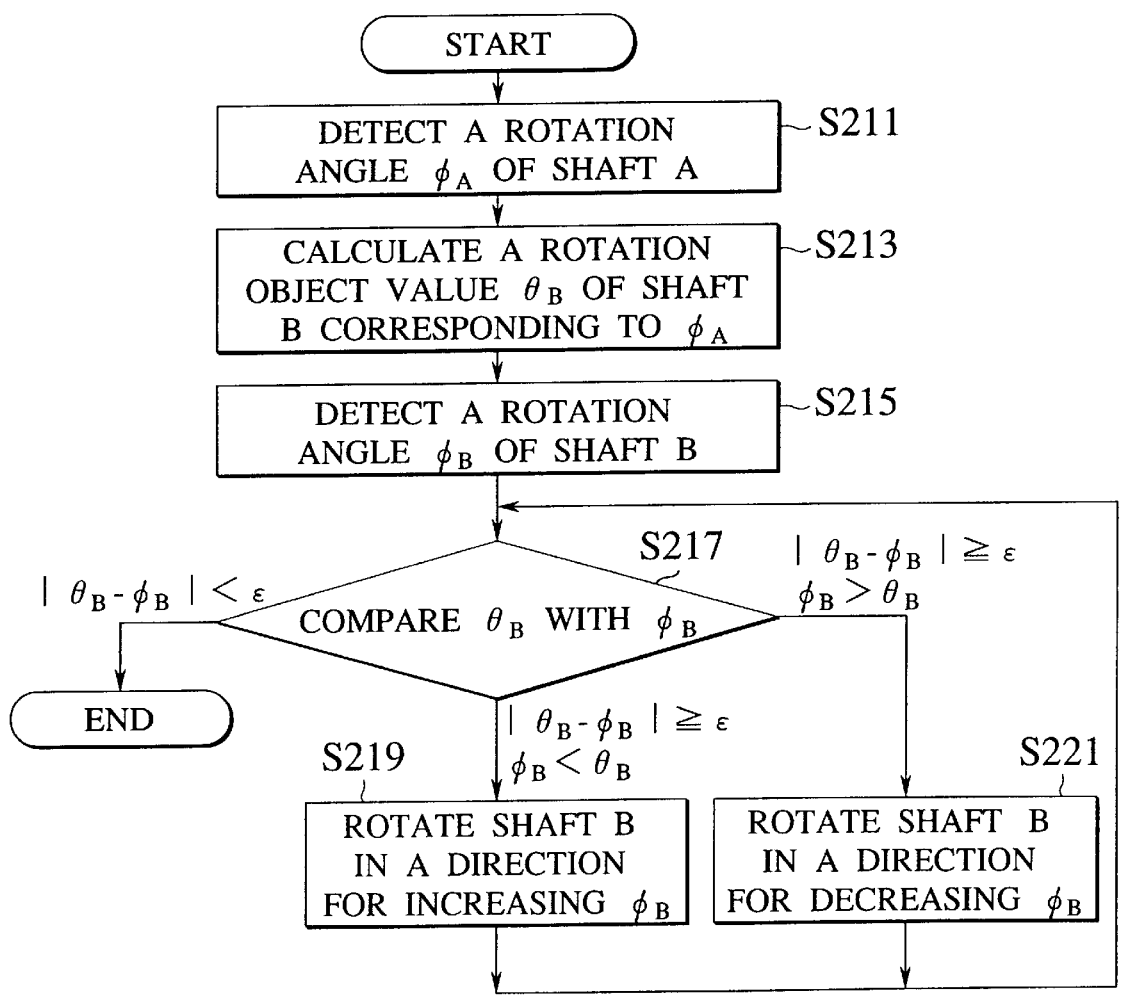
FIG. 38 is a flow chart for explaining an operation of the X-ray diagnostic apparatus according to the twelfth embodiment.
Figure 39:
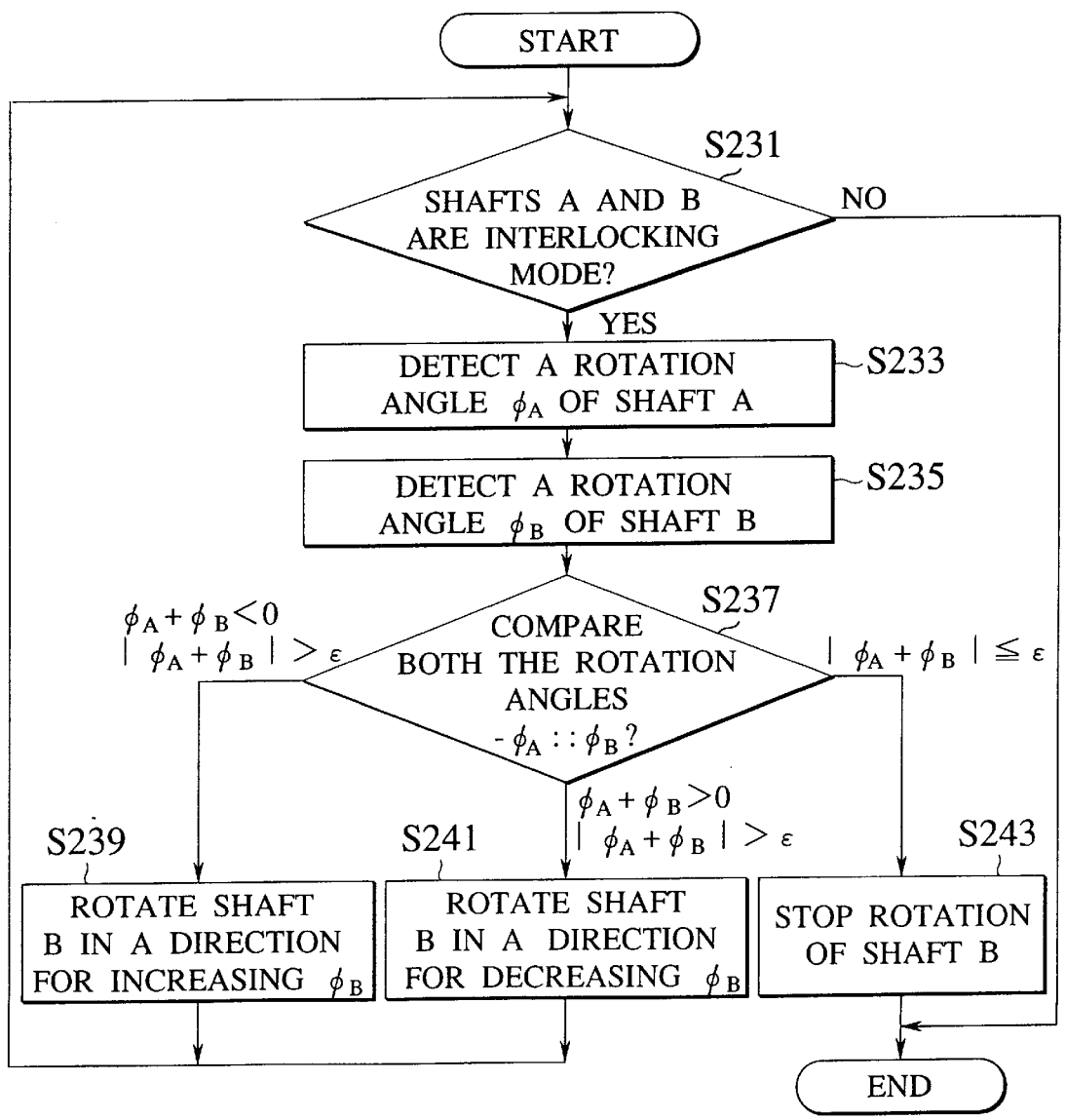
FIG. 39 is a flow chart for explaining an operation of the X-ray diagnostic apparatus according to the twelfth embodiment.

FIG. 36 is an entire configuration diagram of the X-ray diagnostic apparatus of the twelfth embodiment, FIG. 37 is an enlarged partial sectional view of the major parts thereof and FIGS. 38, 39 are flow charts showing an operation of the X-ray diagnostic apparatus of the present invention.

As shown in FIG. 36, the X-ray diagnostic apparatus 401 of this embodiment comprises a supporting device 407 as a holding means constituted of an arch arm 403 and a C-arm 405, a joint portion 409 provided at a top end of the C-arm 405, an X-ray flat panel detector 411 as an X-ray generating means rotatably supported by the joint portion 409, an X-ray tube 413 as an X-ray generating means provided at a bottom end of the C-arm 405, a diagnostic bed 415, a hoisting rack 417 for hoisting the supporting device 417 from a ceiling, a rotation angle control portion 419 and an X-ray tube power unit (not shown) and a monitor device (not shown).

The X-ray flat panel detector 411 is a radiography means in which a plurality of pixels for converting the X-ray to electric signals and accumulating it are disposed in a matrix. An image signal of each pixel corresponding to an exposure of impinging X-ray is output and this image signal is directly displayed on the monitor device or subjected to an appropriate image processing and then displayed on the monitor device. The X-ray flat panel detector may be a direct conversion type or an indirect conversion type.

The top end of the arch arm 403 of the supporting device 407 is journaled rotatably on a horizontal plane, by the hoisting rack 417 capable of traveling freely longitudinally and laterally on a ceiling. A center portion of the C-arm 405 is connected to a bottom end of the arch arm 403 such that it is slidable and rotatable. The X-ray flat panel detector 411 is provided rotatably on a top end of the C-arm 405 via the joint portion 409 and the X-ray tube 413 as an X-ray source is provided at a bottom end of the C-arm 405 so that it opposes the X-ray flat panel detector 411.

The rotation angle control portion 419 detects an rotation angle $\phi A$ of the top end of the arch arm 403 relative to the jointing rack 417 and a rotation angle $\phi B$ of the joint portion 409 between the C-arm 405 and the X-ray flat panel detector 411 is controlled so as to eliminate a rotation of this $\phi A$.

FIG. 37 is an enlarged partial sectional view showing a detail of the joint portion and the same reference numerals are attached to the same components as in FIG. 36.

The joint portion 409 connects the top end of the C-arm 405 to the X-ray flat panel detector 411 such that it is rotatable and comprises an upper cylinder 421 and a lower cylinder 423, two divided portions rotatable relative to each other.

The upper cylinder 421 of the joint portion 409 is fixed to the top end of the C-arm 405 and contains a stepping motor 425, a rotation shaft member 427 and a rotary encoder 429 therein.

The lower cylinder 423 is journaled rotatably around the rotation shaft member 427 and the X-ray flat panel detector 411 is provided on a bottom end thereof. A ring gear 421 is formed on an inner periphery of a top end of the lower cylinder 423. A pinion 433 meshing with the ring gear 431 is provided on a shaft of the stepping motor 425. By normal and inverse rotations of the stepping motor 425, the lower cylinder 423 can be rotated in normal and inverse directions with the X-ray flat panel detector 411.

A pinion 435 connected to the rotary encoder 429 is meshed with the ring gear 431 so that a rotation angle of the ring gear 431 or a rotation angle 0 B of the X-ray flat panel detector 411 relative to the C-arm 405 can be detected.

Further, a signal cable (not shown) for connecting the X-ray flat panel detector 411 to the monitor device or image processing device and a power supply line (not shown) of the X-ray flat panel detector 411 are connected via a spiral code or slip ring provided inside the rotation shaft member 427 or therearound.

Next, an operation of the X-ray diagnostic apparatus according to this embodiment will be described with reference to FIGS. 36, 37.

When a patient placed on the diagnostic bed 415 is inspected, the shaft A of the supporting device 407 shown in FIG. 36 is rotated, so that the supporting device 407 is rotated around the patient. Therefore, the X-ray detection system can be inserted in any direction relative to the patient. Thus, the operator can access the patient from any direction.

At this time, corresponding to a rotation of the shaft A of the supporting device 407, the joint portion 409 provided between the supporting device 407 and X-ray flat panel detector 411 is rotated. The rotation control portion 419 for controlling the rotation angle reads a signal from the rotation angle detecting means (not shown) provided on the shaft A of the supporting device 407, and calculates a rotation angle of the joint portion 409 so as to always direct the X-ray flat panel detector 411 to the patient or diagnostic bed and move it.

As a result, if the supporting device 407 is rotated at any angle ($\phi$A) relative to the shaft A, the X-ray flat panel detector 411 is rotated at the same rotation angle $\phi$B in an opposite direction relative to the supporting device 407 by a rotation mechanism of the joint portion 409, so that both the rotations eliminates each other. As a result, the X-ray flat panel detector 411 is always directed in the same direction relative to the patient. Thus, if the supporting device is rotated, the X-ray flat panel detector is seen as fixed relative to the patient so that the patient does not feel a fear.

As for a direction of an image to be radiographed, because the X-ray flat panel detector is fixed relative to the patient, the X-ray image on the monitor screen is not rotated even if the supporting device is moved relative to the shaft A, so that an excellent image for inspection can be obtained.

Next, this operation will be described with reference to a flow chart of FIG. 38.

In this description, the rotation angle is a real number with a sign. For example, a clockwise rotation angle with respect to a reference rotation angle and a counterclockwise rotation angle are assumed to be + and − respectively. Further, a rotation angle less than a control error determined to produce substantially no difference in rotation angle is assumed to be a convergence determining value $\epsilon$.

First of all, the rotation angle $\phi$A of the shaft A is detected (step S211). Next, an object rotation value $\theta$B of the shaft B corresponding to $\phi$A is calculated (step 213). Next, the rotation angle $\phi$B of the shaft B is detected (step S215) and the object rotation angle $\theta$B is compared with the rotation angle $\phi$B (step S217). As a result of the comparison, if $|\theta B-\phi B|<\epsilon$ (convergence determining value), it is assumed that an object has been reached and the operation is terminated.

As a result of the comparison at step S217, if $|\theta B-\phi B|\geq\epsilon$ and $\phi B<\theta B$, the shaft B is rotated in a direction for increasing the $\theta$B (step S219) and then the processing returns to step S217.

As a result of the comparison at step S217, if $|\theta B-\phi B|\geq\epsilon$ and $\phi B>\theta B$, the shaft B is rotated in a direction for decreasing the $\phi$B (step S221) and the processing returns to step S217.

FIG. 39 is a flow chart showing a modification of the rotation angle control shown in FIG. 38.

First of all, whether or not the shafts A and B are an interlocking mode or not is determined (step S231). The interlocking mode refers to a mode for controlling the shaft B by control of the rotation control portion 419 so as to eliminate a rotation of the shaft A.

Next, the rotation angle $\phi$A of the shaft A is detected (step S233) and the rotation angle $\phi$B of the shaft B is detected (step S235). Next, both the rotation angles are compared with each other (step S237) and if this result is that ($\phi$A+$\phi$B)<0 and $|\phi A+\phi B|>\epsilon$ (convergence determining value), the shaft B is rotated in a direction for increasing the $\phi$B (step S239) and the processing returns to step S231.

If ($\phi$A+$\phi$B)>0 and $|\phi A+\phi B|>\epsilon$ (convergence determining value) in a determination of step 237, the shaft B is rotated in a direction for decreasing the $\phi$B (step S241) and the processing returns to step S231.

If $|\phi A+\phi B|<\epsilon$ (convergence determining value) in the determination of the step S237, the rotation of the shaft B is stopped (step S243) and the processing returns to step S231.

By the above operation, in the interlocking mode between the shafts A and B, the shaft B is rotated so as to eliminate the rotation of the shaft A and if viewed from the diagnostic bed or patient, the X-ray flat panel detector is always directed in the same direction regardless of the insertion direction of the C-arm so that the patient feels safe and further the rotation of the X-ray image displayed on the monitor is quickened.

Next, a modification of the embodiment of the present invention will be described.

Figure 40:
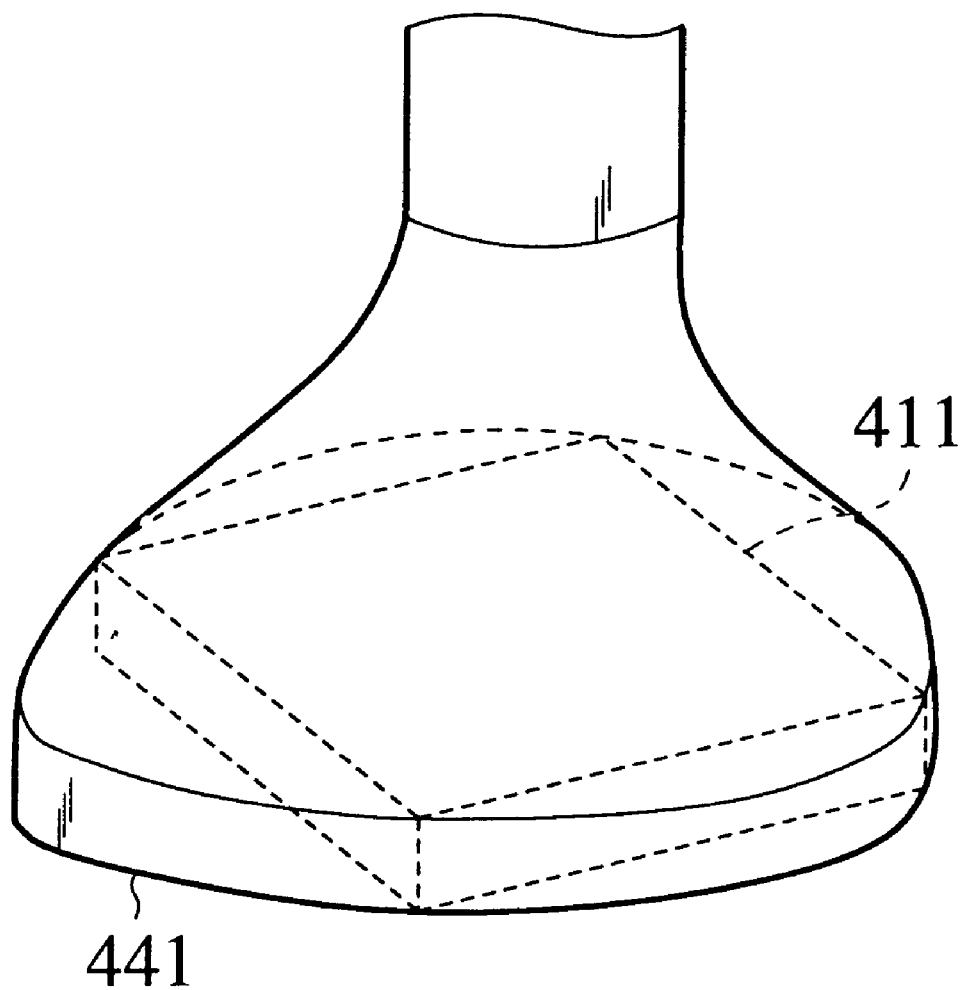
FIG. 40 is a view for explaining a modification of the twelfth embodiment.

In the first modification, as shown in FIG. 40, a circular cover 441 is provided around the X-ray flat panel detector cover 411 of FIG. 36. This cover is made of material having an excellent X-ray transparency, for example, carbon fiber reinforced plastic (CFRP), so as to cover entirely the X-ray flat panel detector.

This cover may be rotated integrally with the X-ray flat panel detector or independently of the X-ray flat panel detector or may be fixed to the top end of the C-arm.

According to a second modification, when a force over a certain level is applied to the joint portion 409 of FIG. 37, the X-ray flat panel detector 411 is rotated freely.

Thus, a spring is interposed between the stepping motor 425 and pinion 433 and a deformation of this spring does not reach a predetermined value within a range of usual load, but a driving force is transmitted from the shaft of the stepping motor 425 to the pinion 433. If a load over a certain level is applied, the deformation of this spring reaches the predetermined value so that the shaft of the stepping motor 425 idles, so that no driving force is transmitted to the pinion 433.

Because the pinion 435 is capable of transmitting a rotation angle of the ring gear 431 to the rotary encoder 429, the rotation angle of the shaft B can be adjusted to a desired value after a force causing an overload is removed.

In the X-ray diagnostic apparatus using the X-ray flat panel detector according to the above described embodiments, if the arm holding the X-ray source and X-ray flat panel detector is inserted from any direction relative to the patient, the patient does not feel any uneasiness and a direction of an image displayed on the monitor can be always maintained to be constant.

It should be understood that many modifications and adaptations of the invention will become apparent to those skilled in the art and it is intended to encompass such obvious modifications and changes in the scope of the claims appended hereto.

What is claimed is:

1. X-ray diagnostic apparatus comprising:
   an X-ray source for irradiating X-ray;
   a flat panel detector for detecting the X-ray irradiated from the X-ray source; and
   a collection processing means for collecting and processing pixel data corresponding to an X-ray irradiation region determined based on, at least, a degree of opening of a beam limiting device of the X-ray source and a distance between the X-ray source and the flat panel detector.

2. X-ray diagnostic apparatus comprising:
   an X-ray source for irradiating X-ray;
   a flat panel detector for detecting the X-ray irradiated from an X-ray source;
   a reading region determining means for, in a condition that the region of the flat panel detector is divided to plural regions, determining a region to be moved to read its pixel data by detecting changes in the pixel data value among the respective regions and
   a control means for controlling so as to read pixel data from the flat panel detector based on a result of a determination of the reading region determining means.

3. X-ray diagnostic apparatus according to claim 1 further comprising an indication means for indicating the X-ray irradiation region to an operator.

4. X-ray diagnostic apparatus according to claim 1 further comprising, if the X-ray irradiation region determined based on the degree of opening of the beam limiting device of the X-ray source and the distance between the X-ray source and the flat panel detector goes out of the flat panel detector, a notifying means for notifying that event.

5. X-ray diagnostic apparatus according to claim 1 wherein the collection processing means sweeps out pixel data corresponding to a region other than the X-ray irradiation region in the flat panel detector in batch when it collects pixel data corresponding to the X-ray irradiation region.

6. X-ray diagnostic apparatus according to claim 5 wherein the collection processing means releases electric charge relating to pixel data corresponding to a region other than the X-ray irradiation region to signal lines provided on the flat panel detector.

7. X-ray diagnostic apparatus according to claim 5 wherein the collection processing means releases electric charge relating to pixel data of a region other than the X-ray irradiation region to power supply lines provided on the flat panel detector.

8. X-ray diagnostic apparatus according to claim 1 further comprising a patient region determining means for determining and extracting pixel data corresponding to the patient from pixel data corresponding to the X-ray irradiation region.

9. X-ray diagnostic apparatus according to claim 8 further comprising a display means for displaying an image based on pixel data corresponding to the X-ray irradiation region or the patient region; and
   a display control means for enlarging or reducing an image based on pixel data corresponding to the X-ray irradiation region or pixel data corresponding to the patient region, depending on a screen size of the display means.

10. X-ray diagnostic apparatus according to claim 1 further comprising an adjusting means for adjusting at least one of a degree of opening of the beam limiting device of the X-ray source and a distance between the X-ray source and the flat panel detector.

11. X-ray diagnostic apparatus according to claim 1 wherein when the collection processing means collects pixel data corresponding to the X-ray irradiation region, it collects data of adjacent pixels together depending on a size of the X-ray irradiation region and a degree of resolution thereof.

12. X-ray diagnostic apparatus comprising:
    an X-ray source for irradiating X-ray;
    a flat panel detector for detecting the X-ray irradiated from the X-ray source;
    an irradiation region detecting means for detecting an X-ray irradiation region based on pixel data from the flat panel detector;
    a patient region detecting means for detecting a patient region from the X-ray irradiation region;
    a display means;
    a setting means for setting all-pixel display mode, irradiation region display mode or patient region display mode; and
    a display control means for controlling so as to display an image based on all pixel data on the display means when the all-pixel display mode is set, an image based on pixel data corresponding to the X-ray irradiation region on the display means when the irradiation region display mode is set or an image based on pixel data corresponding to the patient region on the display means when the patient region display mode is set.

13. X-ray diagnostic apparatus according to claim 12 wherein the display control means compiles and collects adjacent pixel data to a single value from the flat panel detector depending on a size of a region to be displayed on the flat panel detector.

14. X-ray diagnostic apparatus according to claim 12 wherein unless the irradiation region detecting means detects any X-ray irradiation region, the display control means displays that the detection has not been attained.

15. A method for controlling an X-ray diagnostic apparatus comprising an X-ray source for irradiating X-ray to a patient and a flat panel detector for detecting the X-ray irradiated from the X-ray source to irradiate X-ray to the patient plural times, the method comprising:
    conducting a first irradiation of the X-ray from the X-ray source;
    reading pixel data from the flat panel detector;
    detecting a region irradiated with the X-ray on the flat panel detector based on read pixel data;
    selecting a region whose pixel data should be collected from the flat panel detector based on a result of that detection;
    memorizing information of a region whose image data should be collected;
    conducting a second irradiation of the X-ray from the X-ray source;
    reading pixel data from the flat panel detector based on the memorized region information, and
    repeating an irradiation of the X-ray and a reading of the pixel data from the flat panel detector based on the memorized region information.

16. A method for controlling an X-ray diagnostic apparatus comprising an X-ray source for irradiating X-ray to a patient and a flat panel detector for detecting the X-ray irradiated from the X-ray source to irradiate X-ray to the patient plural times, the method comprising:

conducting a first irradiation of the X-ray from the X-ray source;

reading pixel data from the flat panel detector;

detecting a region where a patient exists on the flat panel detector based on the read pixel data;

selecting a region whose pixel data should be collected from the flat panel detector based on a result of that detection;

memorizing information of the region whose image data should be collected;

conducting a second irradiation of the X-ray from the X-ray source;

reading pixel data from the flat panel detector based on the memorized region information, and repeating an irradiation of the X-ray and a reading of the pixel data from the flat panel detector based on the memorized region information.

17. X-ray diagnostic apparatus comprising:

an X-ray source for irradiating the X-ray;

an X-ray beam limiting device for limiting an X-ray irradiation region;

an opening degree setting means for setting a degree of opening of the X-ray beam limiting device;

a flat panel detector for detecting the X-ray irradiated from the X-ray source via the X-ray beam limiting device;

an image processing means for receiving and processing pixel data detected by the flat panel detector; and a control means for controlling the flat panel detector so as to compile adjacent pixel data from the flat panel detector as a single value, depending on the size of an irradiation region relative to the flat panel detector, determined by the opening degree setting means and a processing resolution of the image processing means and then input this value into the image processing means.

18. X-ray diagnostic apparatus according to claim 17 wherein, when a resolution of pixel on the flat panel detector corresponding the size of the irradiation region is higher than the processing resolution of the image processing means, the control means controls the flat panel detector so as to compile adjacent pixel data to a single value and input this value into the image processing means, and when the resolution is lower than the processing resolution of the image processing means, it controls the flat panel detector so as to input the pixel data corresponding to the processing resolution of the image processing means into the image processing means as it is.

19. X-ray diagnostic apparatus according to claim 17 wherein the control means controls the flat panel detector so as to sweep out pixel data other than pixel data to be input to the image processing means in batch.

20. X-ray diagnostic apparatus according to claim 17 wherein the flat panel detector includes:

a plurality of X-ray—electric charge converting means disposed in matrix for generating electric charge corresponding to an amount of the impinging X-ray;

a plurality of accumulating means for accumulating the electric charge generated from the plurality of the X-ray electric charge converting means in each thereof;

a plurality of switching elements each electrically connected to the plurality of the accumulating means;

a scanning line driving means for controlling the plurality of the switching elements in the unit of row;

a plurality of signal lines connected to an output side of the plurality of the switching elements for each line; and a selectively reading means for selectively reading signals on the signal lines, the control means controlling the scanning line driving means so that plural adjacent switching elements are turned ON at the same time.

21. X-ray diagnostic apparatus according to claim 20 wherein the control means controls the selectively reading means so that plural rows of the signal lines are get into reading condition.

22. X-ray diagnostic apparatus according to claim 17 further comprising an irradiation position setting means for setting the X-ray irradiation position relative to the flat panel detector.

23. X-ray diagnostic apparatus comprising:

an X-ray source for irradiating the X-ray;

an X-ray beam limiting device for limiting an X-ray irradiation region;

an opening degree setting means for setting a degree of opening of the X-ray beam limiting device;

a flat panel detector for detecting the X-ray irradiated from the X-ray source via the X-ray beam limiting device;

a region setting means for setting the size of a region in the flat panel detector, whose pixel data should be read;

an image processing means for receiving and processing pixel data detected by the flat panel detector; and a control means for controlling the flat panel detector so as to compile adjacent pixel data from the flat panel detector as a single value, depending on the size of an irradiation region relative to the flat panel detector, determined by the opening degree setting means, a processing resolution of the image processing means and a size of a region set by the region setting means and then input this value into the image processing means.

24. X-ray diagnostic apparatus comprising:

an X-ray source for irradiating the X-ray;

first and second X-ray beam limiting devices for limiting the X-ray irradiation region;

an opening degree setting means for setting the degree of opening of the first X-ray beam limiting device;

a flat panel detector for detecting the X-ray irradiated from the X-ray source via the first and second X-ray beam limiting devices;

a region setting means for setting the size of a region in the flat panel detector, whose pixel data should be read and then setting a degree of opening of the second X-ray beam limiting device based on the size of the set region;

an image processing means for receiving and processing pixel data detected by the flat panel detector; and a control means for controlling the flat panel detector so as to compile adjacent pixel data of the flat panel detector to a single value depending on the size of an irradiation region relative to the flat panel detector, determined by the opening degree setting means and the region setting means and then input this value to the image processing means.

25. X-ray diagnostic apparatus comprising:

an X-ray source for irradiating the X-ray;

an X-ray beam limiting device for limiting an X-ray irradiation region;

an opening degree setting means for setting a degree of opening of the X-ray beam limiting device;

a flat panel detector for detecting the X-ray irradiated from the X-ray source via the X-ray beam limiting device, the flat panel detector having high resolution detecting elements in the center thereof and low resolution detecting elements in a peripheral portion thereof;

an image processing means for receiving and processing pixel data detected by the flat panel detector; and a control means for controlling the flat panel detector so that if the size of an irradiation region relative to the flat panel detector determined by the opening degree setting means is smaller than the size of the low resolution detecting element, pixel data detected by the high resolution detecting element is input to the image processing means as it is and if the size of the irradiation region relative to the flat panel detector determined by the opening degree setting means is larger than the size of the low resolution detecting element, the pixel data detected by the low resolution detecting element and the pixel data detected by the high resolution detecting element are compiled in the unit of adjacent data and input to the image processing means.

26. X-ray diagnostic apparatus comprising:

an X-ray source for irradiating the X-ray;

a flat panel detector for detecting the X-ray irradiated from the X-ray source;

an operating means for operating to move a region in the flat panel detector whose pixel data should be read at real time; and a control means for controlling to read the pixel data in the region moved by the operating means from the flat panel detector.

27. X-ray diagnostic apparatus according to claim 26 further comprising:

frontal X-ray source and lateral X-ray source;

frontal flat panel detector and lateral flat panel detector;

frontal operating means and lateral operating means; and frontal operating means and lateral operating means, the control means reading pixel data in a region moved by the frontal operating means from the frontal flat panel detector and further pixel data moved by the lateral operating means from the lateral flat panel detector.

28. X-ray diagnostic apparatus according to claim 27 wherein if one of the frontal operating means and the lateral operating means is operated, the control means controls to read pixel data in a region moved by the operated operating means from a corresponding flat panel detector and, while determining that the other operating means moves interlockingly with the operated operating means, controls to read pixel data from a corresponding flat panel detector.

29. X-ray diagnostic apparatus according to claim 28 wherein the control means, if one of the frontal operating means and the lateral operating means is operated, determines that the other operating means is moved interlockingly with an operated operating means in a direction perpendicular thereto.

30. X-ray diagnostic apparatus according to claim 26 further comprising a reading size setting means for setting the size of a region in a flat panel detector whose pixel data should be read.

31. X-ray diagnostic apparatus according to claim 30 further comprising an X-ray beam limiting device for limiting an X-ray irradiation region, the control means controlling a degree of opening of the X-ray beam limiting device corresponding to the size of a region set by the reading size setting means and controlling the X-ray beam limiting device so as to move a region to be irradiated with the X-ray corresponding to an operation for moving a reading region by the operating means.

32. X-ray diagnostic apparatus comprising:

an X-ray source for irradiating X-ray;

a flat panel detector for detecting the X-ray irradiated from an X-ray source;

a memorizing means for memorizing a moving pattern of a region in the flat panel detector whose pixel data should be read; and a control means for controlling to read the pixel data from the flat panel detector according to the moving pattern memorized in the memorizing means.

33. X-ray diagnostic apparatus comprising:

an X-ray source for irradiating X-ray;

a flat panel detector for detecting the X-ray irradiated from an X-ray source;

a holding means rotatable relative to a patient, holding the flat panel detector and the X-ray source such that they oppose each other and further holding the flat panel detector such that it is rotatable; and a control means for detecting a rotation angle of the holding means relative to the patient and controlling an angle of the flat panel detector relative to the holding means so that the angle of the flat panel detector relative to the patient is constant.

34. X-ray diagnostic apparatus according to claim 33 further comprising a protective cover mounted on the flat panel detector for protection.

35. X-ray diagnostic apparatus according to claim 33 wherein the flat panel detector rotates freely when an outside force over a predetermined value is applied thereto.

* * * * *